(12) United States Patent
Chhaya et al.

(10) Patent No.: US 11,529,227 B2
(45) Date of Patent: Dec. 20, 2022

(54) IMPLANTS AND METHOD FOR FORMING AN IMPLANT

(71) Applicant: BellaSeno GmbH, Leipzig (DE)

(72) Inventors: Mohit Chhaya, Leipzig (DE); Arpita Desai, Leipzig (DE); Navid Khani, Leipzig (DE); Sara Lucarotti, Leipzig (DE)

(73) Assignee: BellaSeno GmbH, Leipzig (DE)

( * ) Notice: Subject to any disclaimer, the term of this patent is extended or adjusted under 35 U.S.C. 154(b) by 0 days.

(21) Appl. No.: 17/012,686

(22) Filed: Sep. 4, 2020

(65) Prior Publication Data

US 2021/0186678 A1 Jun. 24, 2021

(30) Foreign Application Priority Data

Sep. 4, 2019 (EP) .................................... 19195332

(51) Int. Cl.
*A61F 2/12* (2006.01)
*B33Y 80/00* (2015.01)
*A61F 2/00* (2006.01)

(52) U.S. Cl.
CPC .............. *A61F 2/12* (2013.01); *A61F 2/0077* (2013.01); *B33Y 80/00* (2014.12); *A61F 2/0059* (2013.01); *A61F 2240/001* (2013.01)

(58) Field of Classification Search
CPC ........ A61F 2/12; A61F 2/0077; A61F 2/0059; A61F 2240/001; A61F 2210/0076; A61F 2240/002; A61F 2250/0023; B33Y 80/00; A61L 2430/04; A61L 27/18; A61L 27/56
See application file for complete search history.

(56) References Cited

U.S. PATENT DOCUMENTS

| 2014/0088716 | A1* | 3/2014 | Zubok | ...................... A61F 2/30 623/18.11 |
| 2019/0247180 | A1 | 8/2019 | Limem | |
| 2020/0375726 | A1* | 12/2020 | Limem | ............... A61L 27/3687 |

FOREIGN PATENT DOCUMENTS

| CN | 107638231 A | 1/2018 |
| CN | 207590799 U | 7/2018 |
| CN | 107280810 B | 11/2018 |

(Continued)

OTHER PUBLICATIONS

Extended European Search Report for App. No. EP19195332.2, dated Mar. 26, 2020, 9 pages.

(Continued)

*Primary Examiner* — Brian A Dukert
*Assistant Examiner* — Rebecca Lynee Zimmerman
(74) *Attorney, Agent, or Firm* — Riverside Law LLP

(57) ABSTRACT

Embodiments herein relate to an implant for insertion into a patient. The implant comprises a plurality of unit cells arranged to form a three-dimensional lattice structure, the three-dimensional structure comprising a resting volume of the implant. The plurality of unit cells are arranged to form a porous network of the three-dimensional structure, and wherein the three-dimensional structure is a reversibly compressible three-dimensional structure, wherein a bulk porosity of the three-dimensional structure of the implant is at least 50%. Also disclosed is a method of tissue reconstruction or tissue augmentation. The method comprises implanting into the body of a subject an implant of the disclosure.

19 Claims, 39 Drawing Sheets

(56) References Cited

FOREIGN PATENT DOCUMENTS

| | | |
|---|---|---|
| CN | 109172044 A | 1/2019 |
| EP | 2995278 A1 | 3/2016 |
| WO | 2017050837 A1 | 3/2017 |
| WO | 2018130949 A1 | 7/2018 |

OTHER PUBLICATIONS

International Search Report and Written Opinion for App. No. PCT/US2020/074690, dated Dec. 23, 2020, 13 pages.
Written Opinion of the International Preliminary Examining Authority for App. No. PCT/EP2020/074690, dated Sep. 14, 2021, 7 pages.

* cited by examiner

Standing diagram

Running, Jumping Walking diagram

IMPLANTS AND METHOD FOR FORMING AN IMPLANT

CROSS-REFERENCE TO RELATED APPLICATIONS

The present application claims the right of priority of European patent application 19195332.2 filed with the European Patent Office on 4 Sep. 2019, the entire content of which is incorporated herein for all purposes.

FIELD OF THE INVENTION

The embodiments described herein relate to the field implants, and in particular to implants suitable for soft tissue reconstruction to be inserted into a patient, and a method for forming an implant as well as to the use of the implant for tissue reconstruction and/or tissue augmentation.

BACKGROUND OF THE INVENTION

Breast augmentation and reconstruction mammaplasty have been in practice for decades and are highly prevalent surgeries performed worldwide. While overall patient satisfaction is high, common long-term effects include breast tissue atrophy, accelerated ptosis (e.g. drooping) and inframammary fold breakdown. Increasing evidence attributes these events to the durative loading and compressive forces introduced by breast implants. For example, mechanical challenges exceeding the elastic capacity of the breast tissue components eventually lead to irreversible tissue stretching. Traditional silicone implants may be filled with incompressible fluids, and may introduce a heavy load which causes tissue stretching. Moreover, over time silicone implants may burst causing health issues, and may lead to additional surgeries. Some implants may include space-occupying structures which may be filled with fluid. For example, International patent application WO 2016/038083 and Chhaya et al. Transformation of Breast Reconstruction via Additive Biomanufacturing. *Sci. Rep.* 6, 28030; doi: 10.1038/srep28030 (2016) discloses an implant that has a three-dimensional scaffold structure having voids, all of which are filled with space-occupying structures. The space-occupying structures are removably attached to the three-dimensional scaffold structure and are configured to prevent invasion of tissue and/or of individual cells. After implantation of the implant, e.g. 6-8 weeks after implantation of the implant) the space-occupying structure are removed in a second surgery from the residual parts of the implant and the site of implantation.

SUMMARY

Various embodiments relate to providing a lightweight implant which decreases the effects of ptosis in a patient and reduces adverse reactions by a patient to an implant.

The embodiments described herein relate to an implant for insertion into a patient. The implant comprises a plurality of unit cells arranged to form a three-dimensional lattice structure, the three-dimensional structure comprising a resting volume of the implant. The plurality of unit cells are arranged to form a porous network of the three-dimensional structure, and the three-dimensional structure is a reversibly compressible three-dimensional structure, wherein a bulk porosity of the three-dimensional structure (101) of the implant is at least 50%.

Various embodiments relate to a further implant for insertion into a patient. The implant comprises a porous three-dimensional scaffold structure comprising an arrangement of unit cells, wherein the plurality of unit cells are arranged to form a porous network of the three-dimensional structure, wherein an average pore size of the plurality of unit cells of the three-dimensional structure is at least 0.5 mm.

Various embodiments relate to a further implant for insertion into a patient. The implant comprises a three-dimensional porous scaffold structure comprising a plurality of hollow channels extending between a first outer surface region and a second outer surface region of the three-dimensional porous scaffold structure, wherein the porous scaffold structure comprises a surface-degradable polymer material. The first outer surface region is configured to face a chest wall of the patient receiving the implant, wherein a geometry of the second outer surface region represents a geometry of a breast to be constructed by the implant, and wherein the plurality of hollow channels are configured to be aligned with Cooper's ligaments of the patient receiving the implant.

Various embodiments relate to a method for forming an implant. The method comprises sequentially printing layers to form a three-dimensionally (3D) printed structure, the 3D printed structure defining a resting volume of the implant to be formed, wherein each printed layer comprises a lattice arrangement of two-dimensional unit cells, wherein the three-dimensionally printed structure has a porosity such that the three-dimensional printed structure is compressible to at least 80% of its resting volume.

Finally, the invention also relates to a method of tissue reconstruction or tissue augmentation, wherein the method comprises implanting into the body of a subject an implant as defined herein.

BRIEF DESCRIPTION OF THE DRAWINGS

The foregoing and other features of the present disclosure will become more fully apparent from the following description and appended claims, taken in conjunction with the accompanying drawings. It is understood that the accompanying drawings depict only several embodiments in accordance with the present disclosure and are, therefore, not to be considered limiting of its scope. The disclosure will be described with additional specificity and detail through use of the accompanying drawings, such that the advantages of the present disclosure can be more readily ascertained, in which:

FIG. 10B shows that there were no signs of chronic inflammation after implantation of the implant/scaffold of the invention in a mini pig as described here;

DETAILED DESCRIPTION

Figure 1A:
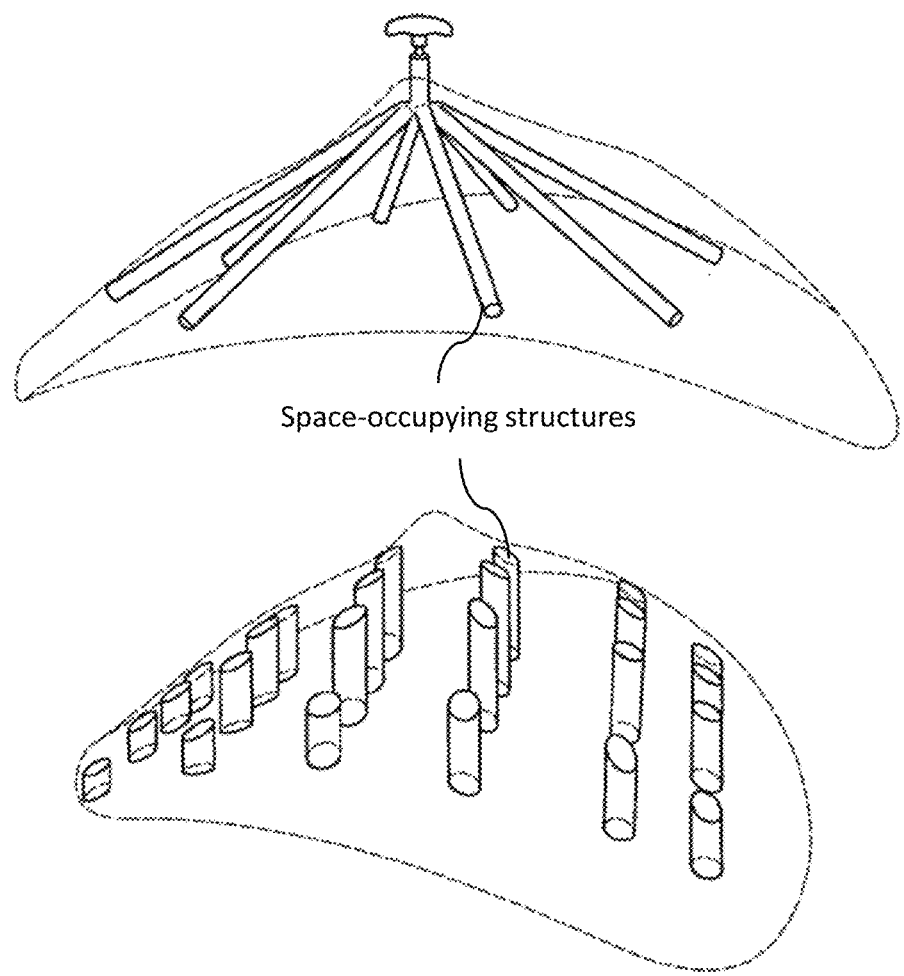
FIG. 1A shows an illustration of the implant described in International patent application WO 2016/038083 that comprises space-occupying structures.

In the following detailed description, reference is made to the accompanying drawings that show, by way of illustration, specific embodiments in which the claimed subject matter may be practiced. These embodiments are described in sufficient detail to enable those skilled in the art to practice the subject matter. It is to be understood that the various embodiments, although different, are not necessarily mutually exclusive. For example, a particular feature, structure, or characteristic described herein, in connection with one embodiment, may be implemented within other embodiments without departing from the spirit and scope of the claimed subject matter. References within this specification to "one embodiment" or "an embodiment" mean that a particular feature, structure, or characteristic described in connection with the embodiment is included in at least one implementation encompassed within the present description. Therefore, the use of the phrase "one embodiment" or "in an embodiment" does not necessarily refer to the same embodiment. In addition, it is to be understood that the location or arrangement of individual elements within each disclosed embodiment may be modified without departing from the spirit and scope of the claimed subject matter. The following detailed description is, therefore, not to be taken in a limiting sense, and the scope of the subject matter is defined only by the appended claims, appropriately interpreted, along with the full range of equivalents to which the appended claims are entitled. In the drawings, like numerals refer to the same or similar elements or functionality throughout the several views, and that elements depicted therein are not necessarily to scale with one another, rather individual elements may be enlarged or reduced in order to more easily comprehend the elements in the context of the present description.

The terms "over", "to", "between" and "on" as used herein may refer to a relative position of one layer with respect to other layers. One layer "over" or "on" another layer may be directly in contact with the other layer or may have one or more intervening layers. One layer "between" layers may be directly in contact with the layers or may have one or more intervening layers.

Figure 1B:
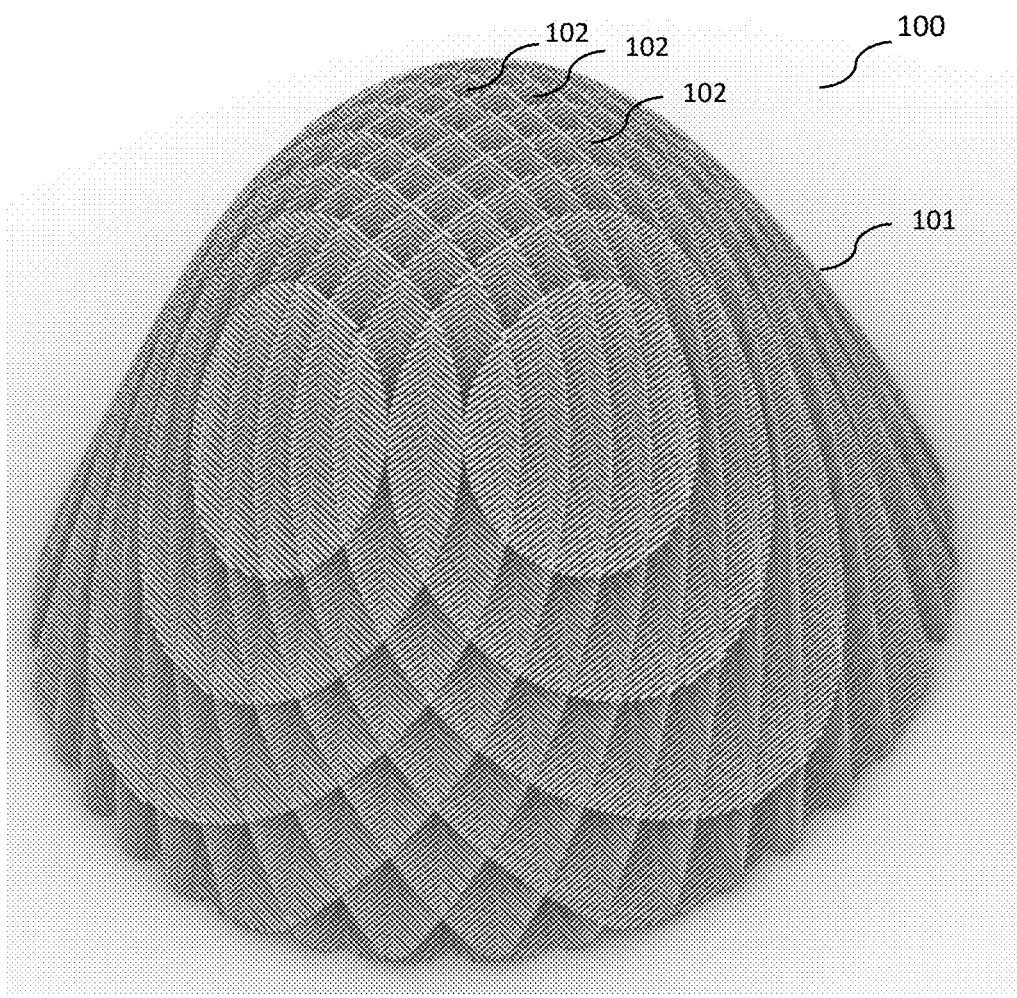
FIG. 1B shows an illustration of an implant of the invention for insertion into a patient.

FIG. 1B shows an illustration of an implant 100 of the invention for insertion into a patient.

The implant 100 comprises a plurality of unit cells 102 arranged to form a three-dimensional lattice structure 101. The three-dimensional structure 101 comprises a resting volume of the implant 100. The plurality of unit cells 102 are arranged to form a porous network of the three-dimensional structure 101, and the three-dimensional structure 101 is a reversibly compressible three-dimensional structure.

The three-dimensional lattice structure 101 may be a mesh-like structure. For example, the implant 100 may include a plurality of lines configured to form the mesh-like structure. Each unit cell 102 of the plurality of unit cells may 102 include, and/or may be formed from intersecting (or e.g.

criss-crossing) lines of the plurality of lines forming and/or defining the individual unit cells 102 (e.g. forming walls enclosing the individual unit cells). The plurality of lines may form and/or contribute to the overall mesh-like three-dimensional lattice structure 101. The intersecting lines may be arranged, so that each unit cell 102 formed from the intersecting lines may include or may be referred to as a pore, having a pore size. Thus, the plurality of intersecting lines may form or define the plurality of pores of the unit cell 102. For example, the intersecting lines may form or define a geometry (e.g. shape, dimension, pore size) of the individual unit cells 102 (e.g. each unit cell 102) of the three-dimensional structure 101. The plurality of unit cells 102 may be arranged to form the porous network of the three-dimensional structure 101. The porous network may refer to (and/or may include) the pores of the plurality of unit cells 102 within the three-dimensional structure 101.

A unit cell 102 may be the smallest and most basic unit of the three-dimensional lattice structure 101. The intersecting lines of the plurality of lines may be configured to form repeated unit cells 102 which form the three-dimensional lattice structure 101. For example, the unit cells 102 may be repeated throughout at least (equal to or larger than) 80% (or e.g. at least 90%, or e.g. at least 95%) of the resting volume of the three-dimensional lattice structure 101. The lattice structure 101 may thus include a plurality of adjacent (e.g. directly adjacent) unit cells, connected to each other throughout the lattice structure 101.

The resting volume (cm$^3$) of the implant 101 may be the volume of the implant 101 before inserting the implant 101 into the patient. The resting volume of the implant 101 may be the volume of the implant 101 when only one outer surface of the implant 101 experiences an external force. For example, when the implant 101 is at rest on (or in contact with) a carrier surface (e.g. a table surface, or e.g. a board). For example, a first outer surface of the implant may be in contact with the carrier surface, and a second (opposite facing) outer surface may be free from any compressive forces. In other words, the resting volume of the implant 101 may be the volume of the implant 101 without opposing compressive forces acting on the surfaces of the implant. When a (physical or mechanical) compression force is exerted on more than one outer surface of the implant 101, the implant 101 may be compressible to at least 80% (or e.g. at least 70%, or e.g. at least 60%, or e.g. at least 50%, or e.g. at least 30%, or e.g. at least 20%, or e.g. at least 10%) of its resting volume. Being compressible to at least 80% refers to the implant being able to attain 80% or smaller of its resting volume (because of compression). The resting volume of the implant 101 may be derived based on a construction volume (the desired or required volume) of a breast to be constructed by the implant 101, for example. The implant 101 may be configured to be compressible to at least the construction volume, so that the implant comprises or attains the construction volume of the breast after insertion into the patient.

The individual unit cells 102 of the plurality of unit cells 102 may be spring-like unit cells. A spring-like unit cell may be compressible to at least 80% (or e.g. at least 70%, or e.g. at least 60%, or e.g. at least 50%, or e.g. at least 30%, or e.g. at least 20%, or e.g. at least 10%) of its original volume. As used herein, compressible to at least 80% refers to being compressible to 80% or less of its original volume. The spring-like unit cells may be reversibly compressible. By being reversibly compressible, each unit cell 102 may be able to recover or return to its original (resting) volume after a compression force has been removed (even at the same ambient pressure and temperature). A reversibly compressible spring-like unit cell may be configured to recover to at least 80% (or e.g. at least 90%, or e.g. at least 95%, or e.g. at least 98%, or e.g. up to 100%) of its original volume, after the compression force exerted on the implant 101 is removed. As used herein, recover to at least 80% refers to being able to recover to 80% or more of its original volume.

Figure 1C:
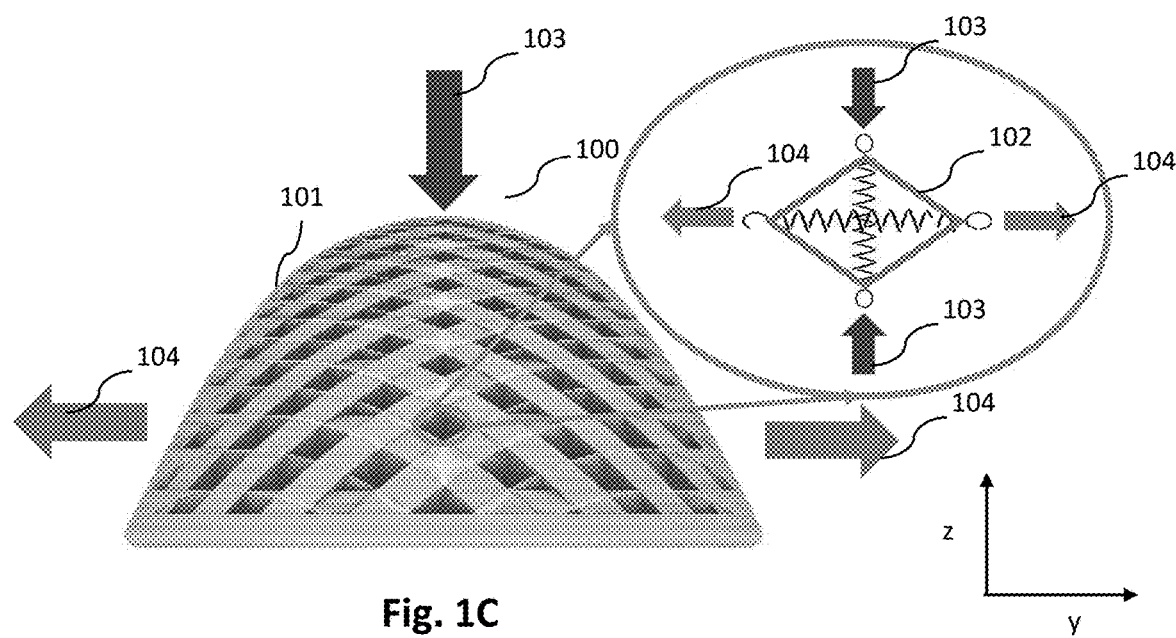
FIGS. 1C and 1D show illustrations of reversible compressibility of spring-like unit cells and the reversible compressibility of the implant of the invention.
Figure 1D:
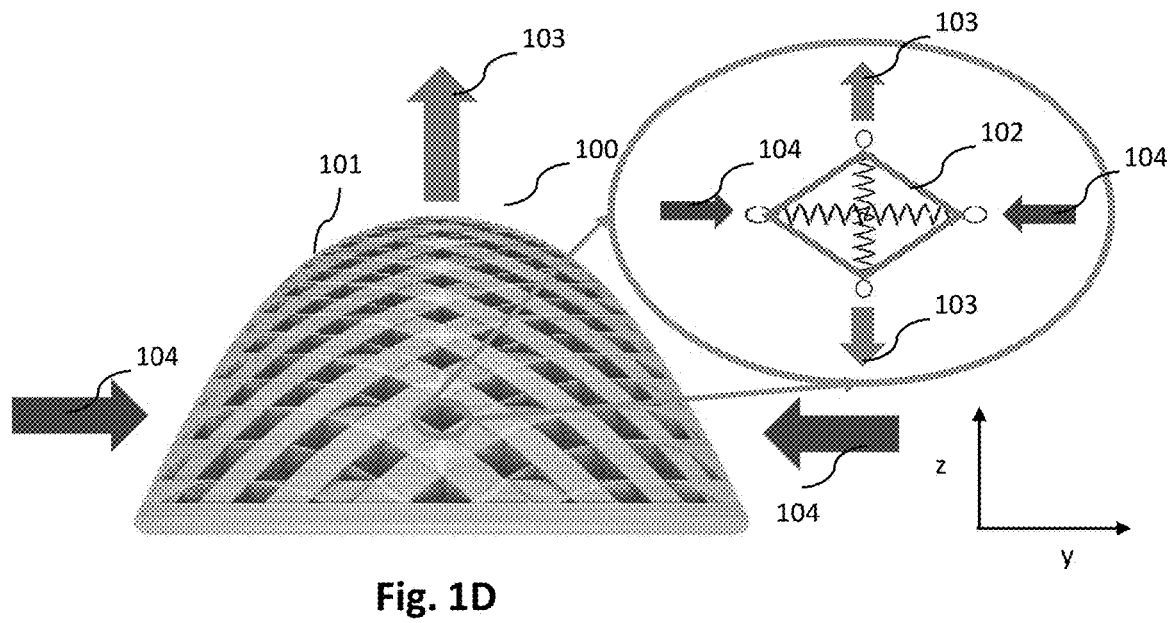

FIGS. 1C and 1D show illustrations of reversible compressibility of the spring-like unit cells 102 and the reversible compressibility of the implant 100.

The three-dimensional structure 101 may be a reversibly compressible three-dimensional structure comprising the plurality of reversibly compressible unit cells 102. The spring-like implant 100 may provide shape stability. The spring-like implant 100 may deform if a force 103 is applied to the implant, and the implant 100 may recover its shape when or after the force is released. The ability of the implant 100 to recover its shape may avoid pore obstruction and/or any extra forces being exerted on the chest cavity, which may cause damages to the patient's tissues and/or to the lungs. The implant 100 may be a soft tissue reconstruction implant (i.e. an implant for and/or suitable for soft tissue reconstruction).

As shown in FIG. 1C, the reversibly compressible structure of the implant 100 and the reversibly compressible unit cells 102 may transfer the forces acting along one direction (e.g. opposing compressive forces 103 along the z-axis) to a different direction, such as a perpendicular direction 104 (e.g. along the x-direction).

As shown in FIG. 1D, once the compressive forces 103 are released (denoted by the change in direction of the arrows of 103), the energy stored during this process may act in the opposite direction as when the compressive forces 103 were being applied (denoted by the change in direction of the arrows of 104). This may help the shape of the implant 100 to spring back and recover its original shape (e.g. at least 80% of its resting volume).

The individual spring-like unit cells 102 may be reversibly compressible in at least one cartesian direction, and/or in three cartesian directions. Although FIGS. 1C and 1D show the unit cells 102 being compressible in the z-direction, it may be understood that the spring-like unit cells 102 may be reversibly compressible in three cartesian directions and/or in any direction in a three-dimensional space.

FIGS. 2A to 2G show different illustrations of an implant 200 of the invention to be inserted into a patient. The implant 200 may include one or more or all of the features of the implant 100 described in connection with FIGS. 1B to 1D, and various other features.

Figure 2A:
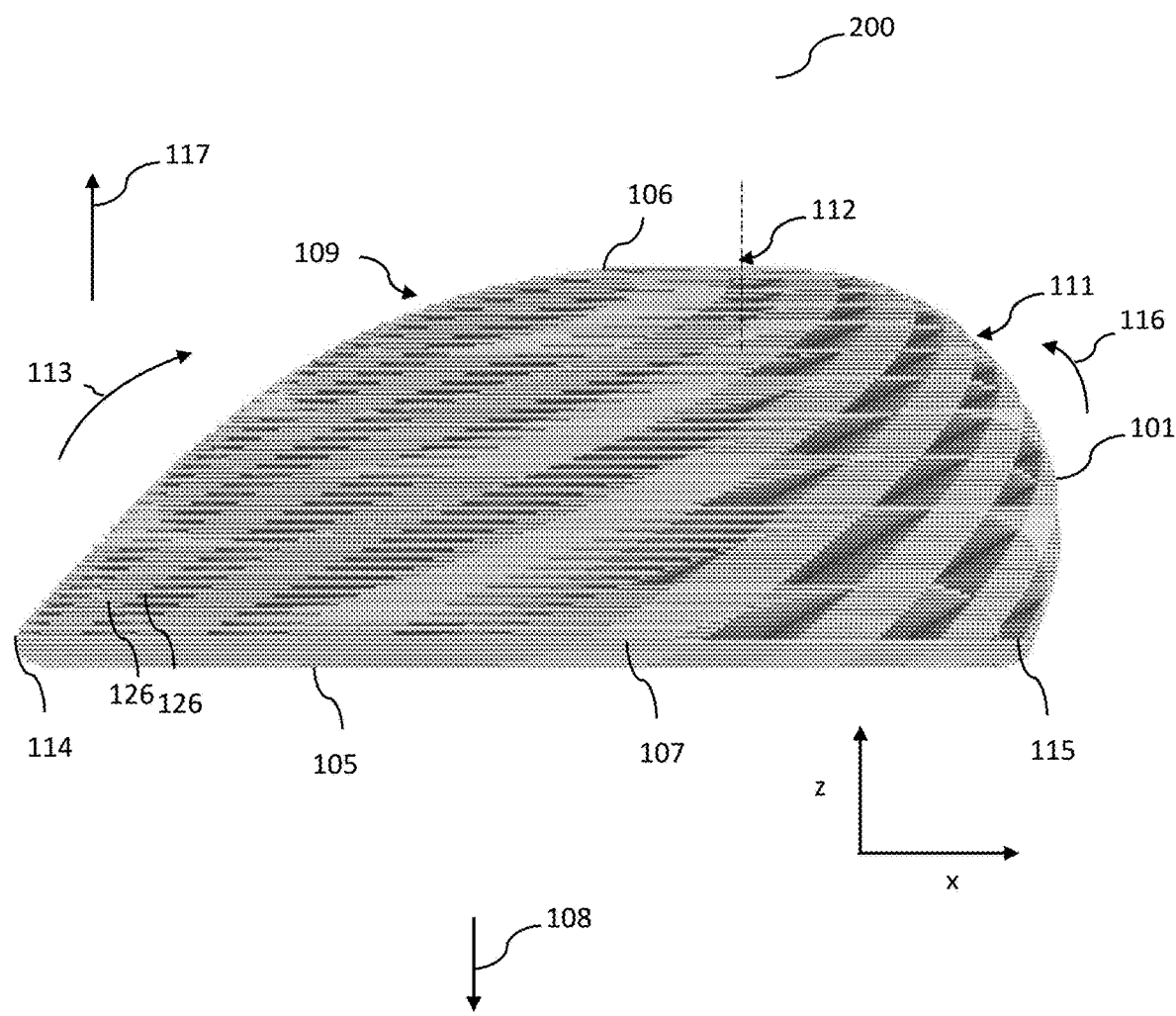
FIG. 2A shows a perspective side view illustration of an implant to be inserted into a patient.

FIG. 2A shows a perspective side view illustration of the implant 200. The three-dimensional structure 101 of the implant 200 may include an arrangement of layers 126. The arrangement of layers 126 may include (or may be) a plurality of lateral layers 126 (e.g. parallel to the x-y plane) arranged successively over each other in the z-direction (e.g. vertical direction). For example, the implant 200 may be formed by sequentially printing layers 126 to form the three-dimensionally (3D) printed scaffold structure 101. Arrow 117 indicates a print direction (e.g. in the z-direction) of the sequential arrangement of successive layers 126. Each lateral layer 126 of the arrangement of layers 126 may include a two-dimensional lattice arrangement of a plurality of two-dimensional unit cells 102. The sequential arrangement (by printing) of layers 126 on top of each other may lead to the forming of the three-dimensional structure 101, with the edges (or perimeter) of the plurality of layers 126 defining the shape and/or geometry of the second outer surface region 106.

The three-dimensional structure 101 of the implant 200 may include a first outer surface region 105 and a second (different and/or opposite facing) outer surface region 106. It may be understood that an outer surface region may refer to (or may be) an outermost surface, an outermost layer, and/or an outermost contour of the implant 200. An outermost surface and outermost contour may be formed from one or more layers or lines. An outer surface region may refer to (or may be) an outermost group of layers (e.g. a single outermost layer, or e.g. an outermost plurality of layers) of the implant 200. An outer surface region may refer to an exterior facing surface of the implant 100.

The first outer surface region 105 of the implant 200 may include, or may have a first surface curvature. The first outer surface region 105 of the implant 200 may be the largest planar (or e.g. flattest) surface of the implant. For example, the first outer surface region 105 may be a flattest surface of the implant and/or surface with the least (or smallest) amount of curvature. As shown in FIG. 2C, the first outer surface region 105 of the implant 200 may be parallel to a two-dimensional (x-y) cartesian plane. Alternatively, or optionally, a plane of best fit of the first outer surface region 105 may be parallel to the two-dimensional (x-y) cartesian plane.

The second outer surface region 106 of the implant 200 may include, or may have a second surface curvature different to the first surface curvature. The second surface curvature may be greater than the first surface curvature. The second outer surface region 106 of the implant 200 may be contiguous to (e.g. abutting) the first outer surface region 105 of the implant 200 at a perimeter 107 (e.g. a circumference) of the first outer surface region 105. For example, second outer surface region 106 of the implant 200 may abut the first outer surface region 105, wherein the perimeter 107 of the first outer surface region 105 may be a shared edge (or interface) between the first outer surface region 105 and the second outer surface region 106.

The second outer surface region 106 may have a geometry (e.g. the shape, curvature, size) which represents a geometry of a patient's breast to be constructed by the implant 200. For example, the second outer surface region 106 may include an upper pole portion 109 and a lower pole portion 111. The upper pole portion 109 may have a geometry of an upper portion of the breast to be constructed by the implant 200. The upper portion of the breast may be the region of the breast above the nipple region of the patient towards the head of the patient. The lower pole portion 111 may have a geometry of a lower portion of the breast to be constructed by the implant 200. The lower portion of the breast may be a region of the breast below the nipple region of the patient towards the feet of the patient. The upper pole portion 109 and the lower pole portion 111 may meet (or may be coincident) at an apex region 112 of the second outer surface region 106. The location (or position) of the apex region 112 at the second outer surface region 106 of the implant may be based on (and/or may coincide with) the location (or position) of the nipple/areola of the breast to be constructed by the implant 200.

Figure 2B:
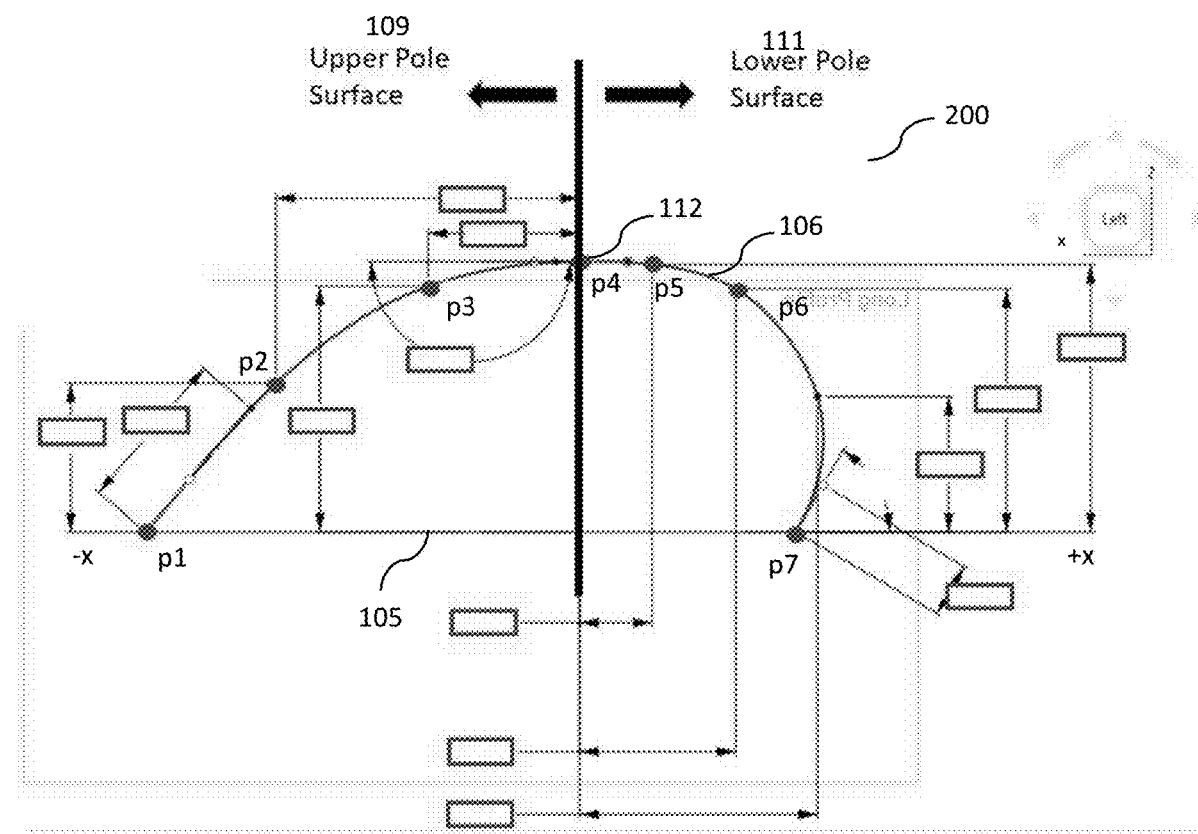
FIG. 2B shows a cross-sectional side view illustration of the implant showing an upper pole portion and a lower pole portion of the implant.
Figure 2C:
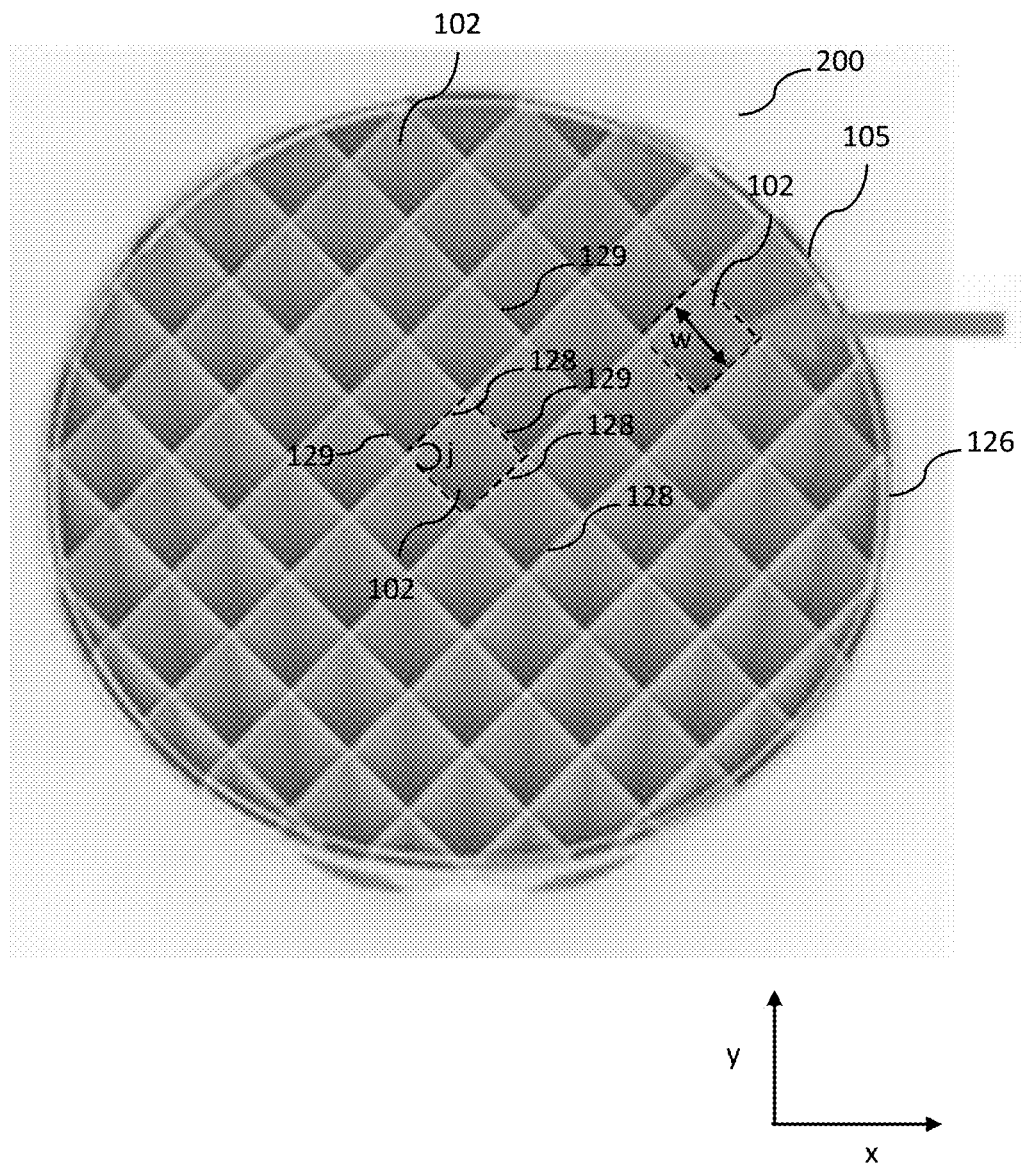
FIG. 2C shows a top view (plan view) of the first outer surface region of an implant.

FIG. 2B shows a cross-sectional side view illustration of the implant 200. The illustration shows the upper pole portion 109 and the lower pole portion 111 of the implant 200.

In the cross-sectional side view, the first outer surface region 105 may be regarded as straight line extending along (e.g. in parallel to) a cartesian x-axis (e.g. from −x to +x). The first outer surface region 105 may have a gradient equal to zero, for example. Generally, a (surface) curvature of the upper pole portion 109 and a (surface) curvature) of the lower pole portion 111 of the second outer surface region 106 may each be larger than a (surface) curvature of the first outer surface region 108. Alternatively, a curvature of the upper pole portion 109 of the second outer surface region 106 may be smaller than or equal to Da curvature of the first outer surface region. The contours and shapes of the upper pole portion 109 and the lower pole portion 111 of the second outer surface region 106 may be controlled based on the desired size and shape of the implant 200.

The curvature and/or contours of the upper pole portion 109 and the lower pole portion 111 may be based on controlling at least one of projection, height and width (symbolized by the boxes) of each of a plurality of sections of the second outer surface region 106. The plurality of sections may be defined based on a plurality of points (e.g. p1 to p7) on the second outer surface region 106. Each section may lie between 2 points at the second outer surface region 106. The distances between the points and the number of points may also be selectively controlled.

A cartesian z-axis may be located at (e.g. directly at) the apex region 112 of the second outer surface region 105 (e.g. at x=0). The upper pole portion 109 of the second outer surface region 106 may lie in the −x region, and the lower pole portion 111 of the second outer surface region 106 may lie in the +x region. Generally, the sections of the upper pole portion 109 may have a positive gradient with respect to the x-axis and the z-axis. A point p4 defining an apex region 112 (e.g. a mid-point of the apex region 112) may be located at x=0. The sections of the upper pole portion 109 nearer to the apex region 112 (e.g. nearer point 4) may have a smaller gradient, e.g. a gradient approaching zero. For example, section p3 to p4 may have a smaller gradient than section p2 to p3, and section p2 to p3 may have a smaller gradient than section p1 to p2. Generally, the sections of the lower pole portion 111 may have a negative gradient with respect to the x-axis and the z-axis. The sections of the lower pole portion 111 nearer to the apex region 112 (e.g. nearer point 4) may have a smaller gradient, e.g. a gradient approaching zero. For example, section p4 to p5 may have a smaller gradient than section p5 to p6. Depending on the desired shape or geometry of the implant 200, sub-sections of the lower pole portion 111 may have a positive gradient (e.g. a sub-section between section p6 to p7). In this way, a curvature of the lower pole portion 111 of the second outer surface region 106 may appear to be larger than the curvature of the upper pole portion 109 of the second outer surface region 106.

FIG. 2C shows a top view (plan view) of the first outer surface region 105 of the implant 200.

In the top view, the first outer surface region 105 may have a circular or ellipsoidal shape. The first outer surface region 105 may include (or may refer to) a first layer 126 of the arrangement of layers. As shown in FIG. 2C, each lateral layer 126 may include an arrangement of two-dimensional unit cells 102. The two-dimensional unit cells 102 may be rhomboid-shaped (or diamond-shaped, or rhombus-shaped) unit cells.

Figure 2D:
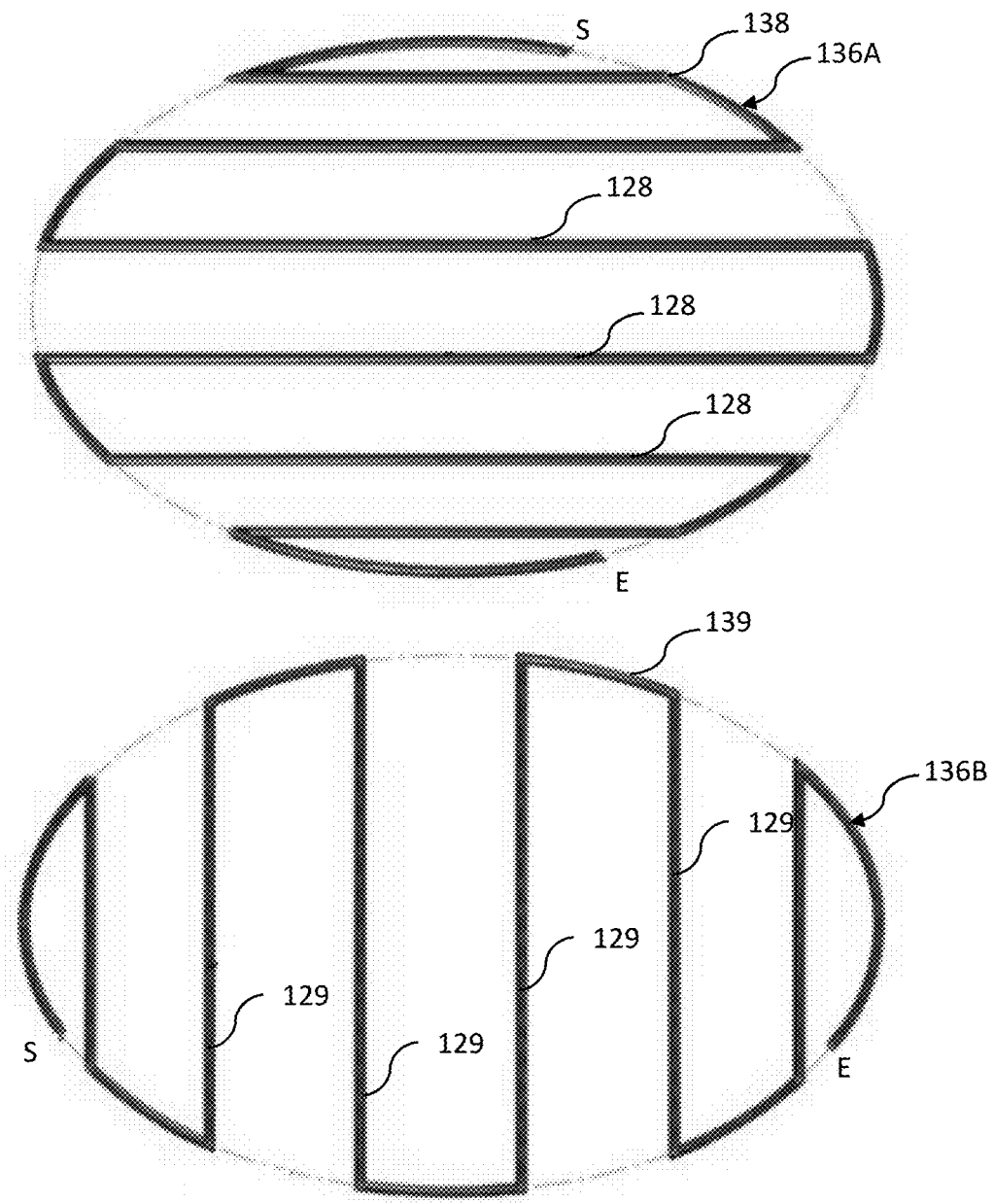
FIG. 2D shows a top view of two sublayers which may intersect to form a unit cell.

FIG. 2D shows a top view of two sublayers 136A, 136B, which may intersect to form a unit cell.

Each lateral layer 126 of unit cells may include a first sublayer 136A (or a first group of sublayers) comprising lines 128 oriented in a first direction, and a second sublayer 136B (or second group of sublayers) of lines 129 oriented in a second direction different to the first direction. The lines of each sublayer may be part of a continuous sublayer line meandering continuously from a start point, S, of the sublayer to an end point, E, of the sublayer. For example, the lines 128 of first sublayer 136A may be part of a continuous sublayer line 138 meandering continuously from the start point, S, to the end point, E, of the first sublayer 136A. For example, the lines 129 of the second sublayer 136B may be part of a continuous sublayer line 139 meandering continuously from the start point, S, to the end point, E, of the second sublayer 136B. The intersecting lines forming a unit cell may be straight lines, or alternatively, the lines may be sinusoidal lines, wherein the unit cells may have a "freeform" shape. The lines 128, 129 within each respective sublayer 136A, 136B may be parallel to each other (e.g. an acute angle between the lines within a sublayer, or between the line of best fit for sinusoidal lines, may lie within +/−5°). The plurality of lines 128 of the first sublayer and the plurality of lines 129 of the second sublayer may intersect at intersection points or intersection regions to form a two-dimensional lattice arrangement of two-dimensional unit cells of the later layer 126. The two-dimensional unit cells 102 of each layer 126 of the stacked layer arrangement may form the three-dimensional lattice structure 101.

As shown in FIG. 2C, each unit cell 102 of a lateral layer 126 may include or may be formed from intersecting lines 128, 129 from adjacent sublayers 136A, 136B defining a pore size of the unit cell 102. For example, two adjacent (and parallel) lines 128 of a first sublayer 136A may intersect with two adjacent (and parallel) lines 129 of a second (adjacent) sublayer 136B. The area of a unit cell enclosed by the intersecting lines may have the rhomboid (or diamond shape, or rhombus shape). In some examples, a smallest angle, j, between two intersecting lines of a unit cell may lie between 5° and 90° (or e.g. between 10° and 80°, or e.g. between 30° and 60°).

Each two-dimensional unit cell 102 may have a pore size, defining the dimension of the unit cell 102. The pore size, w, of the unit cell 102 of a layer may be the minimal dimension (or width) of the pore, e.g. the smallest distance of the pore measured between two lines (e.g. opposite facing lines) defining the unit cell 102.

The three-dimensional structure 101 of the implant 200 may be constructed from the plurality of unit cells 102 having a range of different pore sizes. As shown in FIG. 2C, the first layer 126 may be the outermost layer at the first outer surface region 105. Thus, the pore size of the unit cell 102 may also be the surface pore size of surface pores (openings) of the first outer surface region. A (minimal or smallest) surface pore size, w, of the plurality of unit cells at (or of) the first outer surface region 105 of the implant 200 may be at least (e.g. equal to or larger than) 2 mm (or e.g. at least 6 mm, or e.g. at least 8 mm). A surface pore size of at least 80% (or e.g. at least 70%, or e.g. at least 80%) of the unit cells 102 at (or of) the first outer surface region 105 may be at least 2 mm (or e.g. at least 0.75 mm, or e.g. at least 1 mm).

The sizes of openings at the surface of the implant 200 (e.g. surface pore sizes) may vary depending on their position at the implant 200. An (average) surface pore size of openings at (or of) the first outer surface region 105 of the three-dimensional structure may be at least (e.g. equal to or larger than) 10% (or e.g. at least 25%, or e.g. at least 30%, or e.g. at least 35%) larger than an (average) surface pore size of openings at the second outer surface region 106 of the three-dimensional structure 101. Additionally, or optionally, the (average) surface pore sizes at the first outer surface region 105 may be larger than the (average) surface pore sizes at the lower pole portion 111 and larger than the (average) surface pore sizes at the upper pole portion (109) of the second outer surface region 106.

Although rhomboid (or diamond-shaped) unit cells 102 have been shown in FIG. 2C, it may be understood that optionally, the plurality of two-dimensional unit cells 102 may be polygonal unit cells. For example, the plurality of two-dimensional unit cells may be triangular-shaped unit cells, diamond-shaped unit cells, rhomboid-shaped unit cells, square-shaped unit cells, parallelogram shaped unit cells and/or hexagonal-shaped unit cells. It may be understood that the implant 200 may include more than one type of unit cells throughout the volume of the implant 200, such as a mixture of unit cells. In an example, the implant 200 may include predominantly diamond-shaped unit cells (e.g. more than 50%, or e.g. more than 60%, or e.g. more than 70%, or e.g. more than 80% of the unit cells may be diamond-shaped unit cells). Alternatively, instead of being two-dimensional unit cells, the unit cells 102 of the plurality of unit cells 102 may include (or may be) three-dimensional unit cells, with a plurality of planar facets. Each planar facet of the three-dimensional unit cell may define a pore and/or pore size of the three-dimensional unit cell 102. Generally speaking, each three-dimensional unit cell 102 may include at least four pores. For example, a tetrahedral three-dimensional unit cells may include at least four openings (or pores) formed by the four triangular faces of the tetrahedral unit cell. For example, a hexagonal three-dimensional unit cell may include six openings (or pores) at the respective six facets of the hexagonal unit cell.

An average thickness of the plurality of lines may lie between 0.1 mm and 5 mm (or e.g. between 0.1 mm and 2 mm, or e.g. between 0.5 mm and 1.5 mm). Thus, each sublayer 136A having lines oriented in the first direction may be separated from an adjacent (or successive) sublayer 136A having lines oriented in the (same) first direction by a sublayer 136B having lines oriented in the second (different) direction. Thus, each sublayer 136A oriented in the first direction may be separated from an adjacent (or successive) sublayer 136A oriented in the (same) first direction by a separation distance of between 0.1 mm and 5 mm (or e.g. between 0.1 mm and 2 mm, or e.g. between 0.5 mm and 1.5 mm). Similarly, each sublayer 136B oriented in the second direction may be separated from an adjacent (or successive) sublayer 136B oriented in the (same) second direction by a separation distance of between 0.1 mm and 5 mm (or e.g. between 0.1 mm and 2 mm, or e.g. between 0.5 mm and 1.5 mm). This may result in a loosely spaced arrangement of layers and sub-layers, which allows a freedom of movement (e.g. due to compression, stretching, translation) of the individual lines with respect to each other.

Figure 2E:
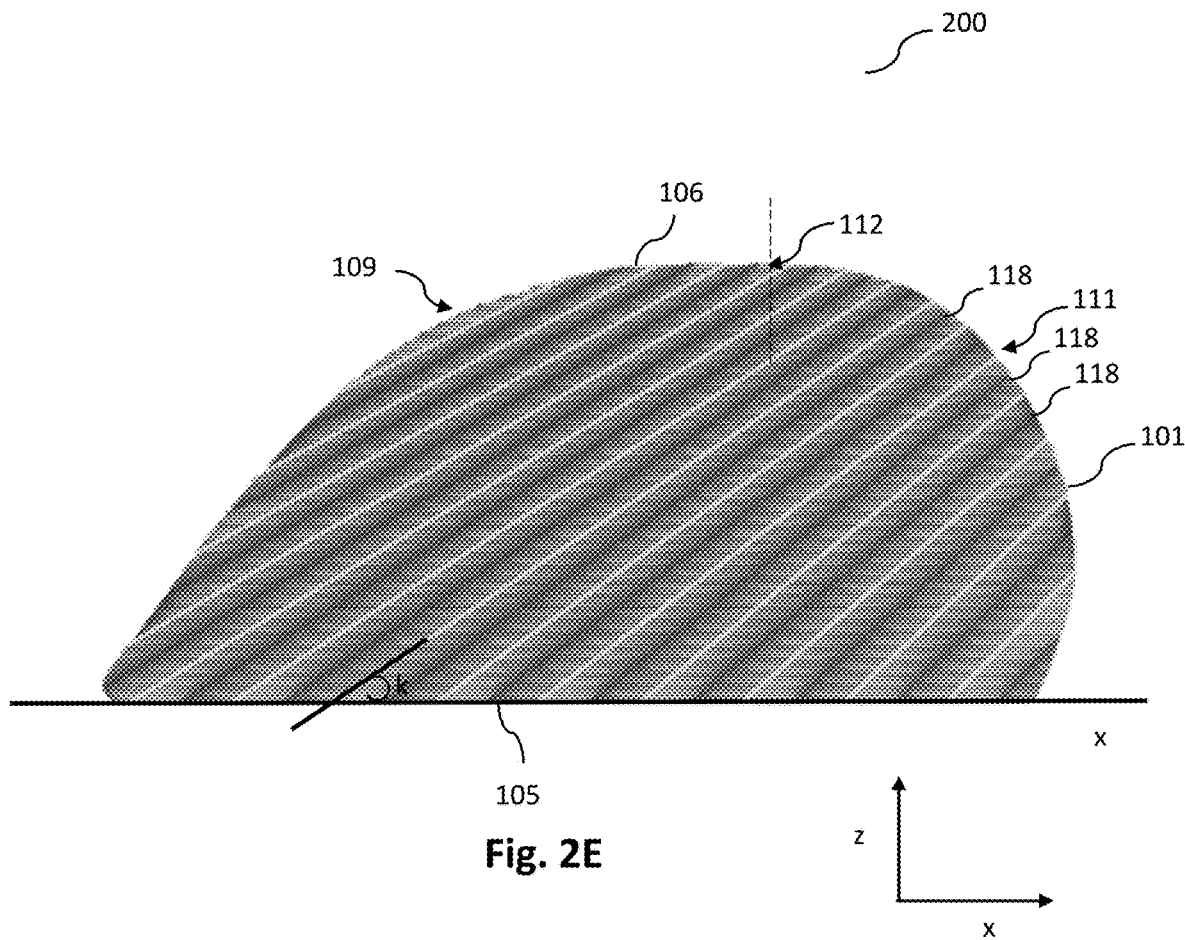
FIG. 2E shows a cross-sectional longitudinal side view of an implant.

FIG. 2E shows a cross-sectional longitudinal (side view) of the first outer surface region 105 of the implant 200. The cross-sectional side view illustration shows that the individual layers of the arrangement of layers may be configured so that the (two-dimensional) unit cells of the successive layers may form a plurality of hollow channels 118 extending between the first outer surface region 105 and the second outer surface region 106 of the three-dimensional structure 101. The cross-sectional side view illustration shows the plurality of hollow channels 118 formed by the arrangement of the two-dimensional unit cells of the successive layers within the implant 200.

One or more channels 118 of the plurality of hollow channels may be configured to extend from the first outer surface region 105 towards the apex region 112 of the second outer surface region 106 and/or the lower pole portion 111 of the second outer surface region 106. Additionally, or optionally, one or more further channels 118 of the plurality of hollow channels may be configured to extend from an upper pole portion 109 of the second outer surface region 106 towards the apex region 112 and/or the lower pole portion 111 of the second outer surface region 106. Optionally, the plurality of hollow channels may be parallel to each other (e.g. an acute angle between the sidewalls of adjacent channels may lie within +/−5°). Alternatively, the plurality of hollow channels may converge towards a region (or point) of convergence, wherein the region of convergence is located outside the first outer surface region 105 or the second outer surface region 106 of the three-dimensional structure. For example, the point of convergence may be located above the apex region 112 of the implant 200.

The plurality of hollow channels 118 may be slanted with respect to the first outer surface region 105 of the implant 200. An acute tilt angle, k, between a sidewall of a hollow channel 118 and a reference axis (e.g. an x-axis) representing the first outer surface region may be less than 90 degrees, or for example, less than 60 degrees. The reference axis may be based on a plane or line of best fit of the first outer surface region 105. The plurality of hollow channels 118 may consist of between 5 and 1000 hollow channels (or e.g. between 5 and 60 channels, or e.g. between 8 and 20 channels). Each slanted channel may be formed from (or may include) a column of unit cells from successive layers 126 stacked on top of each other. Of the unit cells forming the column of unit cells, a unit cell of a second layer may have a lateral offset (in the x-direction) with respect to a unit cell of an adjacent first layer.

A sidewall of the column of unit cells may be formed from a plurality of lateral lines (lying substantially parallel to the x-y-plane), vertically stacked in the z-direction, and oriented in the same direction, wherein the lines forming the sidewall are the lines forming the individual unit cells of the column of unit cells. For example, a column of diamond-shaped unit cells may be formed by a vertical stack of diamond-shaped unit cells, wherein the lines or walls enclosing (and defining) an individual unit cell in a layer 126 may be aligned with the lines or walls enclosing (and defining) a subsequent unit cell of a subsequent layer. Thus, the walls of each unit cell of the column of unit cells may form at least part of the sidewall of the column of unit cells. The individual unit cells of the column of unit cells may be aligned so that within the same column, a unit cell of each successive layer may have a lateral offset with respect to a unit cell of a (directly) previous layer. The lateral offset value between the first unit cell and the second unit cell may lie between 0% and 50% (or e.g. between 0% and 20%, or e.g. between 5% and 10%) of a pore size of the unit cell. Optionally, within the same column, a unit cell of each layer may have the same lateral offset with respect to a unit cell of a directly previous layer. Optionally, at least (e.g. equal to or larger than) 80% (or e.g. at least 70%, or e.g. at least 50%) of the unit cells of the same column (forming the same channel) may have the same pore size and the same pore shape. Alternatively, in the case of tapered channels, unit cells forming the same channel may have different pore sizes (e.g. the pore sizes of the unit cells may decrease or increase towards one of the outer surface regions). Surface porosity and the different sizes of surface pores are shown in FIGS. 2F and 2G.

Figure 2F:
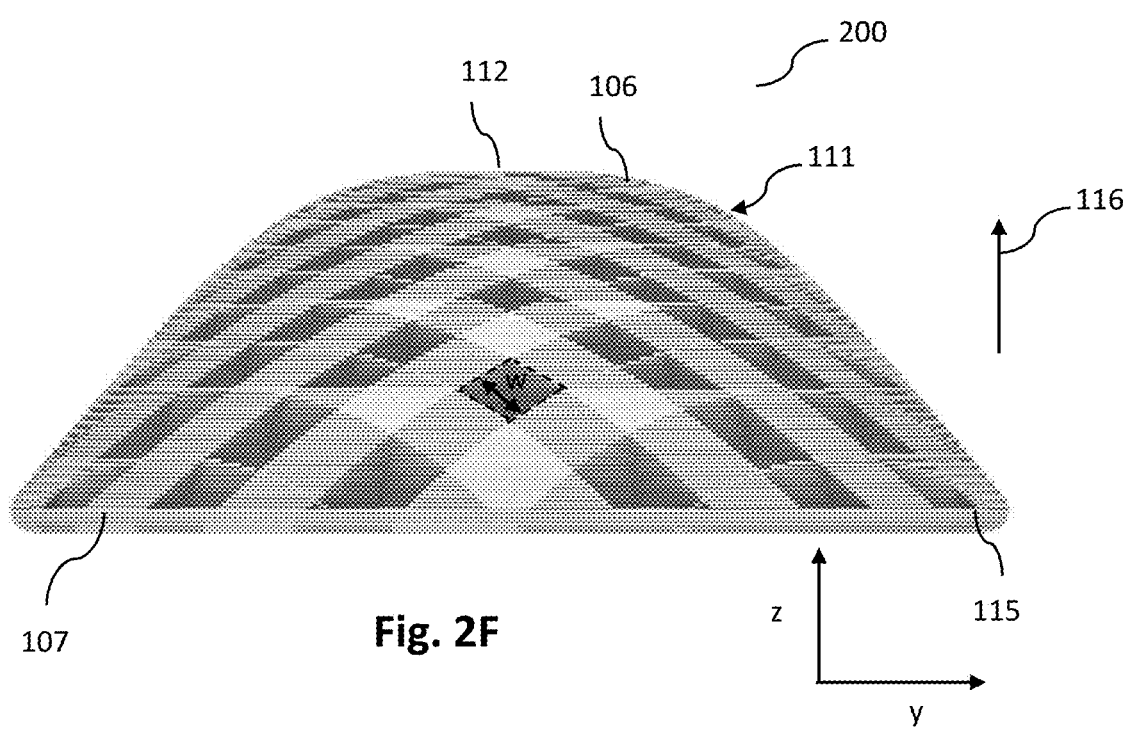
FIG. 2F shows a perspective side view illustration of a lower pole portion of a second outer surface region of an implant.

FIG. 2F shows a perspective side view illustration of the lower pole portion 111 of the second outer surface region.

As shown in FIG. 2F and FIG. 2A, a surface pore size, w, at the lower pole portion 111 of the second outer surface region 106 may increase (gradually, or e.g. step-wise, or e.g. layer-wise) from the lower pole interface region 115 towards the apex region 112 of the second outer surface region 106. The lower pole interface region 115 may be an interface (or edge) region of the three-dimensional structure 101 at which the lower pole portion 111 of the second outer surface region 106 meets a portion of the perimeter 107 of the first outer surface region 105. The surface pore size at the lower pole portion 111 of the second outer surface region 106 may increase from 0.15 mm or 2 mm at the lower pole interface region 115 up to 6 mm, up to 8 mm or up to 9 mm, or up to 10 mm towards the apex region 112 of the second outer surface region 106, for example. The direction of increase is denoted by arrow 116. Optionally, the surface pore size may increase from 3 mm to 7 mm (or e.g. from 3 mm to 6 mm, or from 4 mm to 8 mm, as in the implant used in the Experimental Example of the present application).

Figure 2G:
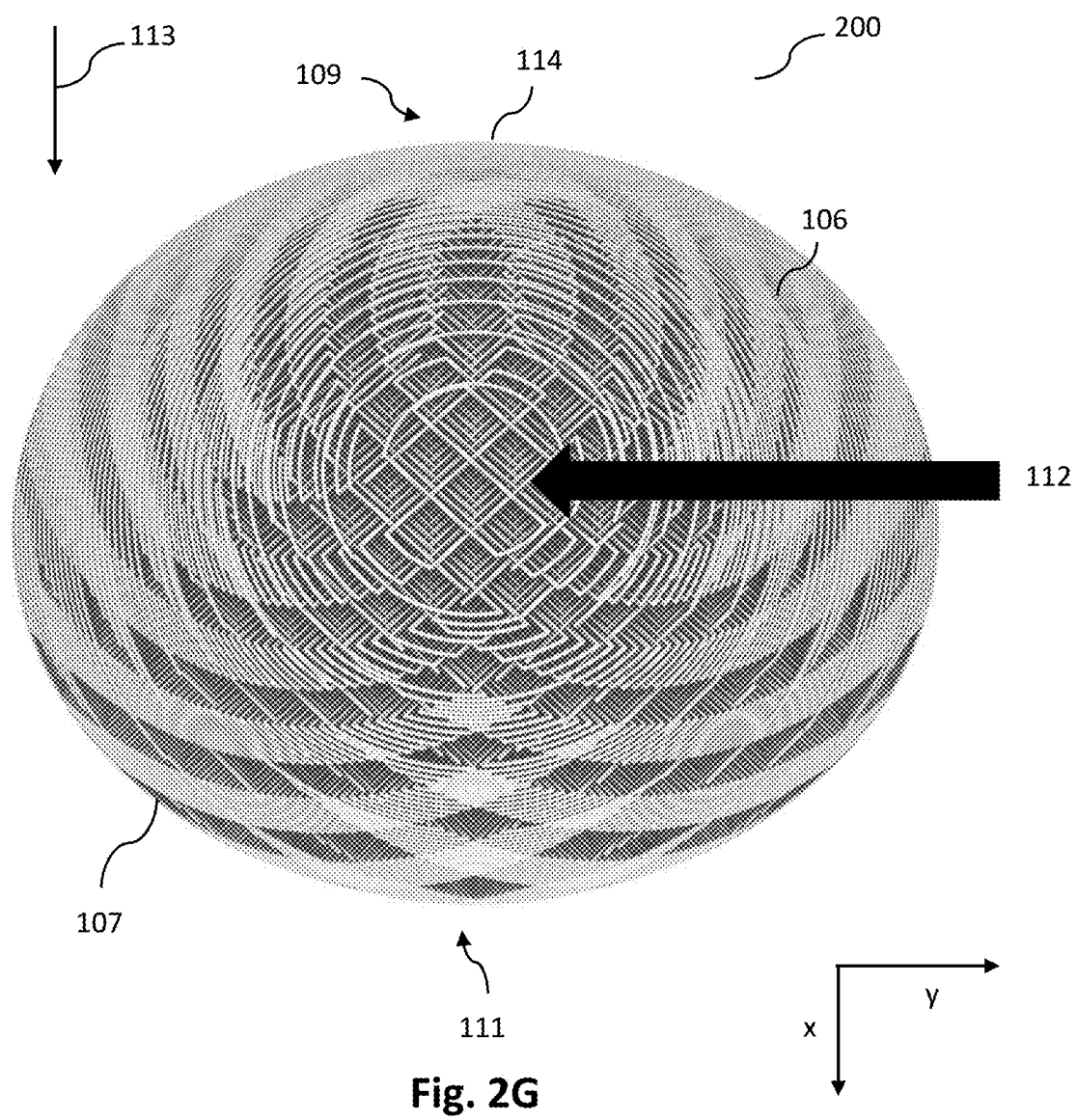
FIG. 2G a perspective top view illustration (plan view) illustration of a second outer surface region of an implant.

FIG. 2G shows a perspective top view illustration of the second outer surface region 106 of the implant 200.

As shown in FIG. 2G, the apex region 112 lies between (or at an interface) between the upper pole portion 109 and the lower pole portion 111. As shown in FIG. 2G (and FIG. 2A), additionally or optionally, the (average) surface pore sizes at the first outer surface region 105 may be larger than the (average) surface pore sizes at the upper pole portion 109. A surface pore size at the upper pole portion 109 of the second outer surface region 106 may increase (gradually, or e.g. step-wise, or e.g. layer-wise) from an upper pole interface region 114 towards the apex region 112 of the second outer surface region 106. The direction of increase is denoted by arrow 113. The upper pole interface region 114 may be an interface (or edge) region of the three-dimensional structure 101 at which the upper pole portion 109 of the second outer surface region 106 meets a portion of the perimeter 107 of the first outer surface region 105. For example, the surface pore size at the upper pole portion 109 of the second outer surface region 106 may increase from 0.5 mm at an upper pole interface region 114 up to 5 mm at the apex region 112 of the second outer surface region 106. Optionally, the surface pore size may increase from 0.5 mm to 4 mm (or e.g. from 0.5 mm to 2 mm, or e.g. from 0.8 mm to 2 mm, or e.g. from 1 mm to 2 mm). The surface pore sizes at the upper pole portion 109 may be achieved by (or may depend on) a spacing between contouring lines (shown in FIGS. 4A and 4B) arranged at the upper pole portion 109 of the second outer surface region 106.

An average surface pore size, w, of surface pores at (or within) the apex region may range from 2 mm to 6 mm (or e.g. from 2 mm to 4 mm, or e.g. from 2 mm to 3 mm).

Generally speaking, a surface pore size of at least 50% (or e.g. at least 70%, or e.g. at least 80%) of the three-dimensional structure 101 may be at least 0.5 mm (or e.g. at least 0.75 mm, or e.g. at least 1 mm). An average surface pore size of the three-dimensional structure 101 may be at least 0.5 mm (or e.g. at least 0.75 mm, or e.g. at least 1 mm). The average surface pore size may be calculated by adding the pore sizes of a total number of openings at the outermost surfaces of the three-dimensional structure 101, and dividing by the total number of openings at the outermost surfaces of the three-dimensional structure. A surface pore area of at least 50% (or e.g. at least 70%, or e.g. at least 80%) of the surface pores of the three-dimensional structure 101 may be at least 0.75 mm$^2$ (or e.g. at least 1 mm$^2$, or e.g. at least 3 mm$^2$). The surface pore area may be the area enclosed by intersecting lines defining a surface pore.

Optionally, the pore sizes of the unit cells 102 within a layer may vary from each other. For example, in the case of tapering channels, or converging channels, the unit cells within a layer may have the same shape, but may have different pore sizes. Thus, the pore sizes of the unit cells at different locations of the implant 200 may differ from each other. For example, the pore sizes of the unit cells 102 within the bulk of the implant 200 (bulk pore size) may vary from each other depending on the location of the unit cells 102 within the implant 200.

Figure 3A:
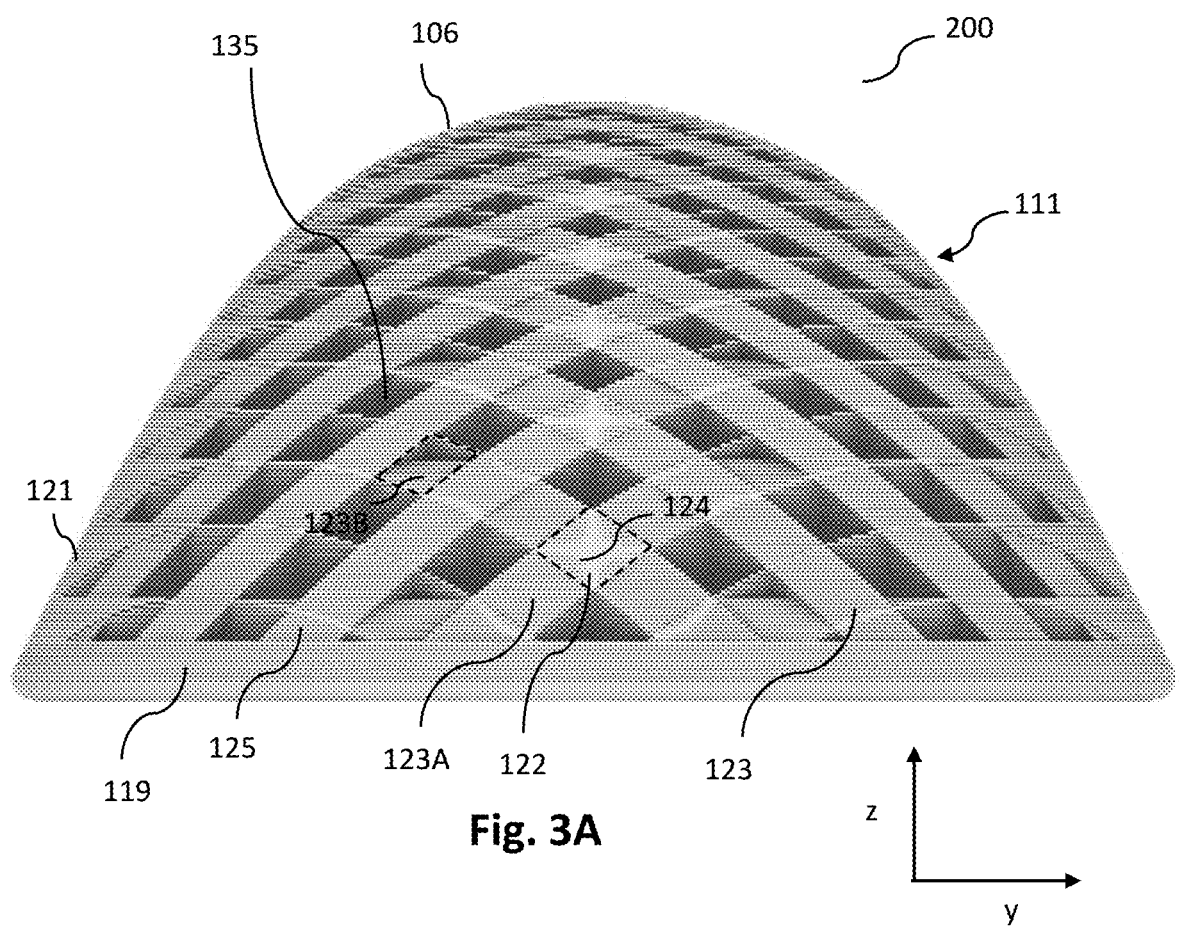
FIG. 3A shows a perspective side view illustration of an implant having a plurality of surface filler portions.

FIG. 3A shows a perspective side view three-dimensional illustration of the implant 200 having a plurality of surface filler portions 122. The illustration shows a side view of the lower pole portion 111 of the implant 200. The implant 200 may include one or more or all of the features described in connection with FIGS. 1B to 2G, and various other features.

A surface filler portion 122 may occupy an opening (surface pore) at the outermost surface of the three-dimensional structure 101. Each surface filler portion 122 may include one or more filler lines 124 configured to at least partially fill one or more openings (surface pores) at the outermost surface of the three-dimensional structure 101. The one or more filler lines 124 of the surface filler portions 122 may be configured to connect (or a least partially fill the spaces between) a group of intersecting lines defining the surface pores 123 at the outer surface regions of the three-dimensional structure. An at least partially filled surface pore may be a surface pore wherein filler lines occupy between 50% and 99% (or e.g. between 55% and 95%, or e.g. between 80% and 95%) of the surface area of the pore. For example, both pores 123A and 123B may be considered to be at least partially filled even though a larger percentage of the surface area of pore 123A is filled than pore 123B. Optionally, at least 20% (or e.g. at least 30%, or e.g. at least 40%) of the surface pores at the outer surface region of the three-dimensional structure 101 may be at least partially filled with surface filler portions 122. Optionally, the surface filler portions 122 may be formed (or arranged) at the second outer surface region, whereas the first outer surface region may be free for surface filler portions 122 (e.g. all surface pores at the first outer surface region may be open)

Figure 3B:
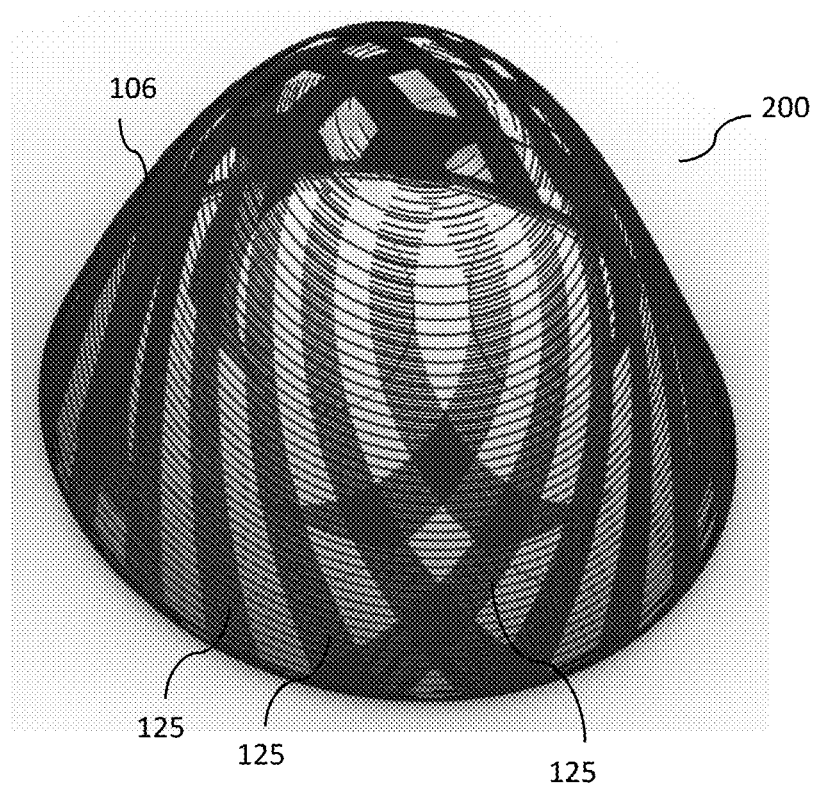
FIG. 3B shows a perspective side and top view illustration of an implant comprising surface filler columns.

FIG. 3B shows a perspective side and top view illustration of the implant 200 comprising surface filler columns 125. The illustration shows a surface porosity of the implant 200.

Optionally a ratio of filled surface pores (closed surface pores) to non-filled (open surface pores) at the second outer surface region may be 1:2. In this manner, a surface porosity of the implant 200 before insertion into the patient may be defined. A surface porosity may represent (or may be) a void fraction or percentage (e.g. a measure of the empty space) of the outermost surface of the three-dimensional structure 101. The surface porosity of the implant 200 may be determined by the total void space ($m^2$) at the outermost surface (e.g. the total surface area of unfilled openings at the outermost surface of the 3D structure 101) divided by the total surface area ($m^2$) of the 3D structure 101 of the implant 200. A surface porosity of the second outer surface region may be less than a bulk porosity of the three-dimensional structure of the implant. The surface porosity of the second outer surface region may be less than (e.g. 0.8 times, or e.g. 0.5 times, or e.g. 0.2 times, or e.g. 0.1 times) a surface porosity of the first outer surface region. For example, a surface porosity of the second outer surface of the implant 200 may lie between 30% and 80% (or e.g. between 40% and 70%, or e.g. between 50% and 60%, or e.g. between 54% and 66%). A bulk porosity of the three-dimensional structure 101 of the implant 200 may be at least 80% (or e.g. at least 20%, or e.g. at least 50%, or e.g. at least 60%, or e.g. at least 70%, or e.g. at least 85%, or e.g. at least 90%). Optionally a bulk porosity of the implant may lie between 80% and 99%. The bulk porosity may represent (or may be) a void fraction or percentage (e.g. a measure of the empty space) of the implant 200 before insertion into the patient.

The bulk porosity of the implant 200 may be determined by the total void space ($m^3$) within the implant divided by the total volume ($m^3$) of the 3D structure 101 of the implant 200.

The compressibility of the three-dimensional structure 101 of the implant may be based on (or e.g. proportional to) the bulk porosity and/or total void space of the implant. For example, the three-dimensional structure 101 may be compressible to a minimal compressible volume, $V_C$ based on (or e.g. proportional to) the void space of the implant. For example, the three-dimension may be compressible to $Vc=V_T-V_V$ wherein $V_C$ is the volume of the compressed implant, $V_V$ is the volume of void-space, and $V_T$ is the total resting volume of the scaffold. In other words, the implant may be compressed by a volume based on (proportional to, or equal to) the volume of void space.

The spring-like implants may be configured to recover at least 80% (e.g. equal to or larger than 80%) (or e.g. at least 90%, or e.g. at least 95%, or e.g. at least 98%, or e.g. up to 100%) of its original volume, after the compression force exerted on the implant is removed.

The amount of recovery of the spring-like implant may depend on the amount of compression exerted on the implant. For example, the implant may be compressed in at least one direction of compression to 30% or smaller of a dimension. After the force is removed, the scaffold 101 may recover (spring-back) to 80% or more of the dimension. Alternatively, implant may be compressed to 80% or less of a dimension. After the force is removed, the scaffold 101 may recover to 85% or 90% or more of the initial projection.

Additionally, the implant 100, 200 may be reversibly compressible in one or more axial directions (e.g. in two axial directions such as the x-y directions, or e.g. in three axial directions such as the x-y-z directions) simultaneously. Thus, the implant may be compressible to 80% or smaller (or e.g. 70% or smaller, or e.g. 60% or smaller, or e.g. 50% or smaller, or e.g. 30% or smaller, or e.g. 20% or smaller, or e.g. 10% or smaller) of its original dimensions in each of the one or more axial directions (e.g. height, width, length, and/or projection). The implant may be configured to recover to 80% or more (e.g. 90% or more, or e.g. 95% or more, or e.g. 98% or more, or e.g. 100%) of the original dimensions in each of the one or two or three axial directions.

Optionally the plurality of surface filler portions may be arranged to form a plurality of surface filler columns 125 (or strips) at the second outer surface region 106. A surface filler column 125 may include a plurality of surface filler portions occupying a column of adjacent surface pores (e.g. openings). A surface filler column may be arranged adjacent to an open column 135. An open column 135 may include (or may be) a column of surface pores that are free from surface filler portions. Optionally, a plurality of surface filler columns 125 and a plurality of open columns 135 may be arranged alternatingly at the outer surface regions (e.g. at the second outer surface region). Optionally a plurality of surface filler columns and a plurality of open columns may be arranged in a criss-cross fashion at the outer surface regions.

A surface filler column 125 arranged at the lower pole portion of the second outer surface region may at least partially cover or close the top openings of the some of the channels of the implant 200. A surface filler column 125 arranged at the upper pole portion of the second outer surface region may include (or may form part of) a sidewall of a channel of the plurality of hollow channels.

Figure 4A:
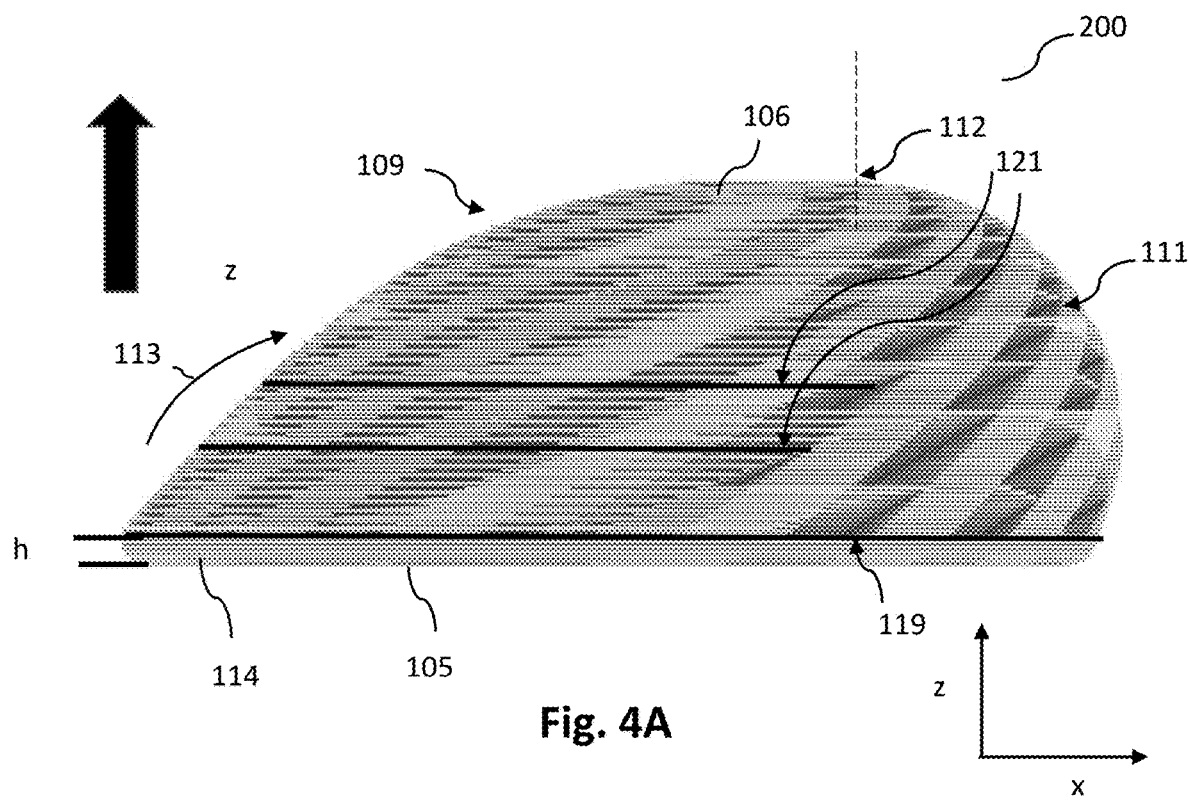
FIGS. 4A and 4B show a perspective longitudinal side view and a perspective top view illustration respectively of an implant.
Figure 4B:
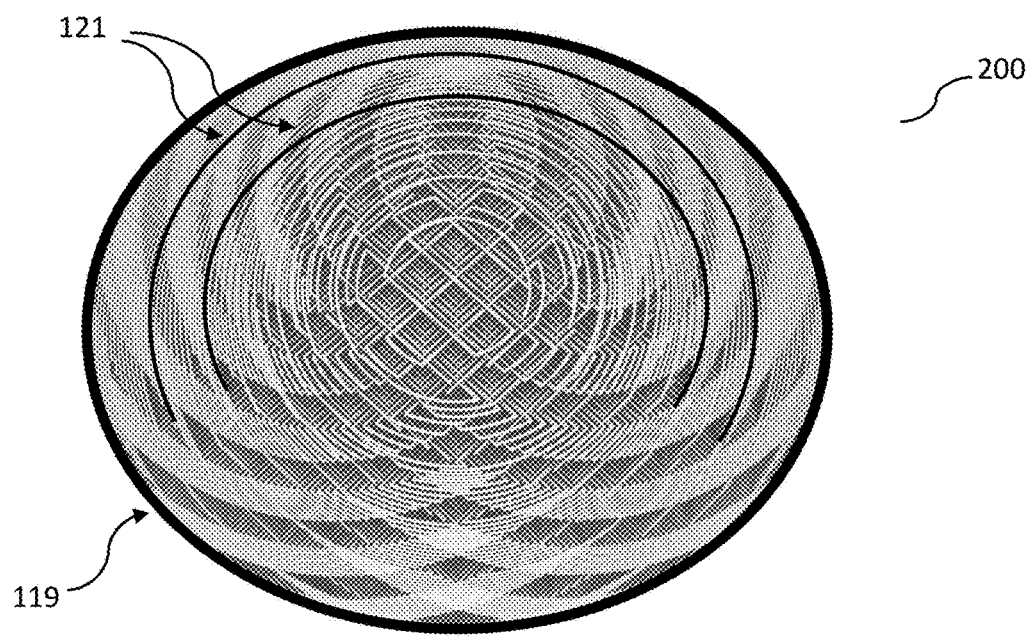

FIGS. 4A and 4B show a longitudinal side view and top view illustration respectively of the implant 200. The implant 200 may include one or more or all of the features described in connection with FIGS. 1B to 3B, and various other features.

As shown in FIGS. 4A and 4B, the plurality of lines forming the three-dimensional structure 101 of the implant 200 may include a plurality of contouring lines. A first group 119 of contouring lines of the plurality of lines may be arranged around the perimeter 107 of the first outer surface region 105 (or e.g. around the perimeter 107 of one or more layers at the first outer surface region 105. The first group 119 of contouring lines may be arranged fully (e.g. at least 90%, or e.g. at least 95%, or e.g. at least 99%, or e.g. 100%) around the perimeter 107 of the first outer surface region 105, e.g. forming a closed circle, or closed ellipse. The first group of contouring lines 119 may consist of between 2 contouring lines to 20 contouring lines, for example. The contouring lines of the first group of contouring lines 119 may be formed successively (consecutively) in a direction from the first outer surface region 105 towards the apex region 112 (e.g. in the z-direction). Optionally, a thickness or height, h, (measured in a vertical, z-direction) of the first group of contouring lines may range from 1 mm to 20 mm (or e.g. from 2 mm to 10 mm, or e.g. from 1.5 mm to 5 mm).

The plurality of lines forming the three-dimensional structure 101 of the implant 200 may further include a second group 121 of contouring lines. Unlike the first group of contouring lines 119 forming a full contour around the perimeter 107 of the first outer surface region, each contouring line of the second group of contouring lines 121 may form a semi-contour around the second outer surface region. The semi-contour of the second group of contouring lines 121 may extend only partially (e.g. between 30% and 80%, or e.g. between 40% and 70%, or e.g. between 50% and 70%) around the perimeter of a layer. For example, the second group of contouring lines 121 may be arranged at (or e.g. around) an upper pole portion 109 of the second outer surface region 106, and a lower pole portion 111 of the second outer surface region 106 may be free of (may not have) contouring lines. The second group of contouring lines 121 may be arranged successively with respect to each other between the first outer surface region and the apex region. Optionally, the second group of contouring lines 121 are not necessarily formed at the perimeter of every lateral layer, but at every alternate layer, or at every alternate group of layers.

Optionally, the surface pore sizes of the openings at the surface of the upper pole portion 109 may be determined by the vertical spacing between consecutive (directly adjacent) contouring lines of the second group of contouring lines 121. For example, a vertical spacing between consecutive contouring lines of the second group of contouring lines may range from (or e.g. increase from) 0.5 mm at an upper pole interface region 114 up to 5 mm at the apex region 112 of the second outer surface region 106. As with the increase in pore size direction, the direction of increase is denoted by arrow 113. Optionally the vertical spacing between consecutive contouring lines of the second group of contouring lines may increase from 0.5 mm to 4 mm (or e.g. from 0.5 mm to 2 mm).

The three-dimensional structure 101 of the implant 200 may be formed from a surface-degradable polymer. A surface-degradable polymer material may be a polymer material that degrades predominantly via the surface degradation mechanism as opposed to bulk degradation. For example, surface degradation refers to the breakdown of the exterior surface of the polymer material as opposed to the inside of the polymer material. The breakdown of the exterior surface of the polymer material may occur at least 2 times (or e.g. at least 5 times, or e.g. at least 10 times, or e.g. at least 100 times) the speed of breakdown of the interior of the polymer material. Bulk degradation refers to the degradation or break down of both the exterior surface and the interior of the material simultaneously, and at the same rate (e.g. the ratio of speed of exterior breakdown to speed of interior breakdown is less than 1.2). The surface degradable polymer may for example be a biodegradable polymer. The plurality of lines (or alternatively also all lines) may include or may be formed from or made of biodegradable material. The biodegradable material may, for example, be a material as described in International patent application WO 2016/038083. In illustrative example, the biodegradable material, may be selected from polycaprolactone, poly(1,3-trimethylene carbonate), polylactide, polyglycolide, poly(ester amide), poly(ethylene glycol)/poly(butylene terephthalate), poly(glycerol sebacate), poly(1,8-octanediol-co-citric acid), poly(1,10-decanediol-co-D,L-lactic acid), poly(diol citrate), poly(glycolide-co-caprolactone), poly(1,3-trimethylene carbonate-co-lactide), poly(1,3-trimethylene carbonate-co-caprolactone) or a copolymer of at least two of these materials. Optionally, the biodegradable material may be polycaprolactone. Optionally, the biodegradable material may be a copolymer of polycaprolactone and either poly-trimethylene carbonate or polylactide. Alternatively, the plurality of lines may include a non-degradable material such as nylon.

Figure 5:
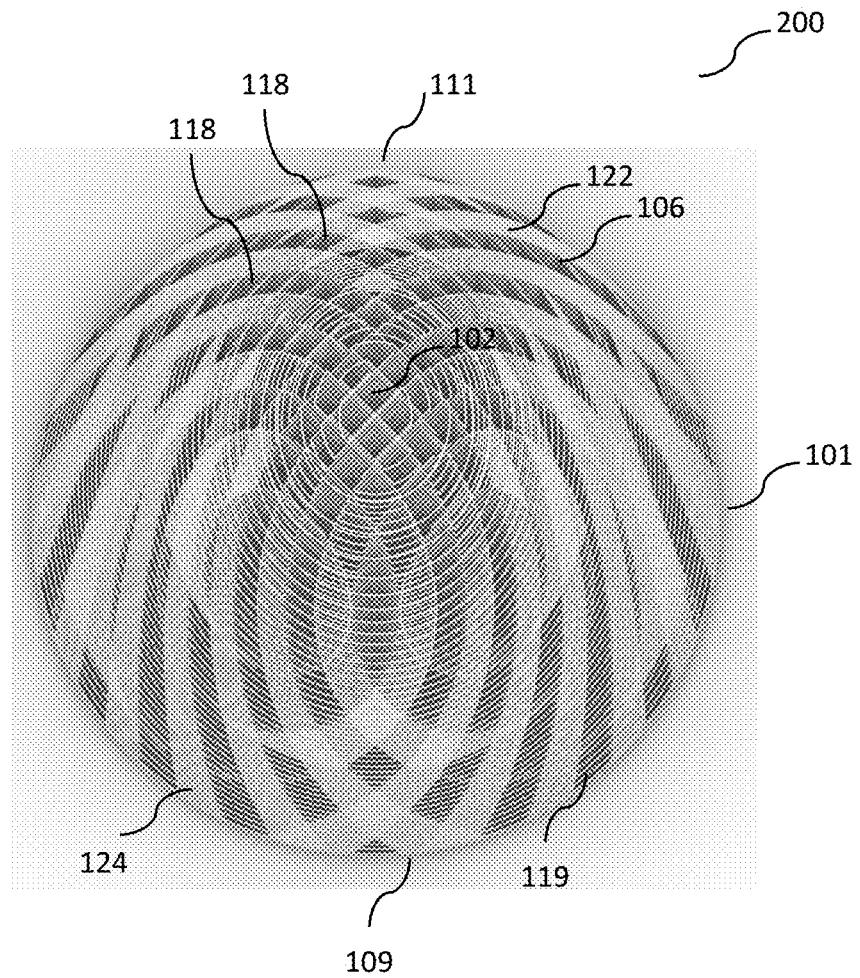
FIG. 5 shows a perspective top view illustration of an implant of the invention.

FIG. 5 shows a perspective top view illustration of the implant 200. The implant 200 may include one or more or all of the features described in connection with FIGS. 1B to 4B, and various other features.

In some embodiments, the implant 200 is an implant for insertion into a patient. The implant comprises a porous three-dimensional scaffold structure comprising an arrangement of unit cells 102, wherein a bulk porosity of the implant is at least 80%.

In some embodiments, the implant 200 comprises a porous three-dimensional scaffold structure 101 comprising an arrangement of unit cells 102. The plurality of unit cells 102 are arranged to form a porous network of the three-dimensional scaffold structure 101. An average pore size of the plurality of unit cells 102 of the three-dimensional structure 101 is at least about 0.5 mm (or e.g. at least about 0.75 mm, or e.g. at least about 0.8 mm, or e.g. at least about 1 mm, or e.g. at least about 1.5 mm, or e.g. at least about 2 mm, or e.g. at least about 5 mm).

In some embodiments, the implant 200 comprises a three-dimensional porous scaffold structure 101 including a plurality of hollow channels 118 extending between a first outer surface region (not shown in the top view) and a second outer surface region 106 of the three-dimensional porous scaffold 101. The porous scaffold structure 101 comprises a surface-degradable polymer material. The first outer surface region is configured to face a chest wall of the patient receiving the implant. A geometry of the second outer surface region represents a geometry of a breast to be constructed by the implant 200. The plurality of hollow channels 118 are configured to be aligned with Cooper's ligaments of the patient receiving the implant.

The implant 200 includes a porous three-dimensional scaffold structure 101 comprising an arrangement of unit cells 102. The illustration shows the implant 200 including the plurality of lines, the contouring lines 119 and the surface filler portions 122, for example. The implant 200 may include a porous three-dimensional scaffold comprising an arrangement of unit cells. The plurality of unit cells 102 are arranged to form a porous network of the three-dimensional structure. A pore size of the plurality of unit cells 102 of the three-dimensional structure may be at least 0.5 mm.

The plurality of lines (e.g. the intersecting lines, the contouring lines, the surface filler lines) may include a degradable (e.g. a surface degradable) polymer material.

The mechanical challenges from daily activities may exceed the elastic capacity of the breast tissue, and may eventually lead to irreversible tissue stretching directly proportional to the introduced mass. Contrary to long-standing dogmas, implant weight rather than its volume, may stand at the basis of future tissue compromise and deformation. For example, the elastic tissue of the breast may be symbolized by a spring with constant K. In a static, upright posture, the weight of an implant may displace the breast downwards with a force proportional to the weight of the implant, as described by the following formula: F=m×g, where F is the force, m is the mass, and g is the standard gravity constant. The tissue's stretch may be linear (within the elasticity limits of the tissue), and, therefore, tissue displacement may increase in direct correlation with implant weight. The displacement is described as Δx=F/K, where Δx is the displacement, F is the force applied, and K is the spring constant. Traditional heavier implants may result in increased forces and consequential stretch of the breast, as compared with a lighter implant. The implant 200, being a lightweight implant may reduce deformation and the extent of breast tissue being compromised, this may reduce subsequent reoperations, thereby further improving patient safety and satisfaction.

To alleviate the problem of the weight affecting the shape of the outcome, the implant 200 may include a low-density scaffold, so that for the same volume, the weight of the implant 200 may be reduced and as a consequence the force acting on the breast may be reduced as well. The weight (mass) of the scaffold may be described by the following formula:

$$m = \rho * V$$

where m is the mass of the scaffold, ρ is the density of the scaffold, and V is the volume of the scaffold.

The implant 200 may include a low-density scaffold and highly porous scaffold. Bulk (or overall) porosity of an implant of the invention may be described by the following formula:

$$\text{Porosity} = \frac{V_V}{V_T}$$

where $V_V$ is the volume of void-space, and $V_T$ is the total volume of the scaffold.

Therefore, the volume of the scaffold may be expressed as $$V = V_T - V_V$$

The bulk (or overall) porosity of the implant (scaffold) may be at least at least 80%, or at least 85%, or at least 90% or at least 95%. A material density, ρ, of the implant 200 may lie between 0.1 gr/cm³ and 2 gr/cm³. (or e.g. between 0.1 gr/cm³ and 1 gr/cm³, or e.g. between 0.1 gr/cm³ and 0.5 gr/cm³). The material density may be determined by the weight of the implant 200 divided by the resting volume of the implant before insertion into the patient. In comparison, the material density of silicone is 0.98 gr/cm³, and the material density of saline is 1.005 gr/cm³. Thus, the weight of the implant of 200 may be at least 10 times less than its volume value in milliliters, and at least 10 times less than that of traditional non-porous silicone/saline implants (whose weights in grams are roughly the same as their volume value in milliliters). As an example, an implant 200 having a volume of 250 ml may weigh 25 g, whereas a traditional silicone implant having a volume of 250 ml, may weight 240 g, and a saline implant having a volume of 250 ml, may weigh 250 g. One or more or all of these features leads to an implant having a lightweight scaffold, wherein a weight reduction of 90% compared to traditional implants may be achieved.

Figure 6A:
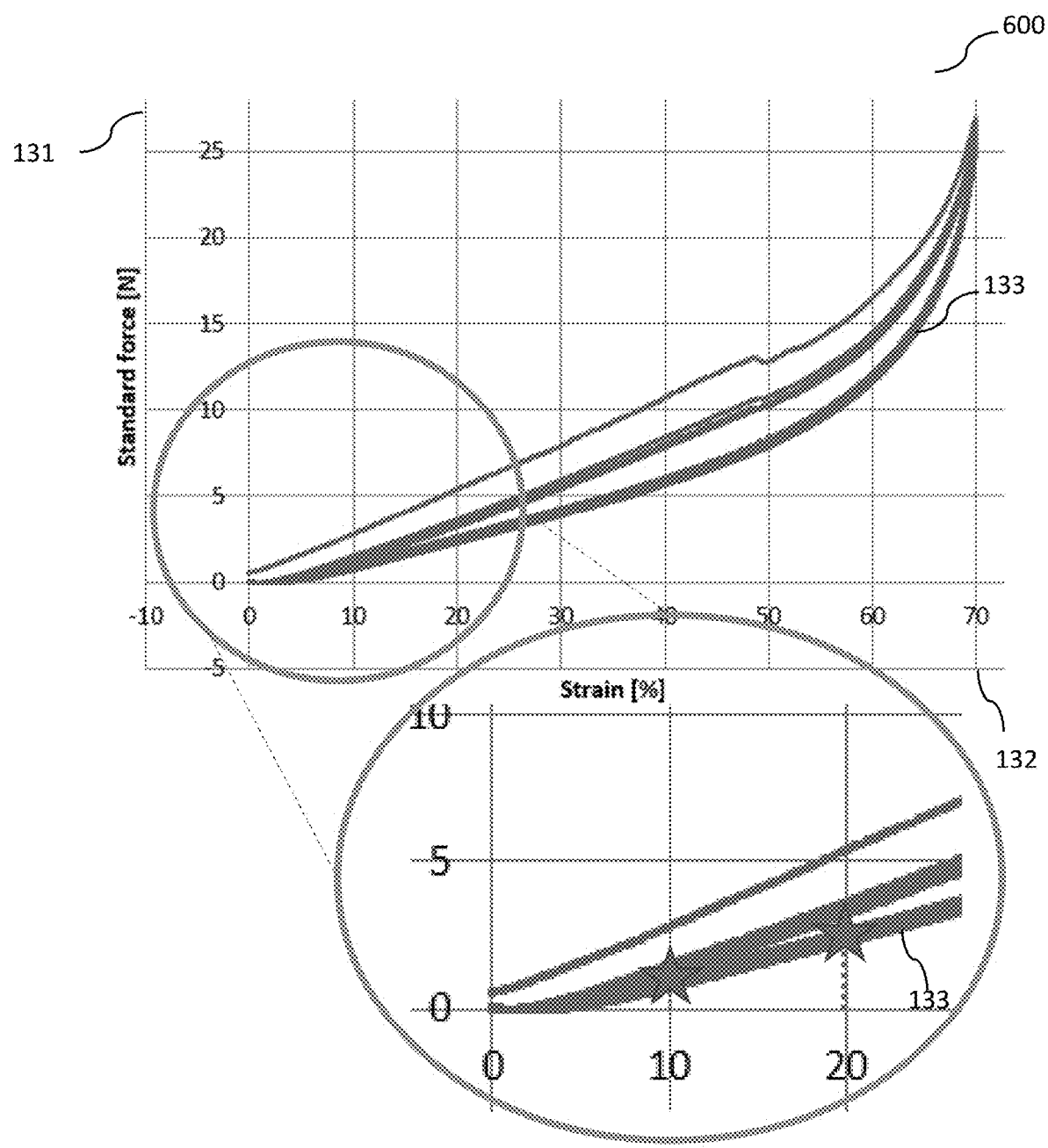
FIG. 6A shows a graphical illustration of the expression of a c-value representing a softness of an implant.

FIG. 6A shows a graphical illustration 600 of the expression of a c-value representing a softness of the implant 200. The graphical illustration shows a chart of Force (N) 131 vs strain value, ε (%) 132, at various levels of compression applied to the implant 200.

The c-value may be expressed by the formula $$c = \frac{F_{20\%} - F_{10\%}}{\varepsilon_{20\%} - \varepsilon_{10\%}}$$

$F_{20}\%$ is the force value, in N, at a compression of 20%,
$F_{10}\%$ is the force value, in N, at a compression of 10%,
$\varepsilon_{10}\%$ is the strain value at a compression of 10%,
$\varepsilon_{20}\%$ is the strain value at a compression of 20%, As shown in FIG. 6A, the implant 200 may have a c-value which is lower (i.e. the implant is softer) than other implants without the plurality of spring-like unit cells of implant 200. The c-value representing a softness of the implant 200 may lie between 20 N and 200 N (e.g. between 20 N and 150 N, or e.g. between 20 N and 90 N or e.g. between 30 N and 90 N, or e.g. between 50 N and 90 N), for example. A c-value of between 20 N and 90 N is a good window for balancing the mechanical integrity with patient comfort. The softness of the implant may be controlled to prevent deformation by skin tension during wound healing processes. For example, if the implant were too soft (e.g. having a c-value less than 20 N), the implant 200 may be more susceptible to deformation.

Figure 6B:
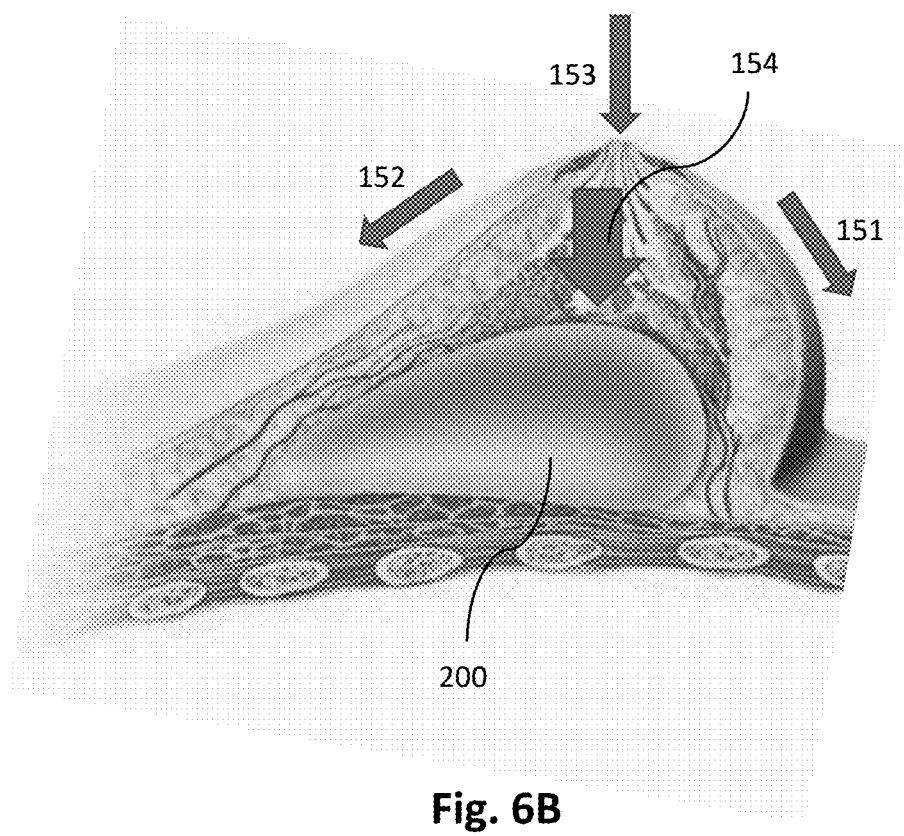
FIG. 6B shows an illustration of forces acting on an implant.

FIG. 6B shows an illustration of forces acting on the implant 200.

After insertion (or implantation) into the patient, the implant 200 may be in direct contact with the skin and breast tissue. The combined effect of tension of the skin 151, 152, the weight of the breast tissue overlapping the implant, and daily activities 153 (for example due to the lady sleeping on her belly) may cause a compression force 154 acting on the direction of projection of the implant 200 and, as a consequence lead to deformation of the implant.

Figure 6C:
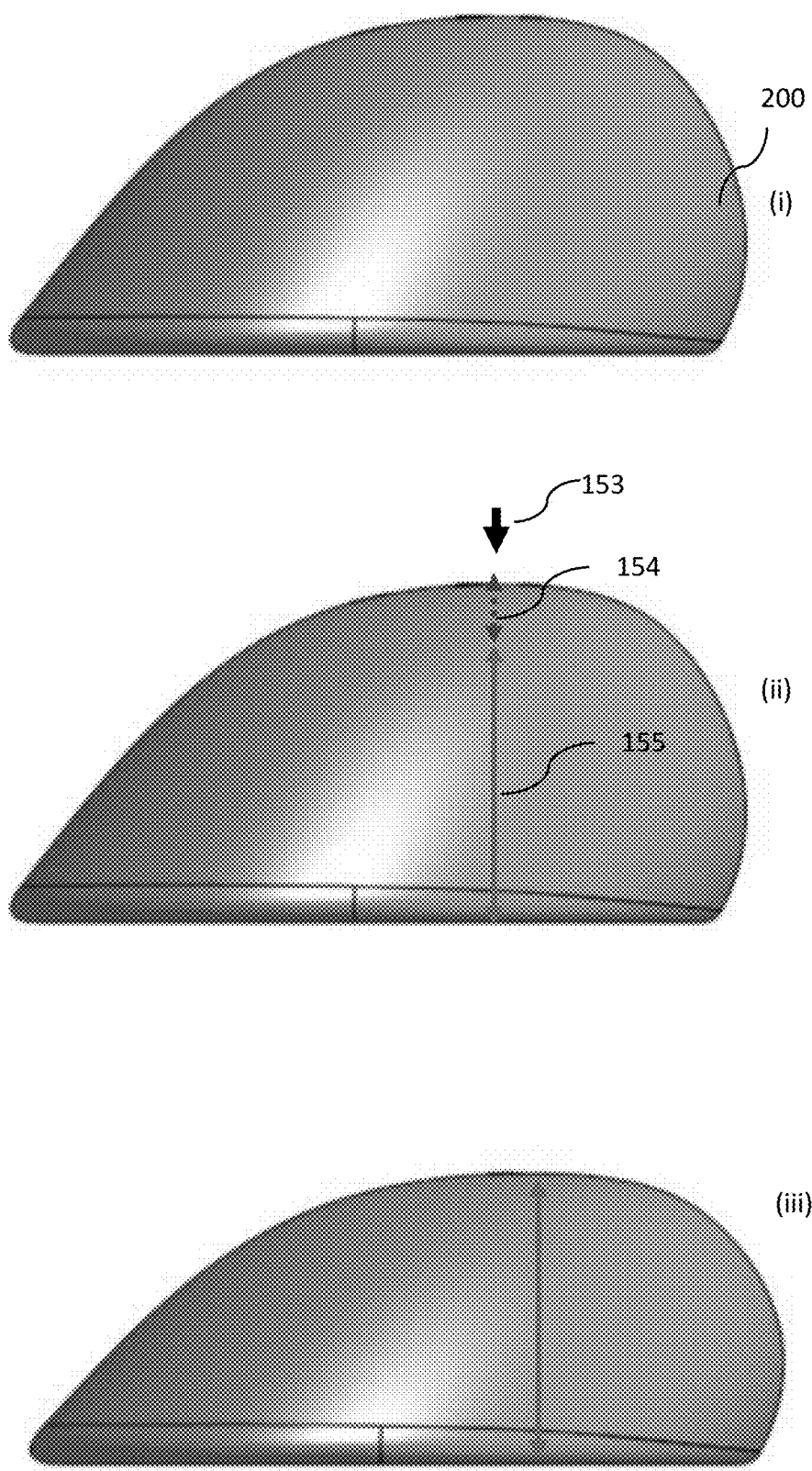
FIG. 6C (i) to (iii) shows the compressibility of an implant and overestimation of the volume of an implant.

FIG. 6C (i-iii) shows the compressibility of the implant 200 and overestimation of the volume of the implant 200.

FIG. 6c(i) shows that the implant 200 may have a resting volume or initial shape before insertion into the patient.

FIG. 6C (ii) shows the overestimation 154 of the volume of the implant 200 over the construction volume. Since the implant 200 may be a collapsible 3D printed structure, the effect of the constant compression force acting due to skin tension and tissue weight on the implant may cause a permanent volume loss before reaching the stability. To ensure that the volume requested corresponds to the actual augmented/reconstructed breast volume, the volume of the implant may be overestimated (to the resting volume) in order to take into account the initial squishing due to the effect of skin tension and tissue weight. For example, the overestimation 154 of the volume may be 20% to 30% of the projection volume (construction volume) 155 of the implant.

FIG. 6C (iii) shows the volume of the implant 200 after insertion into the patient, wherein due to the effect of skin tension, the volume of the implant corresponds to the original requested volume (construction volume).

Figure 6D:
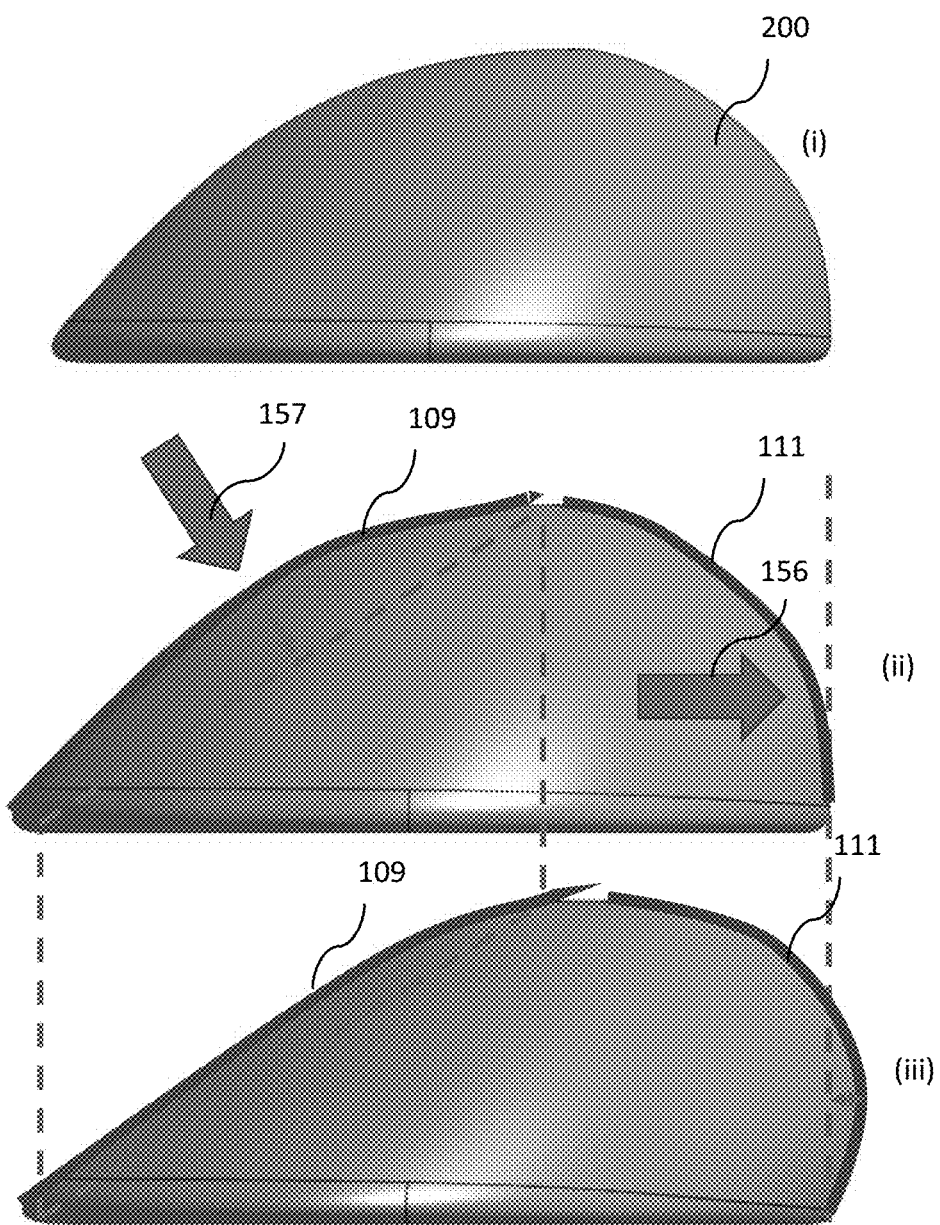
FIGS. 6D (i) to (iii) shows the effect of skin tension on the shape of an implant after insertion into a patient.

FIGS. 6D (i) to (iii) shows the effect of skin tension on the shape of the implant 200 after insertion into the patient.

FIG. 6D (i) shows that the implant 200 may have a resting volume or initial shape before insertion into the patient.

FIG. 6D (ii) shows the effect of skin tension on the implant 200. To reduce the effect of the skin tension on the projection of the scaffold, the implant 200 has been configured such that when the tension occurs, the upper pole side 109 may be compressed (or squished) first (in direction 157) resulting in a smooth transition between the chest wall and the nipple, and the lower pole side may provide the drooping effect of a natural breast (in the direction 156). Both these features contribute to confer the scaffold attaining its construction volume and the requested aesthetic and natural shape.

FIG. 6D (iii) shows the implant 200 after insertion into the patient. The implant 200 may recover a part of its original volume at least 80% (or e.g. at least 95%) of its original volume, after being compressed during the insertion of the implant 200 into the patient. The implant 200 may thus attain the desired construction volume and shape (e.g. an ideal natural shape) under the skin with the compressed upper pole side 109 and a drooping lower pole side 111.

Figure 7A:
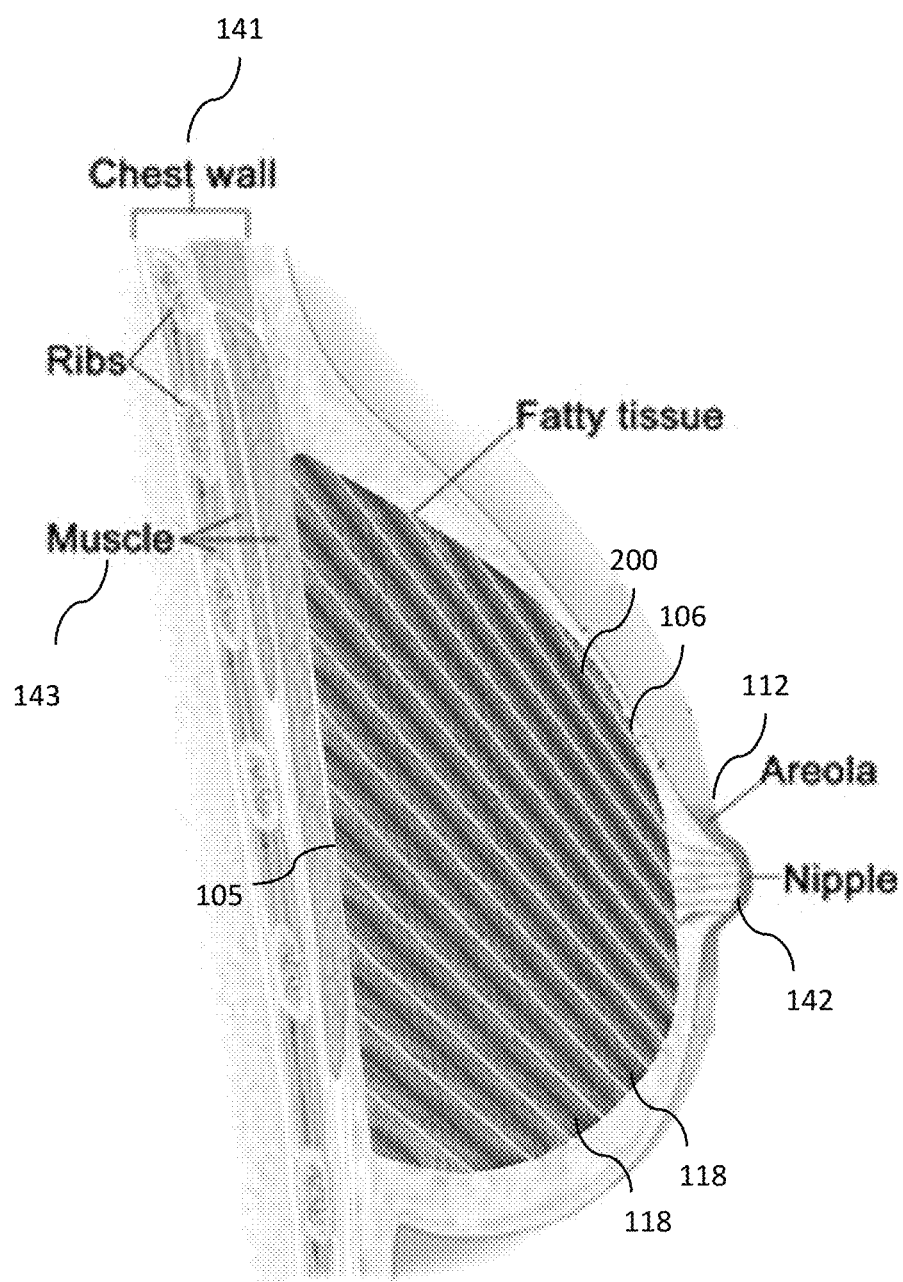
FIG. 7A shows an illustration of an implant after insertion into a patient.

FIG. 7A shows an illustration of an implant 200 after insertion into a patient.

The implant 200 may be configured so that the first outer surface region 105 of the implant 200 may be configured to face a chest wall 141 of the patient receiving the implant 200. Optionally, the implant 200 may be arranged so that the first outer surface region 105 faces the pectoralis muscle 143 (e.g. the implant may be arranged on top of the pectoralis muscles). The apex region 112 of the second outer surface region 106 of the implant may positioned at (or e.g. to directly face, or e.g. to be directly under) the nipple/areola of the breast to be constructed by the implant 200. The first outer surface region 105, having on average the largest surface pore sizes, may be configured to face a source of blood vessels of the patient. The fluids or blood vessels from the patient may infiltrate the porous network of the implant 200 in a direction guided by the direction of the channels 118 within the implant 200. Alternatively, it may be possible for the implant 200 to be arranged below the pectoralis muscle 143. For example, the first outer surface region 105 of the implant may be configured to face a chest wall 141 of the patient and the muscle may be arranged on the second outer surface region 106.

Figure 7B:
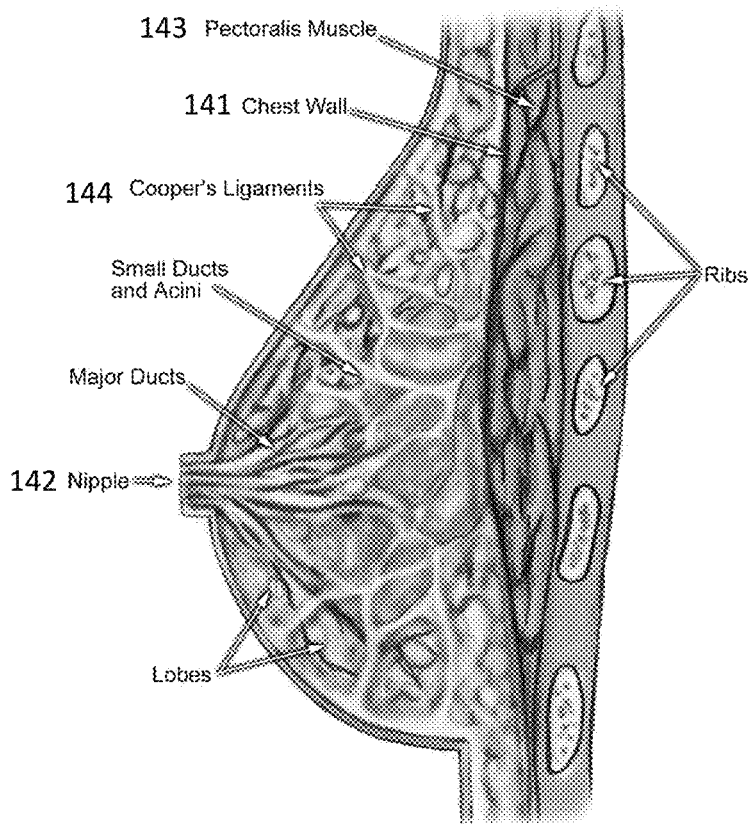
FIG. 7B shows the anatomy of a patient's breast to be constructed by an implant.

FIG. 7B shows the anatomy of a patient's breast to be constructed (e.g. breast enlargement, or e.g. breast reduction or e.g. breast revision) by the implant 200.

After the implant 200 is inserted into the patient, the scaffold (e.g. the three-dimensional structure) may be reabsorbed, and regenerated tissue may be left behind. The regenerated tissue is fibrovascular tissue and may have a similar weight to silicone implants as well as healthy tissue. The constant force acting due to the weight of the tissue may to irreversible tissue stretching. Thus, the number channels and tilt of the channels may be selected to reduce tissue stretching.

Figure 7C:
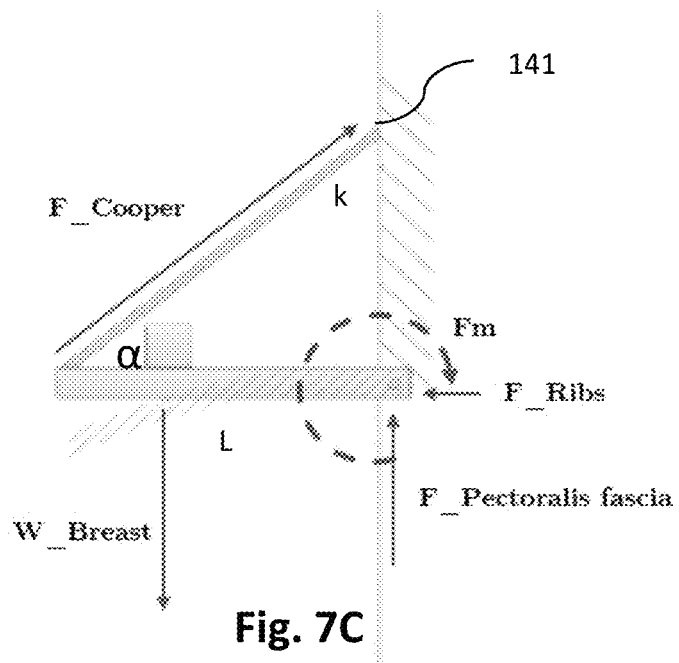
FIG. 7C shows a representation of forces acting on a breast.

FIG. 7C shows a representation of forces acting on a breast. A breast can be engineered as a hemi-ellipsoidal beam of length L. The mass of the breast generates a force aligned to gravity (W_Breast). F represent the reaction forces acting in the muscle (F_Pectoralis fascia) and ribs (F_Ribs) region, which help the system to keep the shape of the breast.

Nevertheless, an important role (e.g. the most important role) in providing support and maintaining the shape is played by the force acting in tension against gravity (F_Cooper). In young and healthy breast tissue, this effect is given by fibrous strands called suspensory or Cooper's ligaments, which emerge from the pectoralis fascia, firmly joining the breasts to the overlaying skin going through and around the breast tissue. When using a traditional silicon implant, the weight may be roughly the same as regenerated and healthy tissue but there is no such system to attach it to the pectoralis fascia.

Figure 6E:
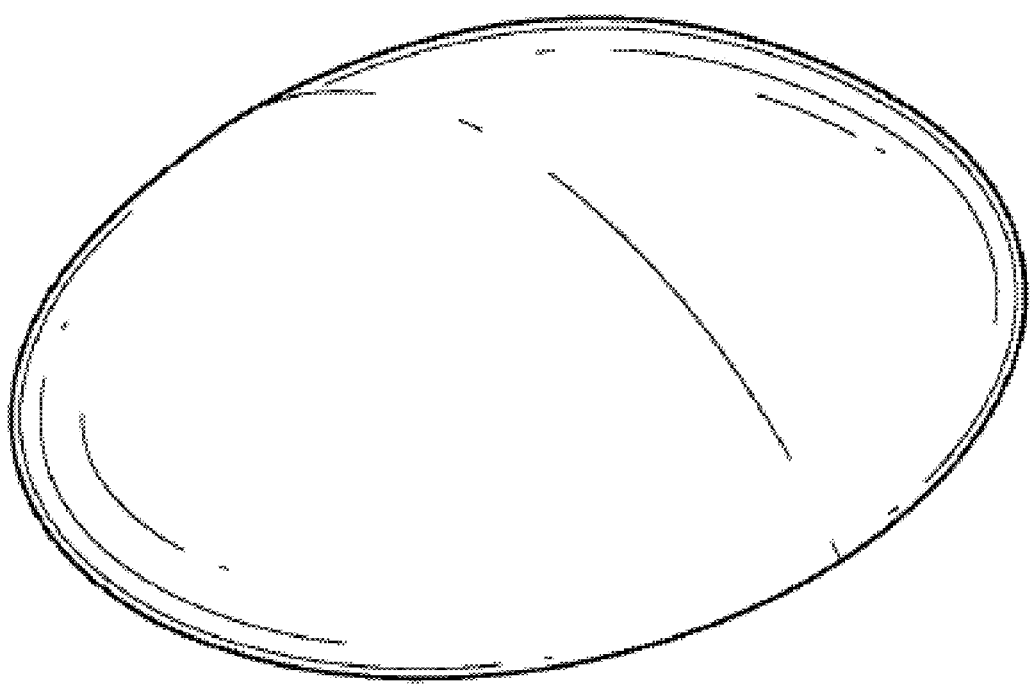
FIG. 6E shows a perspective view of an implant as described herein having the form of a gluteal implant.
Figure 12A:
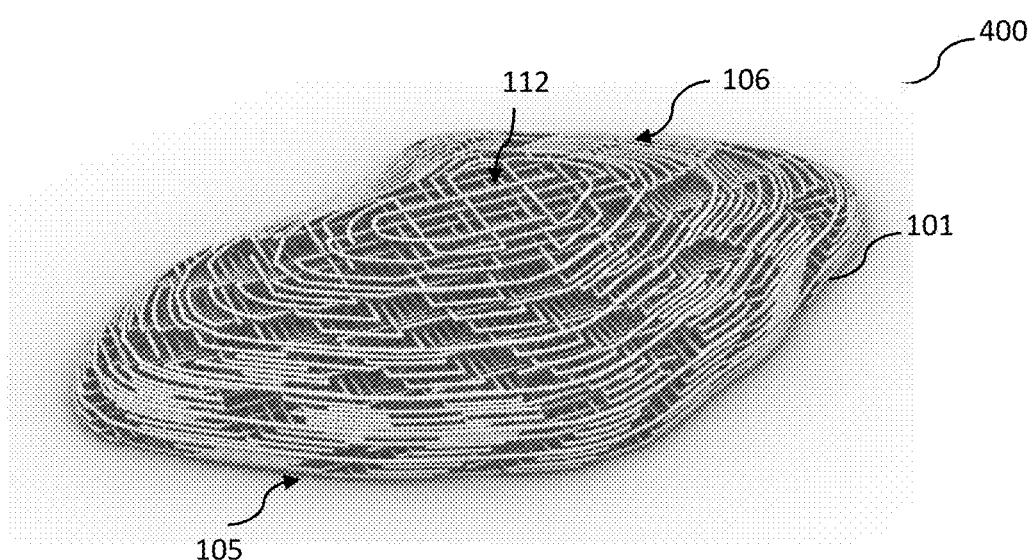
FIGS. 12A to 12C show schematic views of a soft tissue reconstruction implant for the reconstruction of a malar region (or cheek) of a patient's body.
Figure 12B:
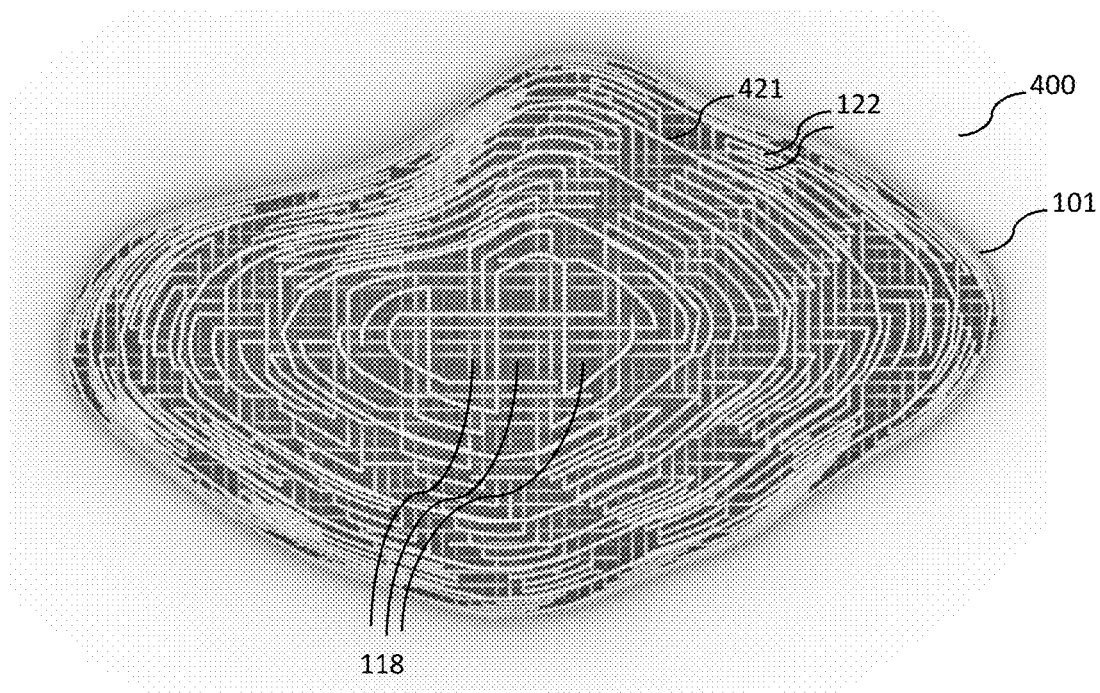
Figure 12C:
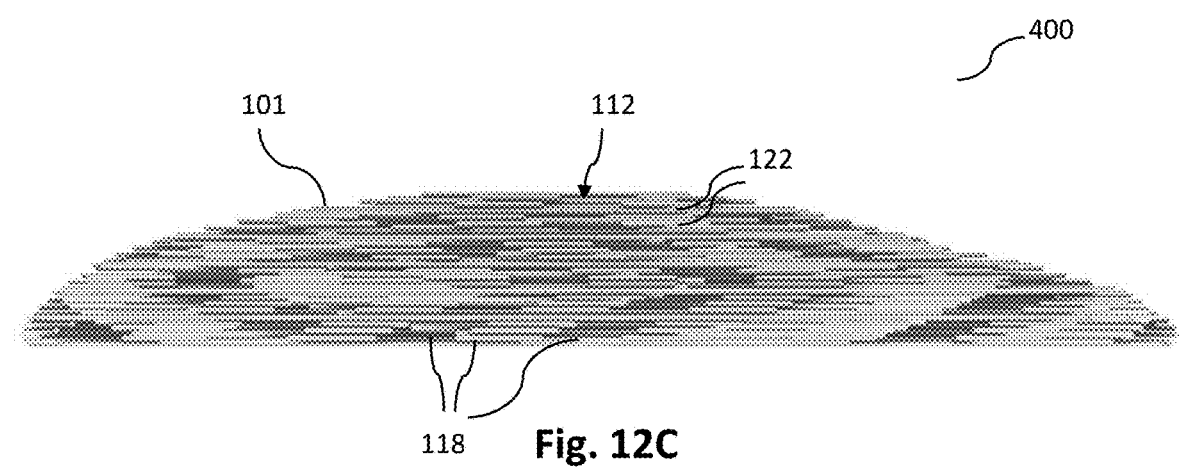
Figure 13A:
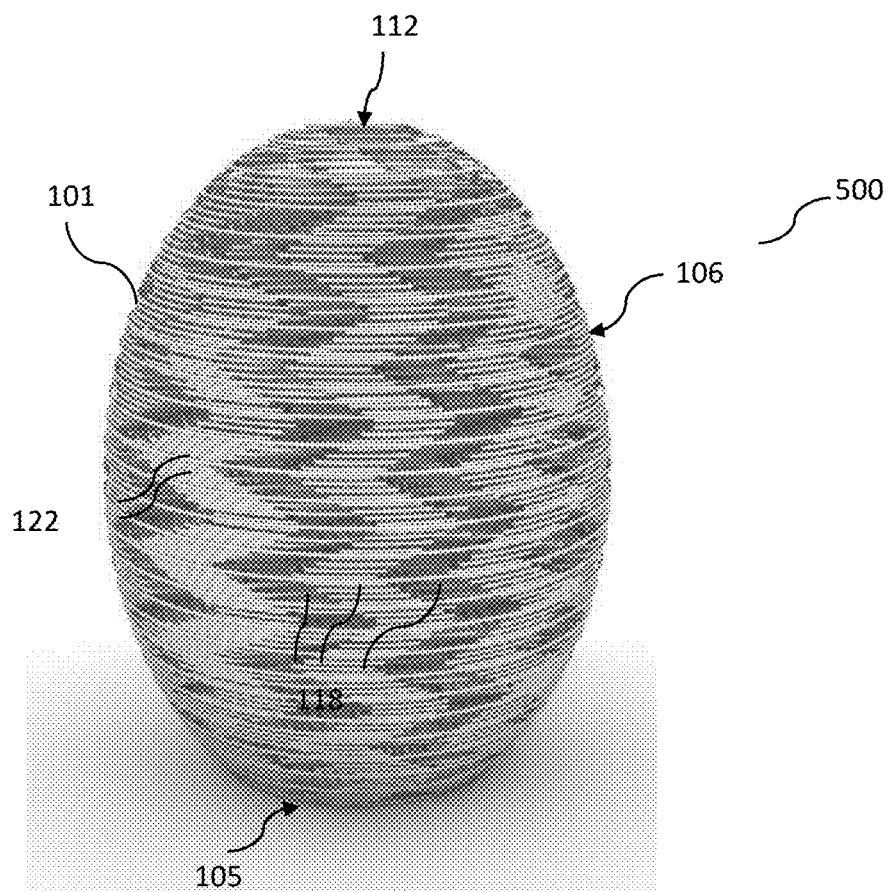
FIGS. 13A to 13B show schematic views of a soft tissue reconstruction implant for the reconstruction of a testicular region of a patient's body.
Figure 13B:
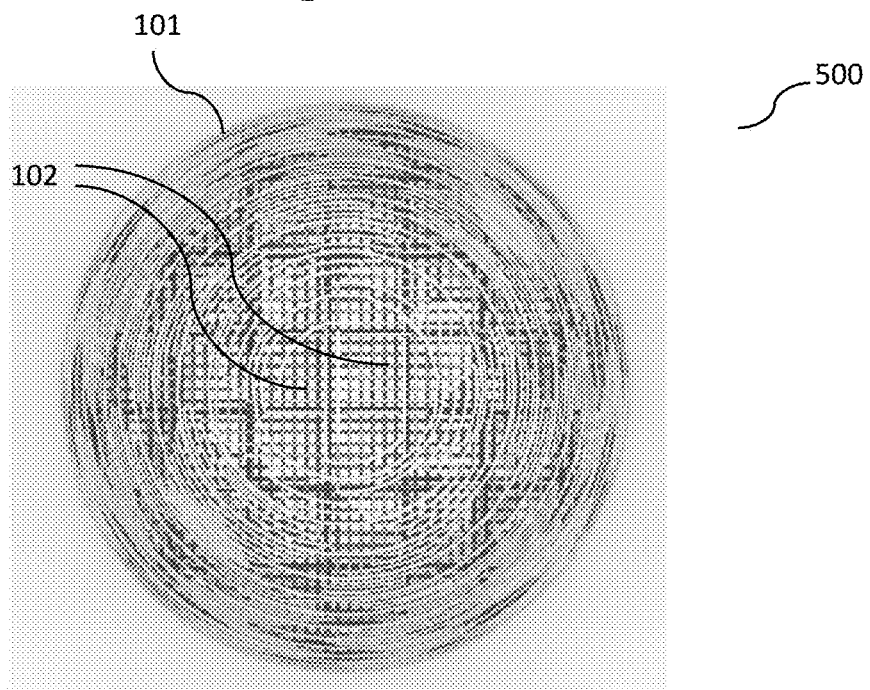

To help the tissue maintaining the shape and not being affected by the weight, the regenerated tissue can be reinforced without considering any additional materials, which could cause safety issues, but by depositing the material of the implant 200 in a way that the filaments (channels) are oriented in the direction of the tensile force needed to support the structure. While the material degrades inside the body, the areas of tissue directly surrounding the scaffold fibres are made of dense regular connective tissue aligned along the surface of the struts, which is the same composition of tendons and ligaments. Therefore, it is possible to anchor the scaffold to the surrounding tissue and at the same time having a self-made structure (e.g. a templating scaffold structure), which provides stability to the shape over time. Thus, although the implant 200 is described here first with respect to breast implants, such an implant is also valid for other parts of the body, such as the chest, the gluteal region (also known as buttock), the calf, parts of the face such as a cheek (or malar region) or even a genital region such as the testicular region, to name only a few illustrative body regions. Thus, an implant of the invention can adopt any suitable form, merely depending on the tissue that is to be reconstructed or augmented. The implant may, for example, have the form of a gluteal implant as described in U.S. Pat. No. 10,004,585 (a perspective view of a gluteal implant having a form as described in U.S. Pat. No. 10,004,585 is shown in FIG. 6E), the chest (see the pectus implant shown in FIGS. 11A to 11E for the reconstruction of pectoral or chest areas of a patient's body), the malar or cheek region (see FIGS. 12A to 12C showing schematic views of a soft tissue reconstruction implant for the reconstruction of a malar region (or cheek) of a patient's body) or of the testicular region (see FIGS. 13A to 13B showing schematic views of a soft tissue reconstruction implant for the reconstruction of a testicular region of a patient's body).

Figure 7D:
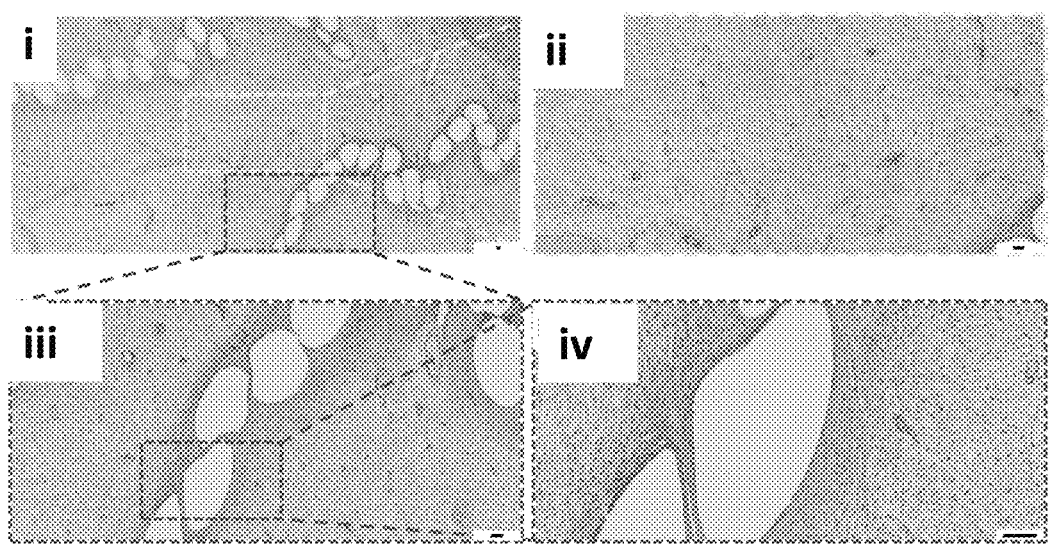
FIG. 7D shows histological pictures of regenerated breast tissue.

FIG. 7D shows histological pictures of regenerated breast tissue.

The tissues that regenerate inside the channels 118 of the implant 200 after insertion into the patient, may be loose in nature and may have a high degree of vascularisation and randomness in terms of collagen fibre alignment (panels (i) and (ii)). However, areas of tissue directly surrounding the scaffold fibres are dense regular connective tissue, having the same composition of tendons and ligaments, aligned along the surface of the struts (panels (iii) and (iv)). Thus, by the use of 3D printing technique to form the channels 118 of the implant 200, it is possible to control where the stiffest areas of the tissue will grow.

In daily activities (e.g. standing, running jumping and walking) in healthy tissue, the maximal forces may be carried by the Cooper's ligaments 144, which are anatomically considered as the structural framework which holds the breast to be constructed. The plurality of hollow channels 118 may be configured to be aligned with Cooper's ligaments 144 of the patient receiving the implant 200, so that after insertion of the implant 200 into the patient, fluids or blood vessels may infiltrate the pores (e.g. the hollow channels) of the implant 200 to form tissue fibres aligned long the hollow channels, mimicking the alignment of the Cooper's ligaments 144 of the patient before the insertion of the implant 200. The channels 118 may be oriented in a way such that once the regenerated tissue will be fully embedded in the surrounding tissue, the denser tissue will be aligned as Cooper's ligaments (e.g. from the muscle 143 to the nipple 142) and may exert a tensile force acting as support for the new tissue (FIG. 7A) which contributes and improves the structural stability of the implant 200.

Figure 7E:
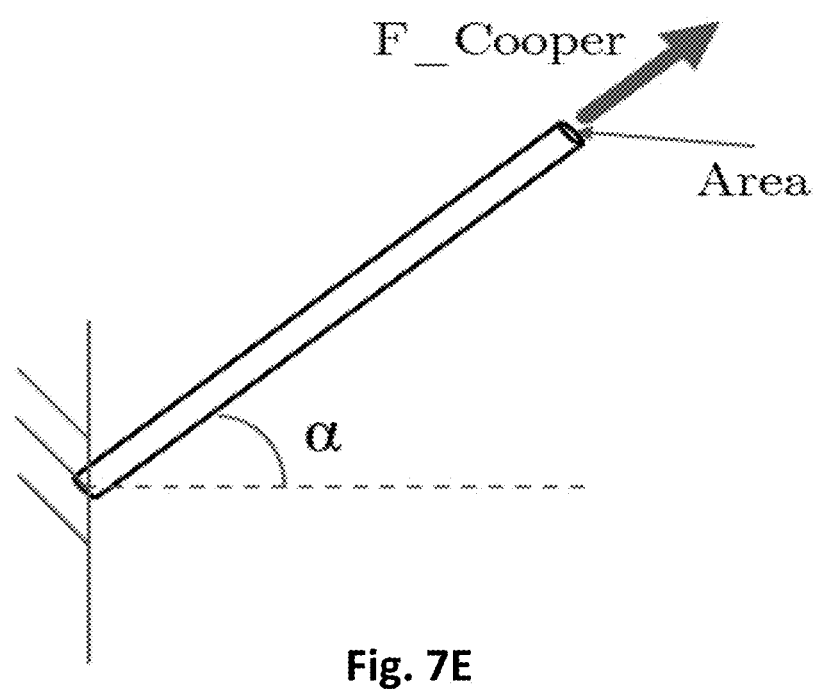
FIG. 7E shows an illustration of a Cooper's ligament force acting on one filament of an implant.

FIG. 7E shows a Cooper's ligament force acting on one filament (or e.g. one channel with absorbed tissue).

The number of channels 118 of the implant 200 and a tilt angle of the channels 118 of the implant 200 may be determined by examining the forces from daily activities, and the tensile strength of the ligaments.

Assuming (an extreme case) a breast mass of m=1 kg and an angle of $\alpha$=60° while jumping, the force that Cooper's ligaments ($F_{Cooper}$) may be subjected to may lie between 50 to 60 N. After the absorption of the strands into the hollow channels 118, the area of dense tissue may be roughly similar to the filament. For example, a filament (a channel) of the implant 200 having a diameter of 200 μm diameter, would have a surface area of $314 \times 10^{-10}$ m².

The force acting on a single dense connective tissue filament may be calculated by Force=strength ($\sigma$)×Area where the strength may be the tensile strength of ligaments and the area of the tissue replacing the filaments. A tensile strength of ligaments is reported to be 40 MPa.

The maximum force value borne by a single filament may then be expressed as $F_{filament} = 40 \times 10^6 \times 314 \times 10^{-10} = 1.2$ N In the worst case (fibre diameter of 200 μm, m=1 kg and $\alpha$=60° while jumping), a force of 60 N generate may require a total number of filaments to be $$\text{number of filaments} = \frac{F_{Cooper}}{F_{Filament}} = 50 \text{ filaments}$$

For healthy breast tissue, the tilt angle, $\alpha$, may range from between 45° and 60°. A theoretical maximum and minimum for a that can be used for the filaments inside the three-dimensional structure may thus be calculated.

Figure 7F:
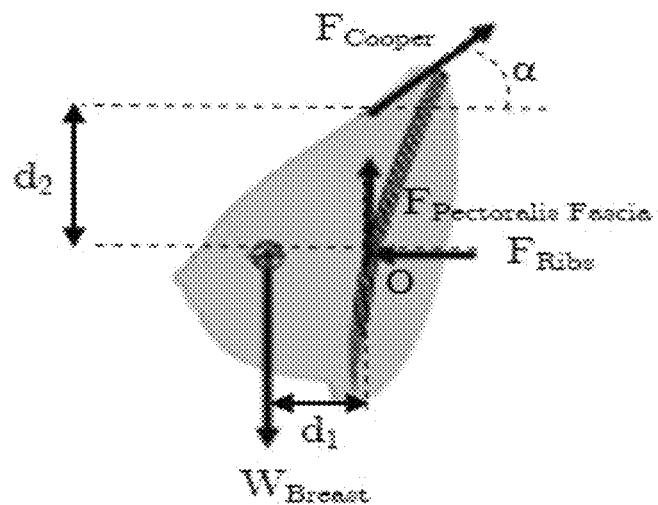
FIG. 7F shows illustrations showing the internal forces acting on the breast tissues.
Figure 7F:
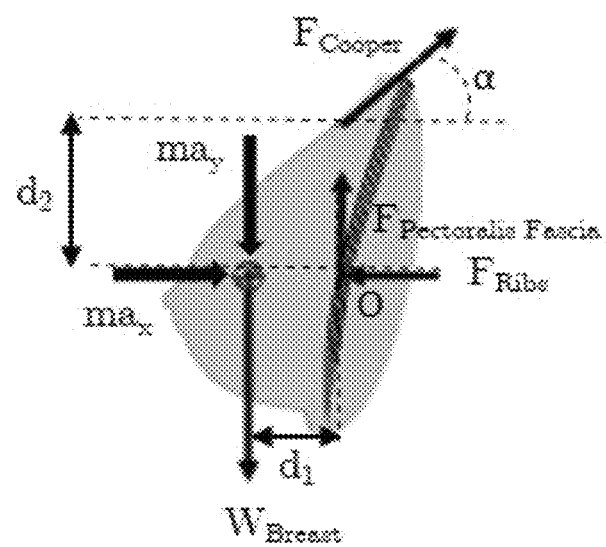

FIG. 7F shows illustrations showing the internal forces acting on the breast tissues while running, jumping, walking and standing.

$d_2$ represents the effective radius of curvature of the breast; $d_1$ represents the centre of gravity of the breast (assuming it reasonably as a semicircle); $\alpha$ is the dorsal insertion angle of the breast; O is the reference point at the base of the breast.

The forces from standing, walking, running and jumping may be expressed as follows:

| | Internal Breast Forces | | |
|---|---|---|---|
| Activity | $F_C$ ($F_{Cooper}$) | $F_P$ ($F_{Pectoralis\ Fascia}$) | $F_R$ ($F_{Ribs}$) |
| Standing | $\frac{W}{\cos \alpha} * \frac{d_1}{d_2}$ | $W\left(1 - \frac{d_1}{d_2}\tan \alpha\right)$ | $W\frac{d_1}{d_2}$ |
| Walking, Running | $\frac{(W + ma_y)}{\cos \alpha} * \frac{d_1}{d_2}$ | $(W + ma_y)\left(1 - \frac{d_1}{d_2}\tan \alpha\right)$ | $(W + ma_y)\frac{d_1}{d_2} + ma_x$ |
| Jumping | $\frac{(W + ma_y)}{\cos \alpha} * \frac{d_1}{d_2}$ | $(W + ma_y)\left(1 - \frac{d_1}{d_2}\tan \alpha\right)$ | $(W + ma_y)\frac{d_1}{d_2}$ | m is the mass of the Breast and W ($W_{Breast}$) is the force generated by the weight of the breast.

In order to find values of the forces, m may be considered to range from 0.5 to 1 kg;

$$\frac{d_1}{d_2} = \frac{4}{3\pi}$$

and $\alpha$ ranging between 45° and 60°. The accelerations are assumed to be the maximal reported in the literature in order to calculate the maximal internal breast tissue forces.

The accelerations may be considered to be as follows:

| | Trunk acceleration components | |
|---|---|---|
| Activity | Superior-inferior ($a_y$) | Anterior-posterior ($a_x$) |
| Walking | 0.8g | 0.4g |
| Running | 5g | 2.5g |
| Jumping | 6g | 0 | g = 9.81 m/s².

The forces may be calculated to be as following:

| Activity | $F_{Cooper}$ (N) | $F_{Pectoralis\ Fascia}$ (N) | $F_{Ribs}$ (N) |
|---|---|---|---|
| Standing | 2.9-8.3 | 1.3-5.6 | 2.1-4.2 |
| Walking | 5.3-15 | 2.3-10.2 | 5.7-11.4 |
| Running | 17.7-50 | 7.8-33.9 | 24.8-49.5 |
| Jumping | 20.6-58.3 | 9.1-39.5 | 14.6-29.1 |

In the following example, an extreme case scenario may be assumed e.g. a small volume of implant (100 ml) having 65 filaments, and a breast weight of 1 kg hanging while jumping without bra. It is important that the equilibrium is maintained to ensure that the breast will keep its shape and to prevent sagging. The equilibrium may be expressed as:

$(W+ma_y) \times d_1 = (F_C \cos \alpha) \times d_2$

And α is calculated as following:

$$\alpha = \cos^{-1}\left(\frac{(W + ma_y)}{F_{TOT}} \times \frac{d_1}{d_2}\right)$$

Where $W = 9.8$ N, $m = 1$ kg, $a_y = 6 \times g$, $g = 9.81$ m/s$^2$, $$\frac{d_1}{d_2} = \frac{4}{3\pi}.$$

Assuming that all the filaments are working in tension, the maximum force that can be applied is $$F_{TOT} = F_{filament} \times \text{no. of filament} = 1.2 \text{ N} \times 65 = 78 \text{ N}$$

For example, a maximal value of α may thus be calculated to be $$\alpha = \cos^{-1}\left(\frac{(W + ma_y)}{F_{TOT}} * \frac{d_1}{d_2}\right) = 87°$$

Assuming that only half of the filaments are working in tension. The maximum force that they can apply is:

$$F_{TOT} = F_{filament} \times \text{no. of filament} = 1.2 \text{ N} \times 30 = 36 \text{ N}$$

For example, a minimum value of α may thus be calculated to be $$\alpha = \cos^{-1}\left(\frac{(W + ma_y)}{F_{TOT}} \times \frac{d_1}{d_2}\right) = 36°$$

Thus, the acute tilt angle, k, between a sidewall of a hollow channel of the plurality of hollow channels and a reference axis (e.g. an x-axis) representing the first outer surface region may be range from between 3° to 87°, or from 3° to 54° (or e.g. between 10° and 50°, or e.g. between 25° and 45°).

The implant 200 may permit tissue regeneration and keep fat tissue alive once injected in the scaffold, nourishment is needed. The four main blood sources in the breast are the internal mammary artery, the lateral thoracic artery, the anterior intercostal artery, and the thoracoacromial artery. The scaffold structure and/or the porous network of unit cells 102 of the implant 200 may thus provide space for the vessels to infiltrate and populate the scaffold, especially at the interface between the scaffold and the major blood sources. Nevertheless, it is important for the implant 200 to have all over the scaffold a suitable space to let vessels access from everywhere. A highly porous implant may however, lead to discomfort for the patient. For example, the more porous an implant is, and the higher the surface roughness, and the more discomfort it may create for the patient. The implant 200 provides space for exchange of substances (potentially harmful substances which may be trapped inside the scaffold may escape, and substances which may help tissue regeneration may enter the scaffold), and still takes into account the comfort of the patient (e.g. by reducing tissue irritation and/or inflammation). The implant 200 addresses the comfort of the patient (via space filler portions, and contouring lines) and the safety of the scaffold, by providing a smooth interface between the scaffold and the tissue despite the scaffold being porous.

To support vascularisation of the scaffold, the implant 200 may take into account having the highest pore-size of the scaffold facing the major blood supplies (e.g. FIG. 7A) and having a high porous scaffold. To compromise with the roughness of the surface and providing space for the blood vessels to infiltrate and distribute though all the scaffold, different porosities (e.g. two or more different porosities and/or pore-size range) may be considered (FIGS. 2A to 2E). For example, the upper surface porosity and/or pore size range, may be lower than the bulk porosity value, but may face the area of the tissue where just minor blood supplies are located. For example, the bulk porosity and/or pore size range may be higher than surface value and may provide space for all the blood vessels to colonise the entire scaffold. Due to the possibility of controlling the fibre deposition, the channels of the implant may be aligned towards major blood vessel supplies, having the biggest pore size at the interface between the scaffold and the muscle and the smallest pore size at the interface between the scaffold and the nipple/breast tissue. For example, a pore size of 8 mm at the bottom and 2 mm at the top, having the projection of the channels in the inferior side of the implant ranging between 6 mm and 2 mm.

Due to the possibility of controlling the fibre deposition, the implant 200 may include full contours at the bottom to ensure stability of the implant and semi-contours on the rest of the scaffold to ensure that the pores on the lower pole of the scaffold are maintained (FIGS. 4A to 4B). The semi-contours may be used to make the surface smooth and comfortable for the patient but at the same time maintaining a certain porosity is needed to permit the exchange of substances and blood vessels infiltration. In some examples, the implant 200 may include an upper pole surface where the porosity is roughly 83% and the upper pole surface pore size is between 0 and 6 mm. The bulk porosity may be 95% and the bulk pore size may be between 0 and 8 mm.

Unlike the implant 200, traditional silicone implants may be filled with incompressible fluids. However, over time silicone implants may burst causing health issues, and may lead to additional surgeries.

The implant 200 may be formed using 3D printing to control fibre (channel) deposition, and to create reversibly compressible structures, to create the implant 200 that is comfortable for the patient. The implant 200 may be configured to provide shape stability while retaining the softness of the implant. The implant 200 may ensure that that the shape of the implant corresponds to what has been requested, and that the final shape of the breast after insertion into the patient may be ideal and natural.

The implant 200 provides shape stability to the scaffold by using a spring-like system (FIGS. 1C to 1D), which deforms if a force is applied and when released it recovers the shape, avoiding pore obstruction and any extra force exerting on the chest cavity, which could cause damages to the tissue or in the most severe situations to the lungs. The reversibility compressible structure may transfer the forces acting along one direction to the perpendicular direction (FIG. 1C). Once the force is released, the energy stored during this process will act in the opposite direction (FIG. 1D) helping the shape springing back and recovering the shape in less than 8 h.

Shape stability and the softness of the implant are important to ensure comfort of the patient. The implant 200 may have anisotropic mechanical properties, which may include a combination of spring-like unit cell and the channels aligned towards the nipple area. Due to the spring-like unit cells, the implant 200 may be soft in the lateral direction to ensure a natural tactile feeling. Moreover, due to the combination of the spring-like unit cell and the orientation of the channels, along the printing direction, the implant 200 may still be soft but robust enough to maintain the shape under the weight of the tissue and other forces.

To ensure shape stability and desired softness of the implant 200, the anisotropic mechanical properties may include the combination of both spring-like unit cell effect and channels aligned in the direction where major forces are applied. To ensure that the volume of the scaffold inside the body may be the same as the requested volume, the implant 200 may be formed by considering the forces acting on the scaffold after insertion to patient, and a predetermined % of extra volume (or extra dimensions) may be considered during manufacturing. To provide a natural outcome, depending on the shape to achieve and the forces acting on the breast, adjustments on the external shape may be considered in advance, such that after applying the force the desired outcome is reached.

Figure 8:
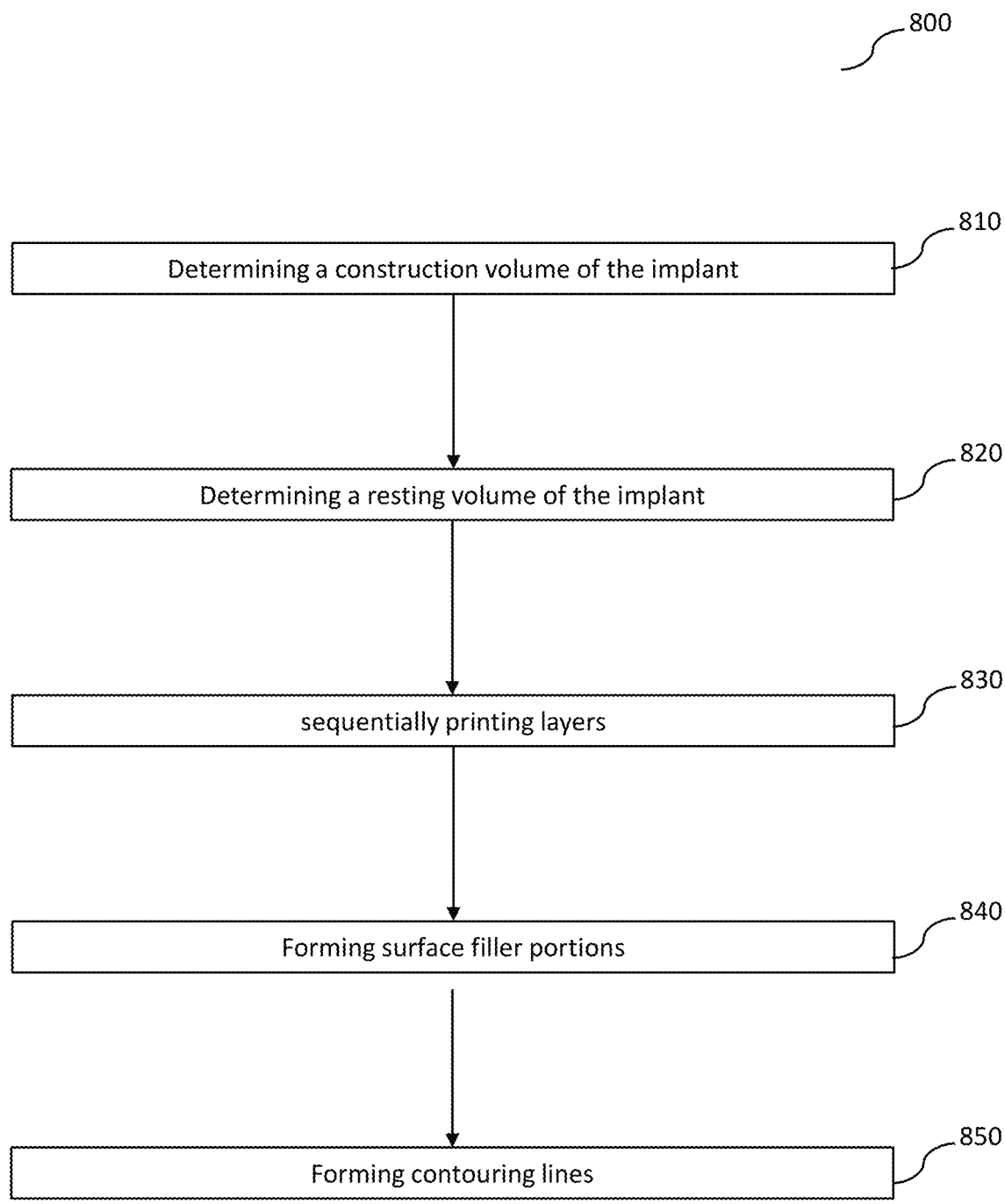
FIG. 8 shows a flow chart of a method for forming an implant.

FIG. 8 shows a flow chart of a method 800 for forming an implant of the invention.

The method 800 comprises sequentially printing layers 830 to form a three-dimensionally (3D) printed structure. The three-dimensionally printed structure defines a resting volume of the implant to be formed. Each printed layer comprises a lattice arrangement of two-dimensional unit cells. The three-dimensionally printed structure has a porosity such that (or wherein) the three-dimensional printed structure is compressible to at least 80% of its resting volume.

The method 800 may optionally include determining 810 a construction volume of the implant before sequentially printing the layers. The method 800 may further include determining 820 a resting volume of the implant based on the construction volume of the implant. For example, resting volume of the implant to be printed may be an overestimation of the construction volume of the implant.

In the method 800, sequentially printing 830 the layers may include printing a first layer to form a first outer surface region of the 3D printed structure, and printing successive layers over the first layer according to a print direction. The print direction (e.g. the z-direction) may be a direction perpendicular to the plane of the first layer. The edge regions of the successive, sequentially printed layers may form a second outer surface region of the 3D printed structure contiguous to the first outer surface region. The second outer surface region may define the geometry of the breast to be constructed by the implant, and the region between the first outer surface region and the second outer surface region may define the resting volume of the implant before implantation into the patient.

The successive layers may be arranged with respect to each other, so that the unit cells of the layers may form a plurality of hollow channels of the 3D printed structure. The plurality of hollow channels may extend between the first outer surface region and a second outer surface region of the three-dimensional structure (e.g. in direction from the first outer surface region towards the second outer surface region.

Optionally, the layers may be sequentially printed to form a plurality of three-dimensional unit cells (e.g. tetrahedral unit cells) of the 3D structure. Optionally, the two-dimensional unit cells of a layer may be regarded as a facet (or a planar face) of the three-dimensional unit cell.

The method 800 may further include forming 840 a plurality of surface filler portions after forming the sequentially printing the layers. Forming the surface filler portions may include forming one or more filler lines to at least partially fill one or more openings (surface pores) at the outermost surface of the three-dimensional structure.

The method 800 may further include forming 850 a plurality of contouring lines after sequentially printing the layers. Forming the plurality of contouring lines may include forming a first group of contouring lines around a perimeter of the first outer surface region and/or a second group of contouring lines. Unlike the first group of contouring lines forming a full contour around the perimeter of the first outer surface region, each contouring line of the second group of contouring lines may form a semi-contour around the second outer surface region.

It may be understood that the features described with respect to the various embodiments herein may be combined with each other. The method 800 may include one or more or all of the features already described with respect to the FIGS. 1B to 7F.

EXPERIMENTAL EXAMPLE 1

Figure 9A:
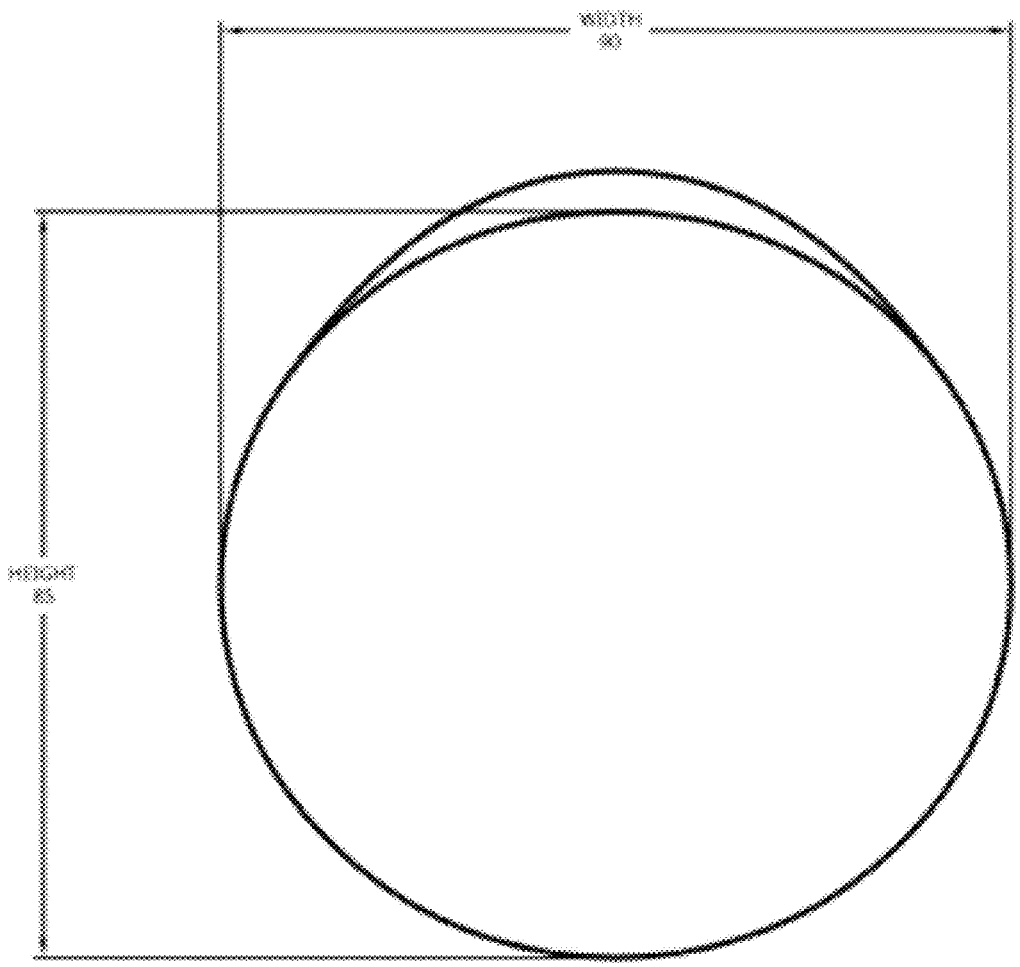
FIG. 9A shows a schematic view from the bottom of the implant used in the animal study described herein with the dimensions of the implant also being indicated.
Figure 9B:
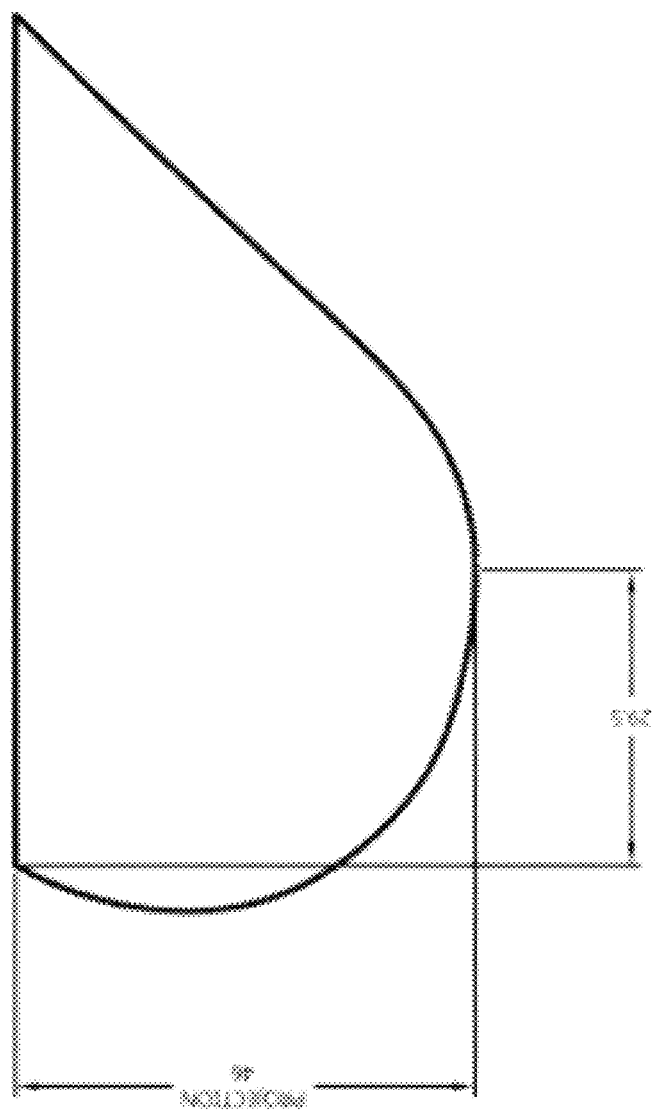
FIG. 9B shows a schematic side view of the implant used in the animal study described herein with the dimensions of the implant also being indicated.

A Long-Term Implantation Study with an Implant of the Invention in Combination with Autologous Fat Grafting (AFG) within a Large Animal (Elegaard Göttingen Minipig) Model An absorbable implant (scaffold) made of medical grade polycaprolactone by 3D printing as described herein adhering to ISO 11137 (Sterilisation), 13485 (Quality Systems), 11607 (Packaging), and 14644-1 (Clean Room) standards was used to study to assess the safety of the finished implants, including:
1. Assessment of long-term immunological response.
2. Assessment of long-term AFG sustenance.
3. Device (Implant) Performance.
4. Handling of device during surgical procedures Elegaard Göttingen Minipigs obtained from Elegaard, Dalmose, Denmark were chosen for this study. 100 $cm^3$ scaffolds were used owing to the smaller size of the animals. The scaffolds had the following dimensions (see also FIGS. 9A and 9B):
   Height: 84 mm
   Width: 91 mm
   Projection: 31.5 mm
   Pore size at the bottom and top of the implant: 4 mm (bottom), 8 mm (top), meaning the average pore size is greater than 4 mm The size of the minipigs employed in this study is about 1.5× smaller than that of an average human female. Taking the size difference into account, the equivalent dimensions of the scaffold in an average human female would be:
   Height: 126 mm
   Width: 136.5 mm
   Projection: 47.25 mm
   Pore size at the bottom and top of the implant: 4 mm (bottom), 8 mm (top), meaning the average pore size is greater than 4 mm Therefore, the selected implant (scaffold) size in the minipig corresponds to an implant with a volume 300 $cm^3$ that would be placed in a human female with an average body size. However, it should be noted here that the implant used in the present animal study is intended to be employed for human patients as well, namely for female patients having a smaller than the average body size.

A total number of 32 animals randomised into three time-point groups (6-week pilot study, 12-month and 24-month main study) are included in this trial.
12-month time point→16 animals.
24-month timepoint→16 animals (n=32 treatments).

Figure 9C:
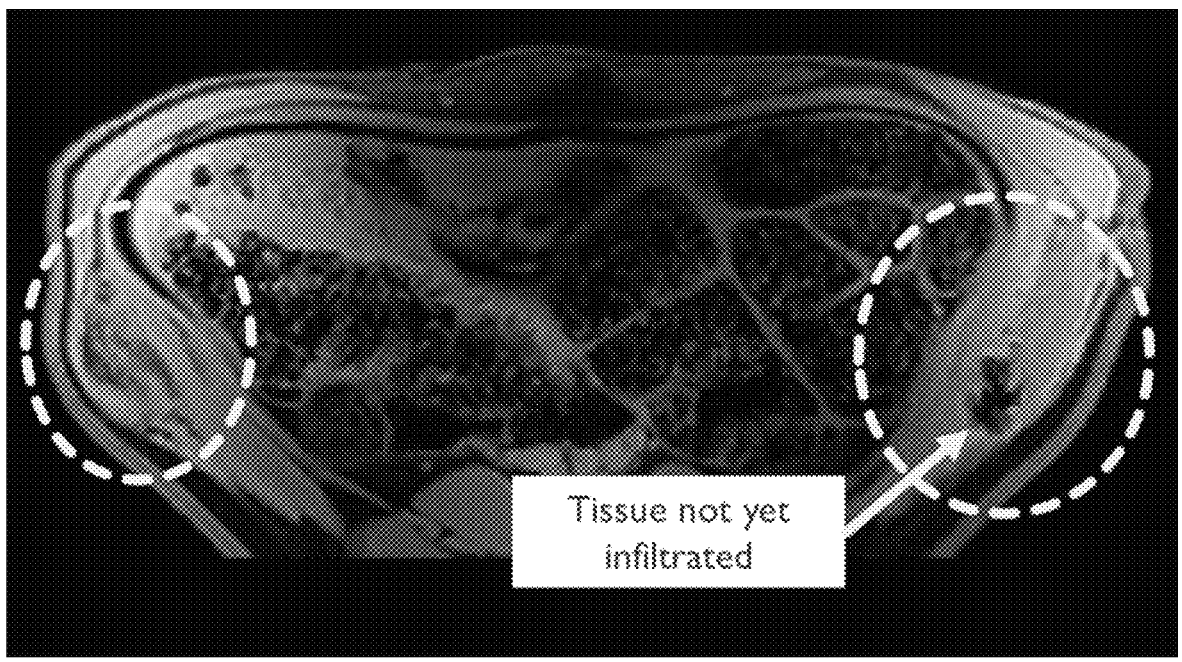
FIG. 9C shows a magnetic resonance imaging (MRI) image of a mini pig of treatment group 3 as explained herein into which an implant depicted in FIGS. 9A and 9B was inserted. The MRI image of FIG. 9C was taken two weeks after insertion of the implant.
Figure 9D:
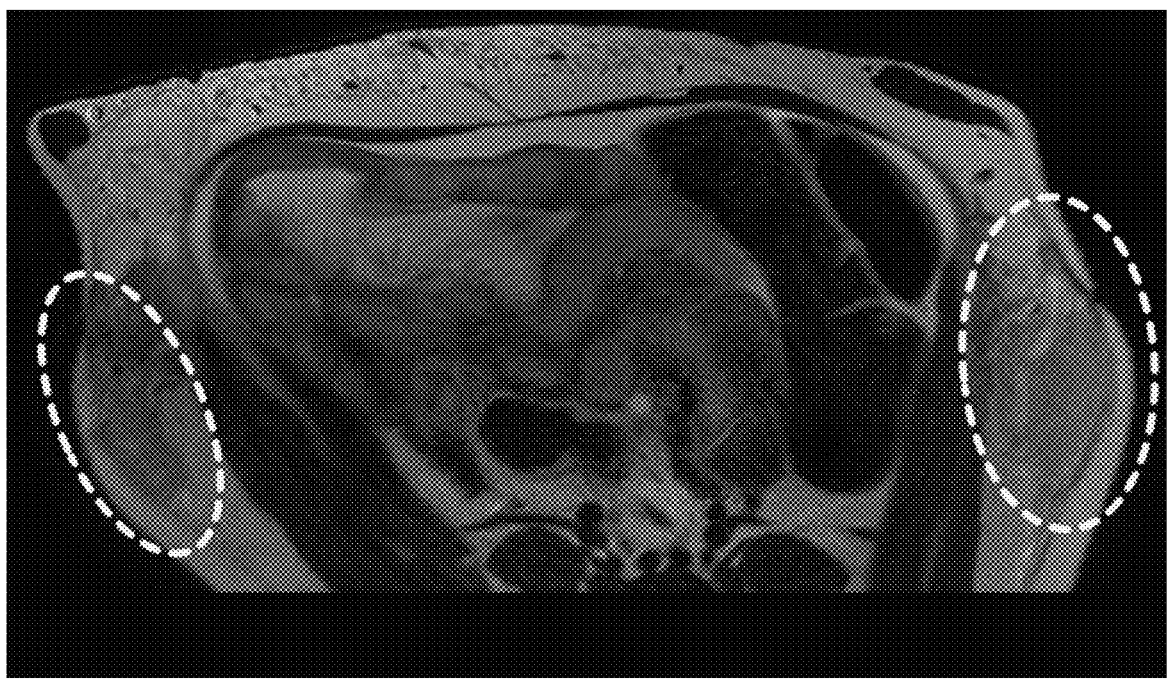
FIG. 9D shows a MRI image of the same mini pig as in FIG. 9C, wherein the MRI image was taken at 4 weeks after implantation.

The following four treatment groups have been chosen for the study.
1. Group 1 is a negative control group where only the implant of the invention is implanted (i.e. no AFG).
2. In Group 2, AFG (50 cm$^3$) is performed into the scaffold volume immediately following implantation of the implant (scaffold) of the invention.
3. In Group 3, the autologous-fat injection (50 cm$^3$) is carried out 4 weeks after the insertion of the implant of the invention
4. Group 4 is a positive control in which only AFG is performed—corresponding to standard AFG procedures performed in humans as far as practicable The tissue infiltration into the implant of the invention was assessed by magnetic resonance imaging (MRI). FIG. 9C shows partial tissue infiltration into the implants two weeks after implantation into a mini pig of treatment group 3, while FIG. 9D shows that full rapid tissue infiltration into the implant of this mini pig occurs already at 4 weeks after implantation. In this context, it is noted that with implants as described in WO 2016/038083 and Chhaya et al., 2016 supra, complete tissue infiltration was only observed after 24 weeks. Thus, the implant of the present invention results in a much faster tissue infiltration, thereby providing a significant advantage over the known implants.

The following further functional differences compared to, for example, the implant (scaffold) design described in WO 2016/038083 and Chhaya et al., 2016 supra were found in this study.

Pore Size & Porosity:

All published literature, including WO 2016/038083 and Chhaya et al., 2016 supra, related to soft tissue engineering describes scaffolds with average pore sizes less than or equal to 1 mm. In contrast, for regenerating large volumes of tissue (>50 ml) in a clinically relevant setting, it has been found in the present invention that large pores (>1 mm) are required to allow for efficient infiltration of vascularisation to the central areas of the implant. The implant of the present invention used in this study having a pore size of 8 mm at the bottom and 4 mm at the top (apex) thus fulfils this need and thus allows for efficient infiltration of vascularisation to the central areas of the implant.

Figure 10A:
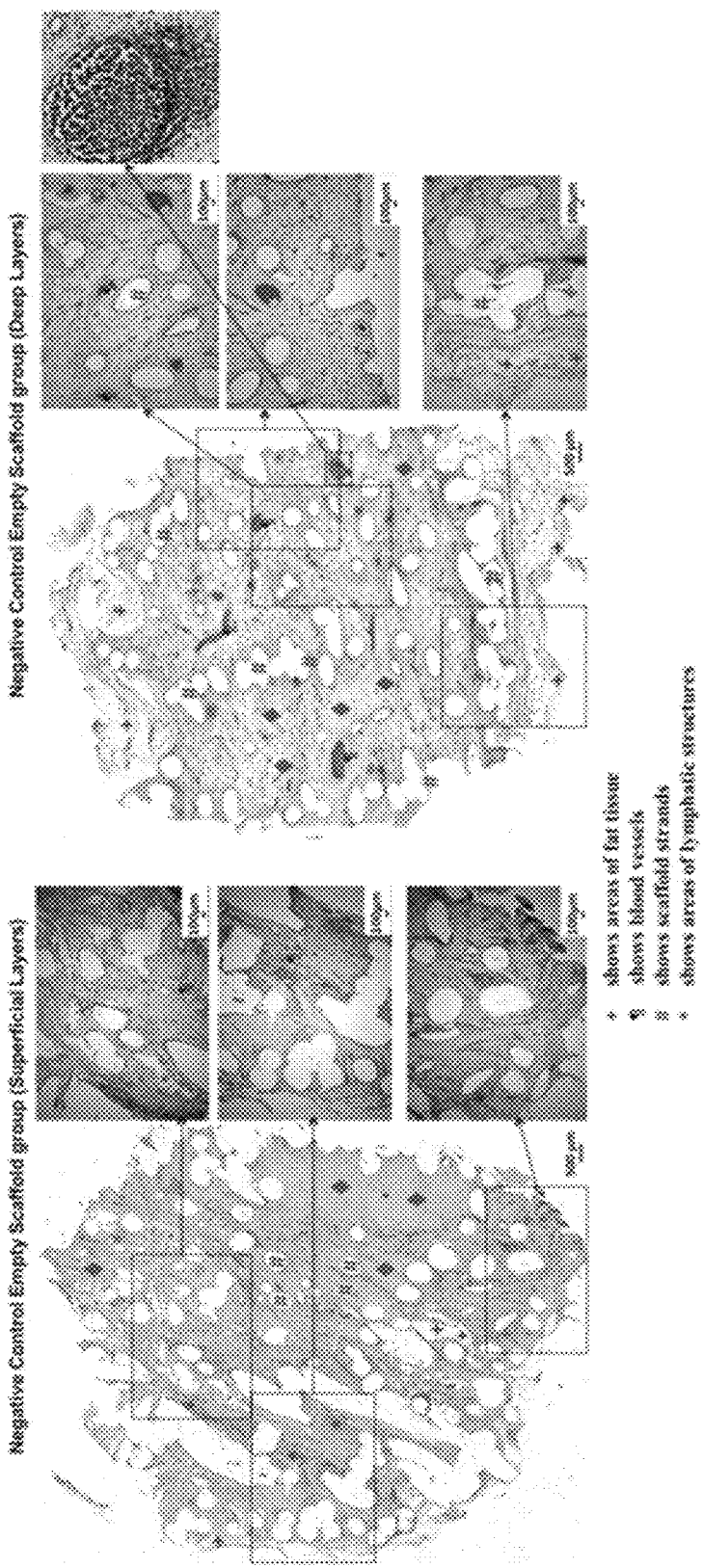
FIG. 10A is a reproduction of the histology images of FIG. 4 of Chhaya et al, supra 2016 that show areas of chronic inflammation characterised by lymphatic structures after implantation of an implant/scaffold in a mini pig as described in Chhaya et al. and WO 2016/038083.

Mechanical Properties:

Studies such as Chhaya et al 2016, supra which aimed at regenerating large volumes of soft tissue described the use of a combination of small pore sizes (<0.5 mm) with stiff porous architectures. Stiff architectures have been found to cause irritation within the tissue. This irritation issue had shown to cause mild chronic inflammation within the pores of the device as shown in Chhaya et al, supra 2016 FIG. 4 (which is reproduced here as FIG. 10A)—characterised by invasion of lymphatic structures into the tissue.

Figure 10B:
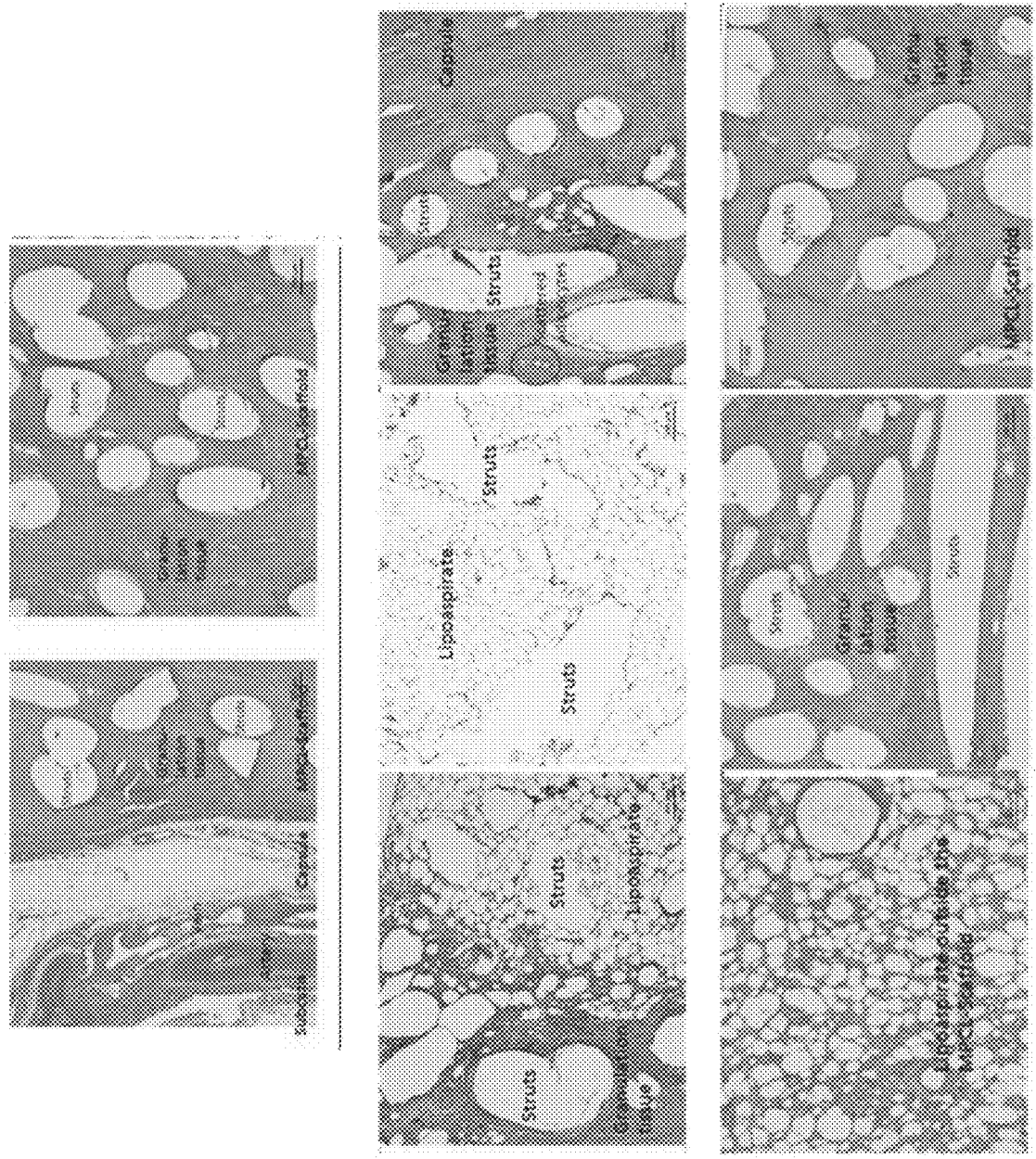
FIG. 10B shows histology images of FIG. 4 of Chhaya et al, supra 2016 that show the composition of the tissue infiltrated within the pores of the implant of the invention used in the animal study described herein.

In contrast, as shown in FIG. 10B the highly porous and spring-like compressible implants produced using the design features specified in the application did not cause any irritation or chronic inflammation. Thus, the ability of the implant of the invention to avoid inflammation after implantation, due to these mechanical properties, together with the very fast tissue infiltration and the low weight of the implant, makes the implant of the invention the ideal candidate for tissue restoration and augmentation.

FIGS. 11A to 11E show several views of a soft tissue reconstruction implant 300 for the reconstruction of pectoral or chest areas of a patient's body, such as in cases of congenital pectus excavatum. The implant 300 may include one or more or all of the features described in connection with FIGS. 1B to 10B, and various other features.

Figure 11A:
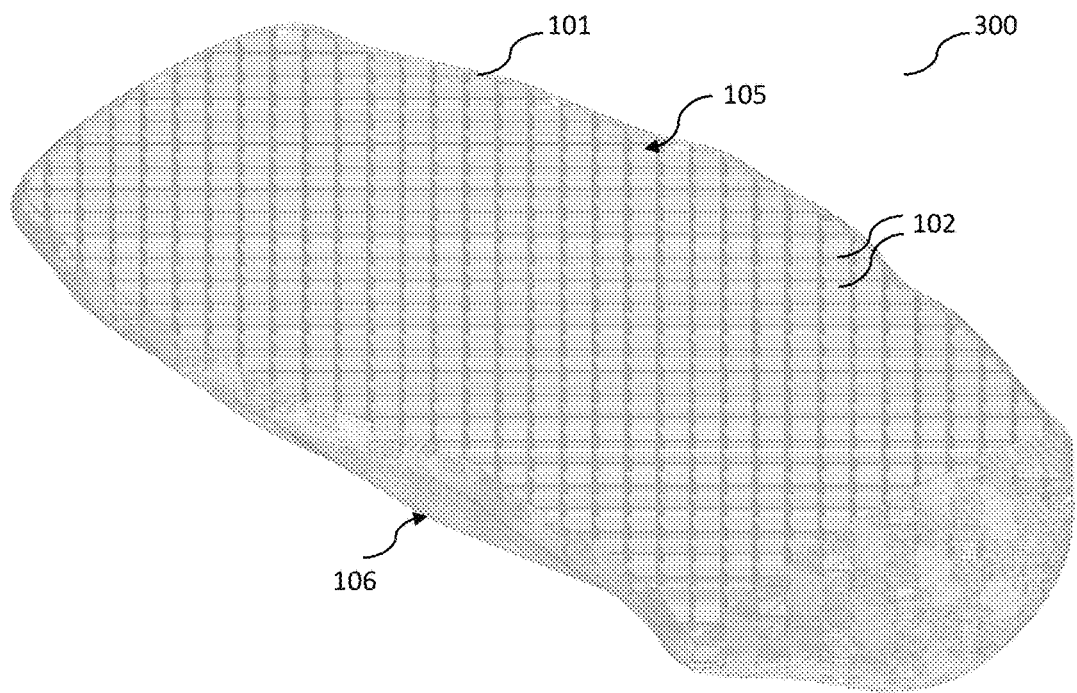
FIGS. 11A to 11E show schematic views of a soft tissue reconstruction implant for the reconstruction of pectoral or chest areas of a patient's body.
Figure 11B:
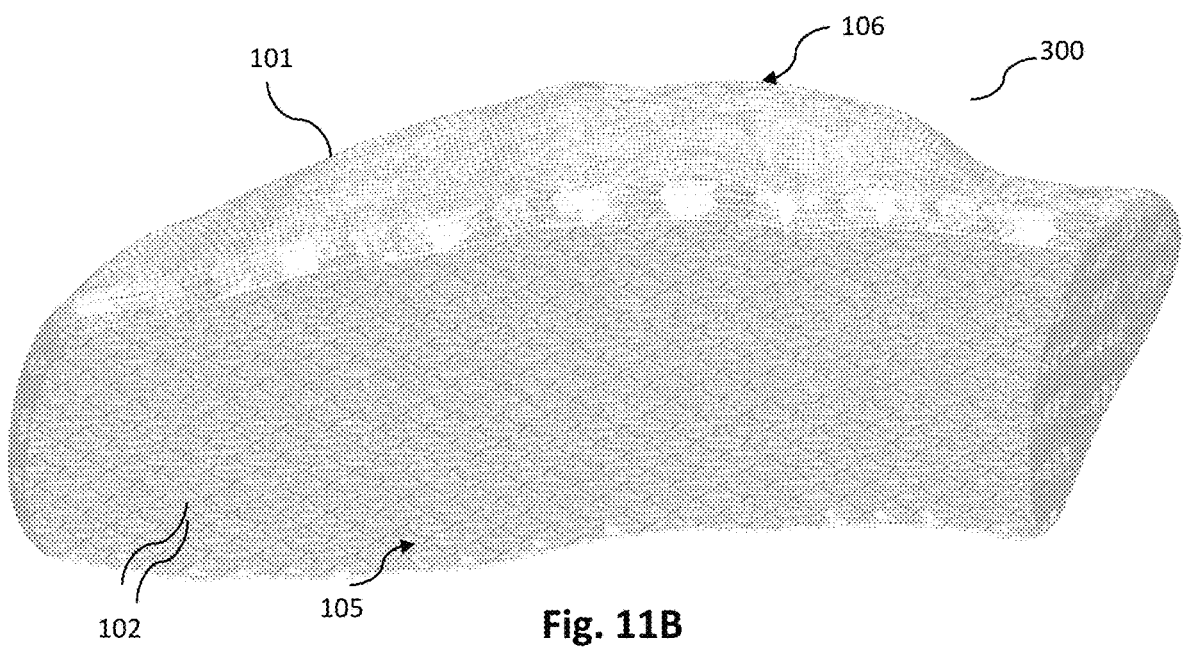

FIGS. 11A and 11B show respective bottom view illustrations of the pectus implant 300. The pectus implant may include a first outer surface region 105 which may be the largest planar (or e.g. flattest) surface of the implant. Successive layers of unit cells may form a plurality of hollow channels extending between the first outer surface region 105 and the second outer surface region 106 of the three-dimensional structure 101 of the pectus implant 300.

Figure 11C:
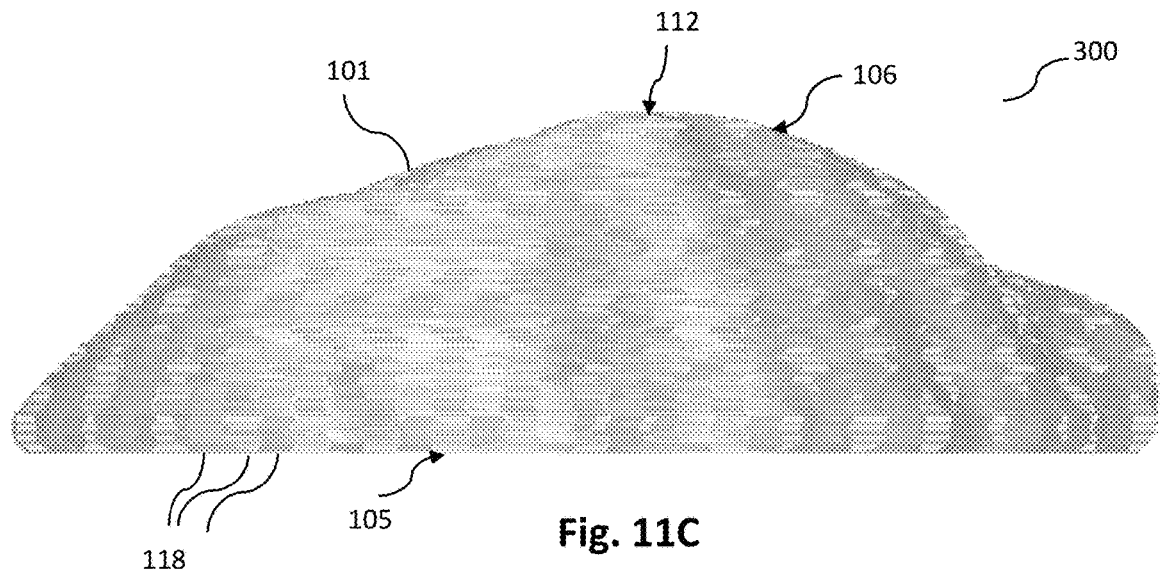
Figure 11D:
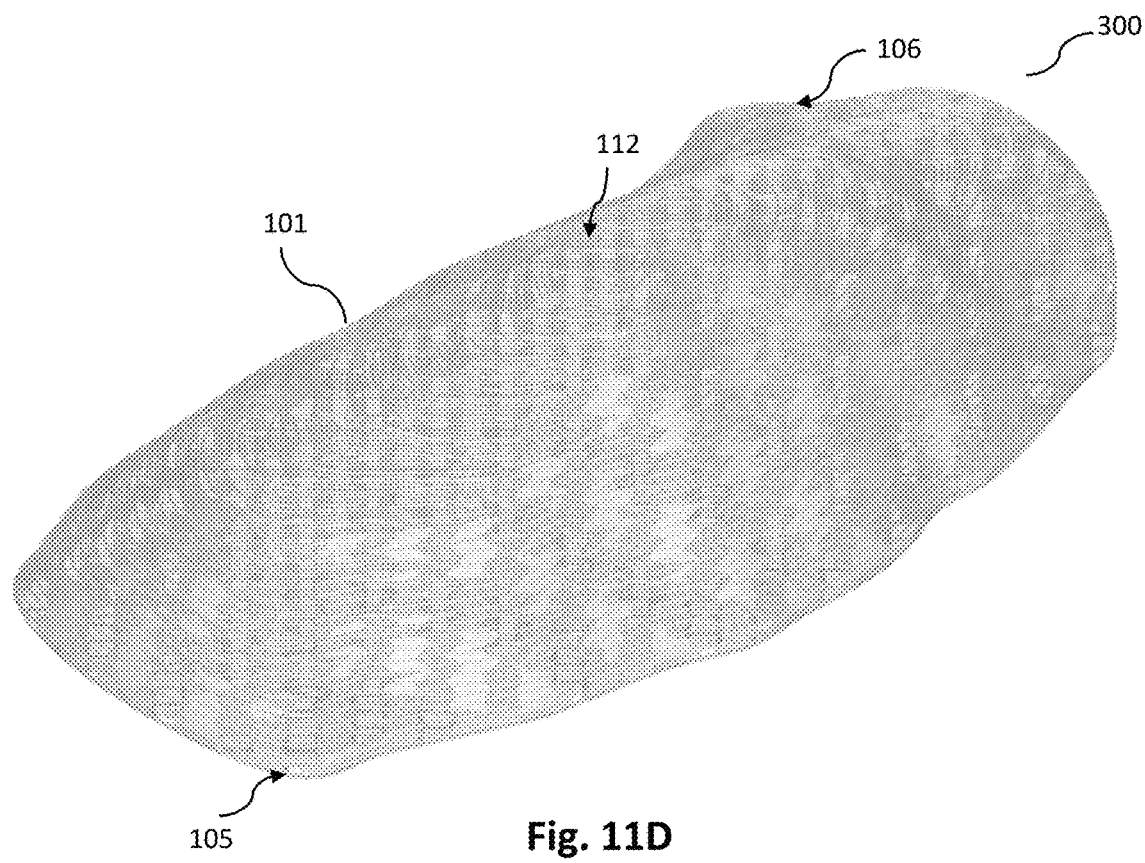

FIGS. 11C and 11D show perspective side and top view illustrations of the pectus implant 300. The contours and shapes of the second outer surface region 106 may be based on the desired size and shape of the pectus implant 300.

Figure 11E:
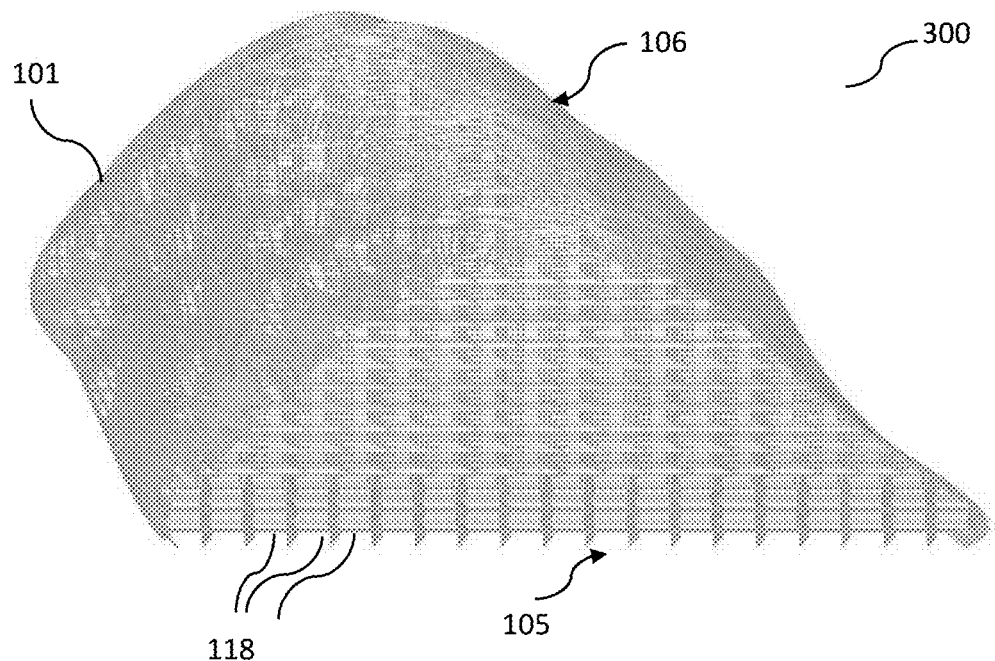

FIG. 11E shows a cross-section side view illustration of the pectus implant showing a plurality of hollow channels extending between the between the first outer surface region 105 and the second outer surface region 106 of the three-dimensional structure 101 of the pectus implant 300.

EXPERIMENTAL EXAMPLE 2

Phase 1 Trial of a Pectoral Implant

The soft tissue reconstruction implant (such as pectoral implant 300) as described herein is an absorbable soft tissue reconstruction scaffold, which is used to reconstruct pectoral or chest areas of a patient's body, such as in cases of congenital pectus excavatum. The impact of surgery is reported in https://www.abc.net.au/news/2020-07-21/would-first-3d-chest-scaffold-funnel-chest-queensland/12477704).

Three main surgery options currently exist for breast mound reconstruction following mastectomy or for congenital defects such as pectus excavatum. Reconstruction using silicone implants involves several drawbacks including capsular contracture. Additionally, silicone implants are also subject to potential rupture, displacement, deformation, chronic seroma or hematoma. Free tissue transfer, such as latissimus dorsi, pedicled transverse rectus abdominis myocutaneous, or deep inferior epigastric perforator flap surgery often takes eight to nine hours and is associated with extended in-patient stay and prolonged recovery periods. The main complication with these is that sometimes a clot forms in the vein that drains blood from the flap, or the artery that supplies blood to the flap. Both cases may lead to necrosis of the flap tissue. Lastly, autologous fat transfer or lipofilling, produces poor clinical results for large volume reconstruction (more than 100 cc), with 40% to 60% reduction in graft volume owing to tissue resorption and necrosis. For pectus excavatum defects, two other methods exist: the Nuss procedure and the vacuum bell. A key step in the Nuss procedure is to introduce a curved bar that lifts the sternum. Complications of this procedure comprise e.g. a long-lasting pain, a second surgery where the bars need to be removed after few years, possible damage to the heart and lungs during the surgery and misplacement of the bars. The alternative solution, the vacuum bell, which uses a suction cup to lift the sternum without surgical intervention, produces poor clinical results for severe cases of pectus excavatum and cannot be used in patients with cardiac disorders.

The trial with the pectoral implant described herein was carried out by plastic and reconstructive surgeons for the congenital deformity pectus excavatum. Pectus excavatum (funnel chest syndrome) is a deformation of the thorax, characterized by a median or lateral depression of the sternum. Funnel chest syndrome may occur in 1% to 2% of the population, and is the most common congenital thoracic deformity. The surgery for inserting to the implant into the body of the patient is designed as a minimally invasive procedure, where no bones are touched and recovery is expected to be less painful than other approaches to treatment, and wherein using the absorbable scaffold offers simplicity compared to other techniques which use silicone. The patient had a pectus excavatum deformity, and was born with a lymphovascular disorder affecting the chest wall and an upper limb, with hypertrophy of the limb. This set of symptoms is known as Klippel-Trenaunay syndrome. An old 6 cm scar, previously used to insert a tissue expander, was used to access the anterior aspect of the breast bone. This necessarily included releasing the sternocostal head of the ipsilateral pectoralis major muscle, as would be routine in breast augmentation surgery. Once the pocket for the implant had been created, the implant was inserted. Fat graft was then harvested from the patient's thighs and abdomen. The fat was prepared using a standard Coleman fat transfer technique and then injected directly into the implant using a standard fat injection cannula. An important part of the surgery is injecting the patient's own fat into the scaffold at the time of implant insertion or after few weeks. This stimulates regeneration of the highly porous scaffold with a significant amount of the patient's own tissue (e.g. more than 70%, or e.g. more than 80%, or e.g. more than 90%). The wound could then be closed in a standard two layer fashion. There was no need for a surgical drain. Light compression dressings were applied as would be routine for breast implant surgery. A significant difference can be observed in using the camouflage 3D-printed scaffold to conceal a deformity such as pectus excavatum. The patient had already undergone 17 operations on her funnel chest deformity, which impacted her heart and lung function. The surgery was able to conceal the deformity without compromising her organs. Furthermore, the material of the implant allows the implant to disappear completely after some time.

The implant as described herein was implanted by a minimally invasive procedure. The absorbable (e.g. fully absorbable) porous scaffold exhibits highly specialized topological and design features, and acts as a platform for injected fat tissue harvested using standard liposuction surgery. The absorbable polymer supports regeneration of natural breast tissue after implantation. Tissue may be regenerated from the patient's own body fat, without the need for cultivated stem cells or products of animal origin. The implant is absorbed over a period of time (e.g. two years), and provides a stable platform for injected fat tissue to mature, adapt to its environment and stabilize. Other implants may not be as compressible, or as flexible, and/or are not designed to disappear. For example, silicone implants need to be replaced because of complications such as capsular contracture, and silicone implants are not lifetime devices. For example, patients who have silicone implants will need up to three revision procedures at some point in their lives. The implant described herein avoids these revisions procedures by providing a porous network in which the patient's own tissues may be regenerated after implantation into surgical site. Furthermore, the reverse compressibility and spring-like characteristics of the implant allows the scaffold to be folded and/or compressed so that only a very small incision is needed, which minimises disruptions and/or surgical scars or wounds to the patient's body.

Further Illustrative Examples of Soft Tissue Reconstruction Implants of the Invention FIGS. 12A to 12C show several views of a soft tissue reconstruction implant 400 for the reconstruction of a malar region (or cheek) of a patient's body. The implant 400 may include one or more or all of the features described in connection with FIGS. 1B to 11E, and various other features.

FIGS. 12A and 12B shows a perspective top view illustration of the malar implant 400. FIG. 12C shows a side view illustration of the malar implant 400. The malar implant may include a plurality of hollow channels extending between the first outer surface region 105 and the second outer surface region 106 of the three-dimensional structure 101 of the malar implant 400. The malar implant may further include contouring lines 421 forming full and/or partial contours around the perimeter of the first outer surface region 105 and the second outer surface region 106. The malar implant may optionally include an apex region 112. A distance between the apex region 112 of the second outer surface region 105 and the first outer surface region 105 may be the largest height between any portion of the second outer surface region 105 and the first outer surface region 105.

The spring-like reversibly compressible implant allows the malar implant to mimic the softness and reverse-compressibility of the patient's cheek (such as the consistency of human fat and tissue).

FIGS. 13A to 13B show a perspective side view illustration and a top view illustration respectively of a soft tissue reconstruction implant 500 for the reconstruction of a testicular region of a patient's body. The implant 500 may include one or more or all of the features described in connection with FIGS. 1B to 12C, and various other features.

The testicular implant 500 may optionally be of a spherical and/or ovoidal shape. The testicular implant may include a plurality of hollow channels extending between the first outer surface region 105 and the second outer surface region 106 of the three-dimensional structure 101 of the testicular implant 500. Optionally, the hollow channels may be zig-zag or sinuisodal channels. The implant 500 may further include contouring lines 521 forming full and/or partial contours around the perimeter of the first outer surface region 105 and the second outer surface region 106. The testicular implant 500 may optionally include an apex region 112 at the second outer surface region 106.

Testicular implants may be performed in testicular surgery, or cosmetic cases. The testicular implant 500 may have a desired size of a testicle (e.g. an average human sized testicle) and may be implanted into a patient in the case of one or both testes being absent. The testicular implant 500 may have a dimension which allow it to fit within a scrotum after being implanted into the scrotum. A pair of testicular implants 500 may be used to create or restore symmetry in testicles, such as in cases where the patient's original testicles differ greatly in size from each other.

Similar to saline breast implants, current testicular implants may be filled with saline, and thus have similar challenges as those posed by saline breast implants. After implantation of the implant, a saline testicular implant may possibly experience hardening of the capsule around the implant. Furthermore, infections, movement of the implant within the body, and scarring from incision may be possible. The reversibly compressible testicular implant 500 allows the surgical scar to be made as small as possible, possibly reducing recovery time. The testicular implant surgery may thus be performed as an outpatient surgery, and reduced anesthesia.

Each of the implants described herein may be spring-like reversibly compressible implants, which may recover or return to its original (resting) volume after a compression force has been removed (without changing the ambient pressure and temperature). The spring-like implants may be compressible to at least (e.g. less than or equal to) 80% (or e.g. at least 70%, or e.g. at least 60%, or e.g. at least 50%, or e.g. at least 30%) of its original volume. The spring-like implants may be configured to recover at least 80% (e.g. equal to or larger than 80%) (or e.g. at least 90% or e.g. at least 95%, or e.g. at least 98%, or e.g. up to 100%) of its original volume, after the compression force exerted on the implant is removed. Surface filler lines 122 and contouring lines 119, 121, 421 also provide comfort to the user, which prevent irritation. Thus, providing a spring-like and smooth implant for insertion into the patient, without having to use outer coverings (such as in the case of saline implants). The implants may be biodegradable. Optionally, after implantation, the implants may be injected with fat, to soften the implantation area, depending on how soft the implantation area is desired to be. Alternatively, it is also possible for no fat injection to be carried out during implantation. Tissues infiltrate the inserted implant, and after a few weeks, the implant biodegrades.

Figure 14A:
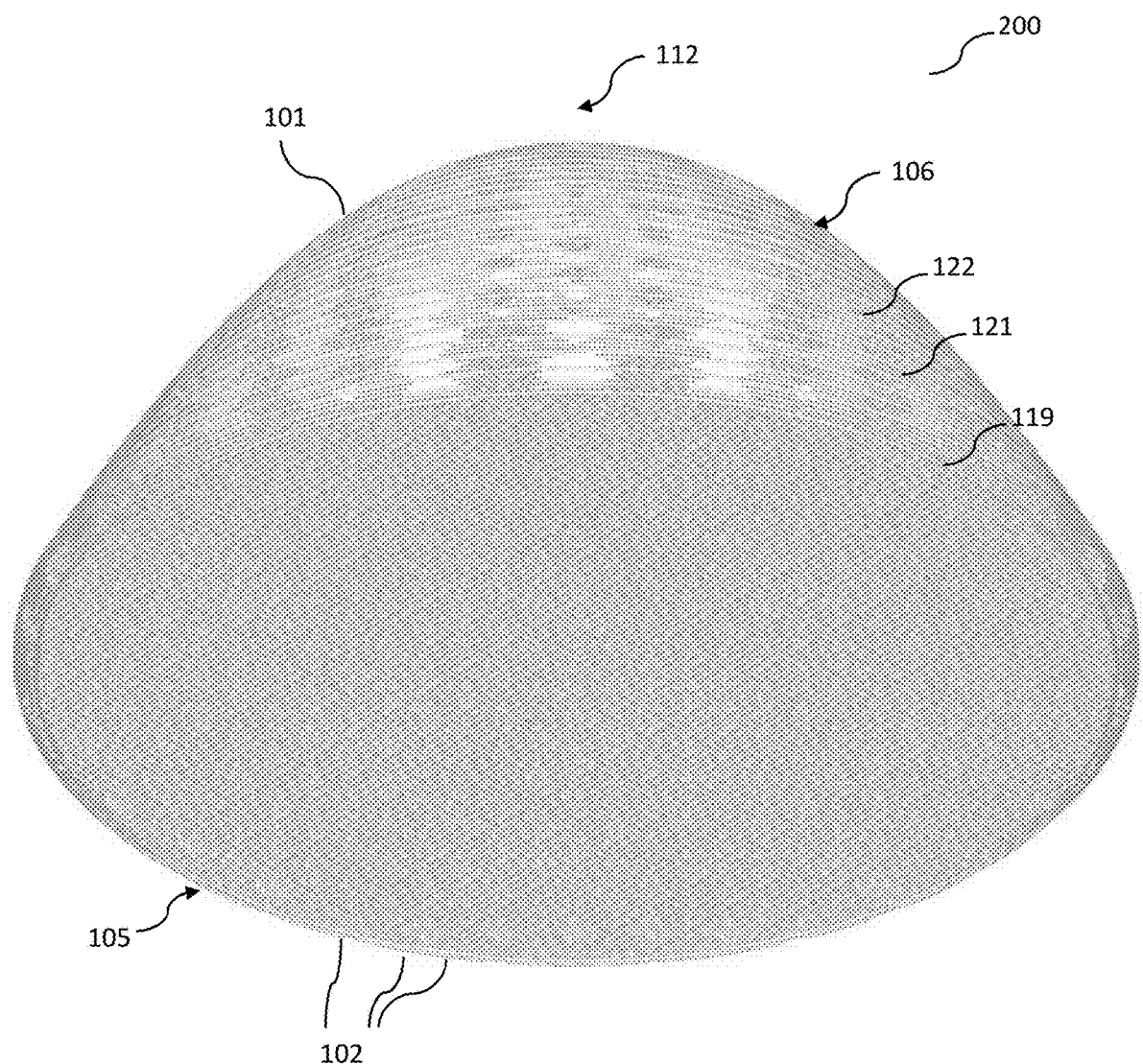
FIGS. 14A to 14C show more details of an implant described in connection with FIGS. 1B to 10B.
Figure 14B:
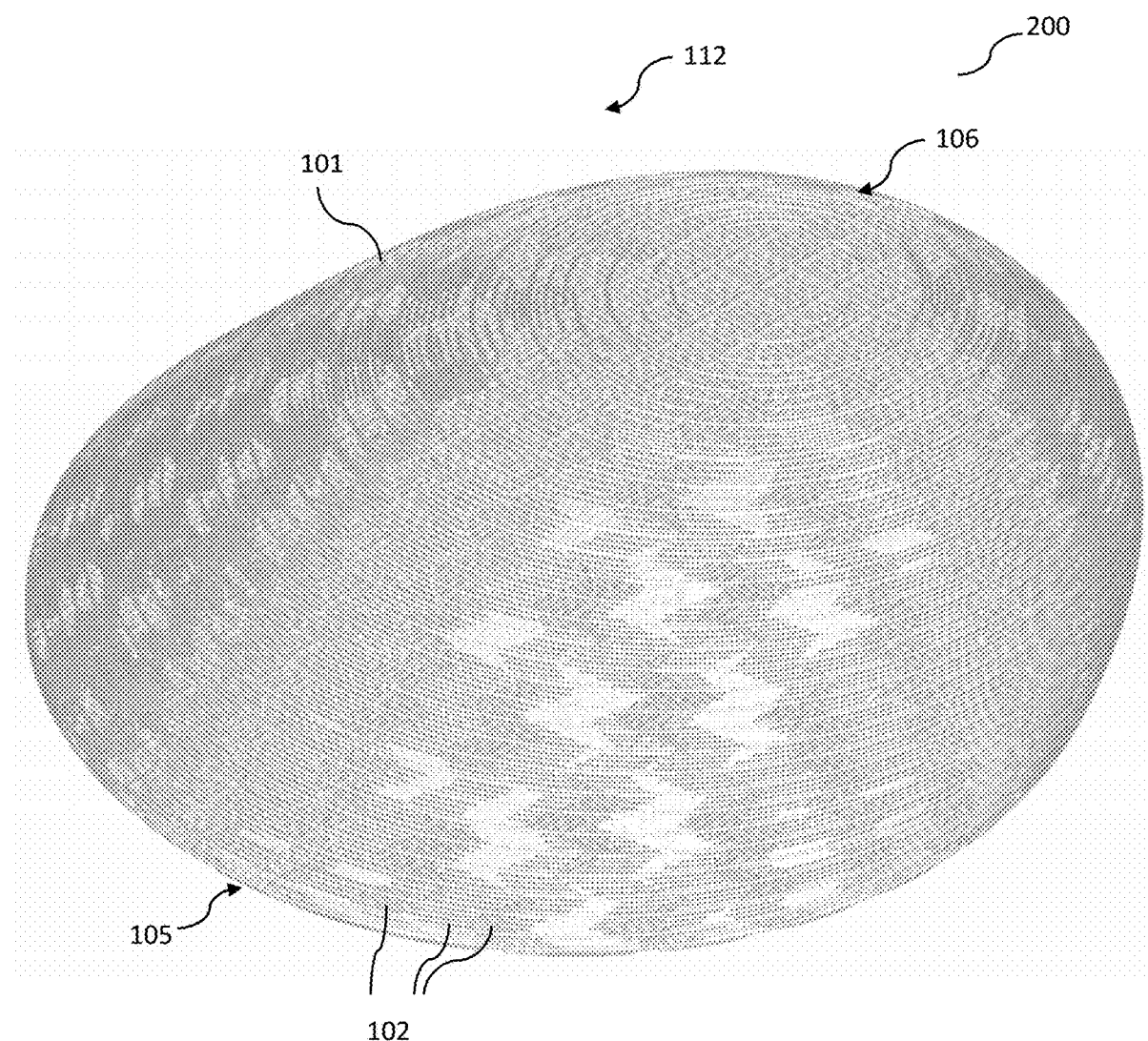
Figure 14C:
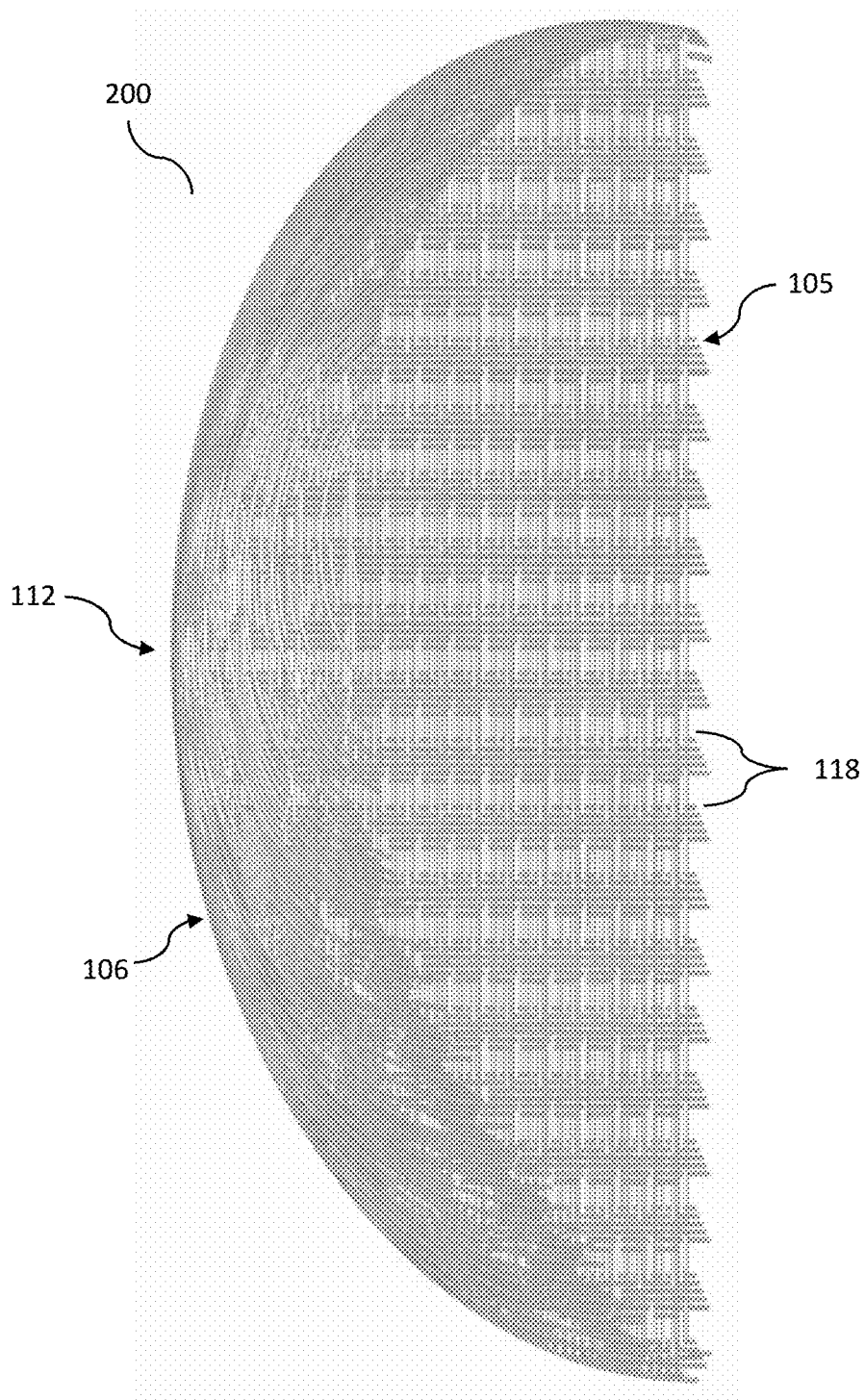

FIGS. 14A to 14C show more details of the implant 100, 200 described in connection with FIGS. 1B to 10B, which may be a soft tissue reconstruction implant for the reconstruction of a breast region of a patient's body. The soft tissue reconstruction implant 100, 200 may be a spring-like reversibly compressible implant.

The implant 100, 200 includes a plurality of unit cells 102 arranged to form a spring-like three-dimensional lattice structure 101, the three-dimensional structure comprising a resting volume of the implant. The plurality of unit cells 102 are arranged to form a porous network of the three-dimensional structure. A bulk porosity of the three-dimensional structure 101 of the implant is at least 50% or at least 60%, or at least 70%.

The individual unit cells 102 may be reversibly compressible spring-like unit cells, wherein a reversibly compressible spring-like unit cell is compressible to at least (e.g. equal to or less than) 10%, or 20% of its original volume and recovers at least (e.g. equal to or greater than) 80% of its original volume.

A surface porosity of the second outer surface region 106 may be less than the bulk porosity of the three-dimensional structure of the implant 100, 200. A material density of the implant may lie between 0.1 gr/cm$^3$ and 2 gr/cm$^3$.

The invention is further characterized by the following items.

Item 1: An implant for insertion into a patient. The implant comprises a plurality of unit cells arranged to form a three-dimensional lattice structure, the three-dimensional structure comprising a resting volume of the implant, wherein the plurality of unit cells are arranged to form a porous network of the three-dimensional structure, and wherein the three-dimensional structure is a reversibly compressible three-dimensional structure.

Item 2: The implant of item 1, wherein individual unit cells of the plurality of unit cells comprise reversibly compressible unit cells.

Item 3: The implant of item 1 or 2, wherein the unit cells of the plurality of unit cells are three-dimensional unit cells.

Item 4: The implant of any one of items 2 to 3, wherein a reversibly compressible unit cell is compressible to at least 50%, or at least 60%, or at least 70% or at least 80% of its original volume and recovering at least 80% of its original volume.

Item 5: The implant of any one of items 1 to 4, wherein the resting volume of the implant is based on a construction volume of a breast to be constructed by the implant, wherein the implant is configured to be reversibly compressible to at least the construction volume.

Item 6: The implant of any one of items 1 to 5, wherein each unit cell comprises intersecting lines of a plurality of lines, wherein the intersecting lines of the unit cell are configured to form a plurality of pores of the unit cell.

Item 7: The implant of any one of items 1 to 6, wherein the intersecting lines of the unit cell define a pore size of the unit cell.

Item 8, the subject matter of any one of examples 1 to 7, wherein an average pore size of the plurality of unit cells of the three-dimensional structure is at least 0.5 mm.

Item 9: The implant of any one of items 1 to 8, wherein a pore size of at least 50% of the plurality of unit cells of the three-dimensional structure is at least 0.5 mm.

Item 10: The implant of any one of items 1 to 9, wherein the three-dimensional structure comprises:
  a first outer surface region of the implant comprising a first surface curvature; and
  a second outer surface region of the implant comprising a second surface curvature,
  wherein the second outer surface region of the implant is contiguous to the first outer surface region of the implant at a perimeter of the first outer surface region, and
  wherein a geometry of the second outer surface region represents a geometry of a breast to be constructed by the implant.

Item 11: The implant of item 10, wherein the second outer surface region comprises:
  an upper pole portion comprising a geometry of an upper portion of the breast to be constructed by the implant, and
  a lower pole portion comprising a geometry of a lower portion of the breast to be constructed by the implant,
  wherein the upper pole portion and lower pole portion are coincident at an apex region of the second outer surface region of the three-dimensional structure.

Item 12: The implant of item 11, wherein the first outer surface region comprises a surface of least curvature of the implant,
  wherein a curvature of the upper pole portion of the second outer surface region is larger than a curvature of the first outer surface region, and
  wherein a curvature of the lower pole portion of the second outer surface region larger than or equal to the curvature of the upper pole portion of the second outer surface region.

Item 13: The implant of any one of items 1 to 13, wherein an average pore size of openings at a first outer surface region of the three-dimensional structure is at least 25% larger than an average pore size of openings at a second outer surface region of the three-dimensional structure.

Item 14: The implant of any one of items 10 to 13, wherein an average pore size of openings at the first outer surface region of the implant is at least 2 mm.

Item 15: The implant of any one of items 11 to 14, wherein a pore size of the upper pole portion of the second outer surface region increases from 0.5 mm at an upper pole interface region up to 5 mm at the apex region of the second outer surface region,
  wherein the upper pole interface region is an interface region of the three-dimensional structure at which the upper pole portion of the second outer surface region meets a portion of the perimeter of the first outer surface region.

Item 16: The implant of any one of items 11 to 15, wherein a pore size of the lower pole portion of the second outer surface region increases from 0.15 or from 2 mm at a lower pole interface region up to 6 mm, or up to 8 mm or up to 9 mm, or up to 10 mm towards the apex region of the second outer surface region,
  wherein the lower pole interface region is an interface region of the three-dimensional structure at which the lower pole portion of the second outer surface region meets a portion of the perimeter of the first outer surface region.

Item 17: The implant of any one of items 10 to 16, wherein a surface porosity of the second outer surface region is less than a bulk porosity of the three-dimensional structure of the implant.

Item 18: The implant of any one of items 1 to 17, wherein a bulk porosity of the three-dimensional structure of the implant is at least 50%, or at least 60% or at least 70% or at least 80%.

Item 19: The implant of item 18, wherein a bulk porosity of the implant lies between 50% or at least 60% or at least 70% or at least 80% and 99%.

Item 20: The implant of any one of items 1 to 19, wherein a material density of the implant lies between 0.1 gr/cm$^3$ and 2 gr/cm$^3$.

Item 21: The implant of any one of items 1 to 20, wherein the plurality of unit cells comprises a plurality of three-dimensional unit cells, wherein the three-dimensional unit cells are tetrahedral unit cells.

Item 22: The implant of any one of items 1 to 20, wherein the three-dimensional structure comprises an arrangement of layers comprising a plurality of lateral layers arranged successively over each other,
  wherein each lateral layer of the arrangement of layers comprises a lattice arrangement comprising a plurality of two-dimensional unit cells.

Item 23: The implant of item 22, wherein the plurality of two-dimensional unit cells are at least one of triangular-shaped unit cells, diamond-shaped unit cells, rhomboid-shaped unit cells, square-shaped unit cells and hexagonal-shaped unit cells.

Item 24: The implant of item 22 or 23, wherein the three-dimensional structure comprises a first outer surface region comprising a first layer of the arrangement of layers, and
  wherein the two-dimensional unit cells of the successive layers of the arrangement of layers form a plurality of hollow channels extending between the first outer surface region and a second outer surface region of the three-dimensional structure,
  wherein the second outer surface region is contiguous to the first outer surface region at a perimeter of the first outer surface region.

Item 25: The implant of item 24, wherein the plurality of hollow channels are parallel to each other.

Item 26: The implant of item 24 or 25, wherein the first outer surface region is configured to face a chest wall of the patient receiving the implant, and wherein the plurality of hollow channels are configured to be aligned with Cooper's ligaments of the patient receiving the implant.

Item 27: The implant of any one of items 24 to 26, wherein the plurality of hollow channels are slanted with respect to the first outer surface region of the implant, wherein an acute tilt angle between the plurality of hollow channels and a reference axis representing the first outer surface region is less than 60 degrees.

Item 28: The implant of any one of items 24 to 27, wherein the plurality of hollow channels are configured to converge towards a region of convergence, wherein the region of convergence is located outside the first outer surface region or the second outer surface region of the three-dimensional structure.

Item 29: The implant of any one of items 24 to 28, wherein the second outer surface region comprises an upper pole portion comprising a geometry of an upper portion of the breast to be constructed by the implant, and
  a lower pole portion comprising a geometry of a lower portion of the breast to be constructed by the implant,
  wherein the upper pole portion and lower pole portion are coincident at an apex region of the second outer surface region,
  wherein one or more channels of the plurality of hollow channels are configured to extend from the first outer surface region towards at least one of the apex region of the second outer surface region and the lower pole portion of the second outer surface region.

Item 30: The implant of item 29, wherein one or more further channels of the plurality of hollow channels are configured to extend from an upper pole portion of the second outer surface region towards at least one of the apex region and the lower pole portion of the second outer surface region.

Item 31: The implant of any one of items 1 to 30, wherein a first group of contouring lines of a plurality of lines are arranged around a perimeter of a first outer surface region of the implant.

Item 32: The implant of item 31, wherein the plurality of lines comprises a second group of contouring lines,
  wherein each contouring line of the second group of contouring lines forms a semi-contour around a second outer surface region of the implant,
  wherein the second group of contouring lines are arranged successively with respect to each between the first outer surface region and an apex region of the second outer surface region.

Item 33: The implant of item 32, wherein the second group of contouring lines are arranged at an upper pole portion of the second outer surface region, and wherein a lower pole portion of the second outer surface region is free of contouring lines.

Item 34: The implant of item 22, comprising a plurality of surface filler portions, wherein a surface filler portion comprises one or more filler lines configured to at least partially fill an opening at an outer surface region of the three-dimensional structure.

Item 35: The implant of item 34, wherein the one or more filler lines of the surface filler portion are configured to connect a group of intersecting lines defining the unit cell at the outermost surface of the three-dimensional structure.

Item 36: The implant of item 35, wherein the three-dimensional structure comprises
  a first group of unit cells at the outermost surface of the three-dimensional structure comprising surface filler portions occupying the openings of the first group of unit cells, and
  a second group of unit cells at the outermost surface of the three-dimensional structure that are free of surface filler portions.

Item 37: The implant of any one of items 34 to 36, wherein at least 20% of the plurality of unit cells at the outermost surface of the three-dimensional structure are at least partially filled with surface filler portions.

Item 38: The implant of item 37, wherein a plurality of surface filler columns and a plurality of open columns are arranged alternatingly at the outer surface regions,
wherein openings of the surface filler columns at the outermost surface of the three-dimensional structure are at least partially filled with surface filler portions, and
wherein openings of the open columns at the outermost surface of the three-dimensional structure are free of surface filler portions.

Item 39: The implant of item 38, wherein a surface filler column comprises a sidewall of a channel of the plurality of hollow channels.

Item 40: The implant of any one of items 1 to 39, wherein a c-value representing a softness of the implant lies between 20 N and 200 N.

Item 41: The implant of any one of items 6 to 40, wherein the plurality of lines comprises a surface degradable polymer material.

Item 42: The implant of any one of items 6 to 40, wherein the plurality of lines comprises a non-degradable material.

Item 43: The implant of any one of items 24 to 42, wherein the plurality of hollow channels consists of between 5 and 1000 hollow channels.

Item 44: An implant for insertion into a patient, the implant comprising:
a porous three-dimensional scaffold structure comprising an arrangement of unit cells, wherein a bulk porosity of the implant is at least 50%, or at least 60%, or at least 70%.

Item 45: The implant of item 44, wherein the bulk porosity of the implant lies between 75% and 99%.

Item 46: The implant of any one of items 44 to 45, wherein a surface porosity of the implant lies between 30% and 80%.

Item 47: The implant of any one of items 44 to 46, wherein a surface porosity of the implant lies between 40% and 70%.

Item 48: The implant of any one of items 44 to 47, wherein a surface porosity of the implant lies between 50% and 60%.

Item 49: The implant of any one of items 44 to 48, wherein a material density of the implant lies between 0.1 gr/cm$^3$ and 2 gr/cm$^3$.

Item 50: The implant of any one of items 44 to 48, wherein individual unit cells of the plurality of unit cells are spring-like unit cells, wherein the spring-like unit cells are reversibly compressible.

Item 51: The implant of any one of items 45 to 51, wherein the three-dimensional structure comprises:
a first outer surface region of the implant comprising a first surface curvature; and
a second outer surface region of the implant comprising a second surface curvature,
wherein the second outer surface region of the implant is contiguous to the first outer surface region of the implant at a perimeter of the first outer surface region, and
wherein a geometry of the second outer surface region represents a geometry of a breast to be constructed by the implant.

Item 52: The implant of item 51, wherein the second outer surface region comprises
an upper pole portion comprising a geometry of an upper portion of the breast to be constructed by the implant, and
a lower pole portion comprising a geometry of a lower portion of the breast to be constructed by the implant,
wherein the upper pole portion and lower pole portion are coincident at an apex region of the second outer surface region of the three-dimensional structure.

Item 53: The implant of item 51 or 52, wherein a surface porosity of the second outer surface region is smaller than a surface porosity of the first outer surface region.

Item 54: An implant for insertion into a patient. The implant comprises
a porous three-dimensional scaffold structure comprising an arrangement of unit cells,
wherein the plurality of unit cells are arranged to form a porous network of the three-dimensional structure,
wherein an average pore size of the plurality of unit cells of the three-dimensional structure is at least 0.5 mm.

Item 55: The implant of item 54, wherein an average pore size of the plurality of unit cells of the three-dimensional structure is at least 3 mm.

Item 56: The implant of item 54 or 55, wherein a pore size of at least 50% of the plurality of unit cells of the three-dimensional structure is at least 0.5 mm.

Item 57: The implant of any one of items 54 to 56, wherein the three-dimensional structure comprises:
a first outer surface region of the implant comprising a first surface curvature; and
a second outer surface region of the implant comprising a second surface curvature,
wherein the second outer surface region of the implant is contiguous to the first outer surface region of the implant at a perimeter of the first outer surface region, and
wherein a geometry of the second outer surface region represents a geometry of a breast to be constructed by the implant.

Item 58: The implant of item 57, wherein the second outer surface region comprises:
an upper pole portion comprising a geometry of an upper portion of the breast to be constructed by the implant, and
a lower pole portion comprising a geometry of a lower portion of the breast to be constructed by the implant,
wherein the upper pole portion and lower pole portion are coincident at an apex region of the second outer surface region of the three-dimensional structure.

Item 59: The implant of any one of items 55 to 58, wherein an average pore size at a first outer surface region of the three-dimensional structure is at least 25% larger than an average pore size at a second outer surface region of the three-dimensional structure.

Item 60: The implant of item 58 or 59, wherein an average pore size at the first outer surface region of the implant is at least 8 mm.

Item 61: The implant of any one of items 55 to 58, wherein a pore size of the upper pole portion of the second outer surface region increases from 0.5 mm at an upper pole interface region to 5 mm at the apex region of the second outer surface region,
wherein the upper pole interface region is an interface region of the three-dimensional structure, wherein the upper pole portion of the second outer surface region meets a portion of the perimeter of the first outer surface region.

Item 62: The implant of any one of items 58 to 61, wherein a pore size of the lower pole portion of the second outer surface region increases from 2 mm at a lower pole interface region up to 6 mm towards the apex region of the second outer surface region,
  wherein the lower pole interface region is an interface region of the three-dimensional structure, wherein the lower pole portion of the second outer surface region meets a portion of the perimeter of the first outer surface region.

Item 63: The implant of any one of items 54 to 62, wherein a pore size of openings at a second outer surface region of the implant increases from 0.5 mm at an upper pole interface region to 2 mm at an apex region of the second outer surface region.

Item 64: The implant of any one of items 54 to 63, wherein a pore size of openings at a second outer surface region of the implant increases from 2 mm at a lower pole interface region up to 6 mm towards an apex region.

Item 65: An implant for insertion into a patient. The implant comprises:
  a three-dimensional porous scaffold comprising a plurality of hollow channels extending between a first outer surface region and a second outer surface region of the three-dimensional porous scaffold,
  wherein the porous scaffold comprises a surface-degradable polymer material,
  wherein the first outer surface region is configured to face a chest wall of the patient receiving the implant,
  wherein a geometry of the second outer surface region represents a geometry of a breast to be constructed by the implant, and
  wherein the plurality of hollow channels are configured to be aligned with Cooper's ligaments of the patient receiving the implant.

Item 66: The implant of item 65, wherein the three-dimensional porous scaffold comprises a plurality of lateral layers arranged successively over each other, wherein each lateral layer of the arrangement of layers comprises a lattice arrangement comprising a plurality of two-dimensional unit cells,
  wherein the two-dimensional unit cells of successive layers of the plurality of lateral layers are arranged to form the plurality of hollow channels extending between the first outer surface region and the second outer surface region of the three-dimensional porous scaffold.

Item 67: The implant of item 65 or 66, wherein the second outer surface region is contiguous to the first outer surface region at a perimeter of the first outer surface region.

Item 68: the subject matter of any of items 65 to 67, wherein the plurality of hollow channels are slanted with respect to the first outer surface region of the implant, wherein an acute tilt angle between the plurality of hollow channels and a reference axis representing the first outer surface region is less than 60 degrees.

Item 69: the subject matter of any of items 65 to 68, wherein the plurality of hollow channels are configured to converge towards a region of convergence, wherein the region of convergence is located outside the first outer surface region or the second outer surface region of the three-dimensional structure.

Item 70: the subject matter of any of items 63 to 67, wherein the second outer surface region comprises an upper pole portion comprising a geometry of an upper portion of the breast to be constructed by the implant, and
  a lower pole portion comprising a geometry of a lower portion of the breast to be constructed by the implant,
  wherein the upper pole portion and lower pole portion are coincident at an apex region of the second outer surface region,
  wherein one or more channels of the plurality of hollow channels are configured to extend from the first outer surface region towards at least one of the apex region of the second outer surface region and the lower pole portion of the second outer surface region.

Item 71: The implant of item 70, wherein one or more further channels of the plurality of hollow channels are configured to extend from an upper pole portion of the second outer surface region towards at least one of the apex region and the lower pole portion of the second outer surface region.

Item 72: The implant of any of items 1 to 71, wherein the bulk porosity of the implant is at least 50%, or at least 60%, or at least 70% or at least 80% wherein the overall porosity is described by the following formula:

$$\text{Porosity} = \frac{V_V}{V_T}$$

where $V_V$ is the volume of void-space, and $V_T$ is the total volume of the scaffold.

Item 73: A method for forming an implant, wherein the method comprises:
  sequentially printing layers to form a three-dimensionally (3D) printed scaffold structure, the 3D scaffold structure defining a resting volume of the implant to be formed,
  wherein each printed layer comprises a lattice arrangement of two-dimensional unit cells,
  wherein the three-dimensionally printed structure has a bulk porosity such that the three-dimensional printed structure is compressible to at least 80% of its resting volume.

Item 74: The method of item 73, wherein an average pore size of the plurality of unit cells of the three-dimensional structure is at least 0.5 mm.

Item 75: The method of item 73 or 74, wherein sequentially printing the layers comprising
  printing a first layer to form a first outer surface region of the 3D scaffold structure, and
  printing successive layers over the first layer according to a print direction, the edge regions of the successive layers forming a second outer surface region of the 3D scaffold structure contiguous to the first outer surface region.

Item 76: The method of any one of items 73 to 75, wherein
  the unit cells of the layers of the 3D scaffold structure forming a plurality of hollow channels extending between the first outer surface region and a second outer surface region of the three-dimensional structure.

Item 77: The method of any one of items 73 to 76, wherein
  the layers are sequentially printed to form a plurality of three-dimensional unit cells of the three-dimensionally (3D) printed scaffold structure.

Item 78: A method for forming an implant, the method comprising:
  sequentially printing layers (830) to form a three-dimensionally (3D) printed structure, the 3D printed structure defining a resting volume of the implant to be formed, wherein each printed layer comprises a lattice arrangement of two-dimensional unit cells, wherein the three-dimensionally printed structure has a bulk porosity such that the three-dimensional printed structure is compressible to at least 80% of its resting volume.

Item 79: A method of tissue reconstruction or tissue augmentation, the method comprising implanting into the body of a subject an implant as defined in any of items 1 to 72 or as manufactured by a method as defined in any of item 73 to 78.

Item 80: The method of item 79, wherein the method comprises reconstruction of a body part.

Item 81: The method of item 80, wherein the body part is selected from the group consisting of the gluteal region, the calf, and a part of the face, the thorax, or a genital region.

Item 82: The method of item 81 wherein the part of the face is a cheek.

Item 83: The method of any of items 80 to 82, wherein the method comprises thorax reconstruction or breast reconstruction.

Item 84: The method of item 83, wherein the breast reconstruction is carried out following lumpectomy or mastectomy.

Item 85: The method of item 83, wherein thorax construction comprises reconstructing the pectoral or chest areas of a patient's body.

Item 86: The method of item 85, wherein the chest reconstruction comprises treating congenital pectus excavatum.

Having thus described in detail embodiments of the present invention, it is understood that the invention defined by the appended claims is not to be limited by particular details set forth in the above description, as many apparent variations thereof are possible without departing from the spirit or scope thereof.

What is claimed is:

1. A soft tissue reconstruction implant for insertion into a patient, the implant comprising:
    a plurality of unit cells arranged to form a three-dimensional lattice structure, the three-dimensional structure comprising a resting volume of the implant,
    wherein the plurality of unit cells are arranged to form a porous network of the three-dimensional structure, and
    wherein the three-dimensional structure is a reversibly compressible three-dimensional structure, and
    wherein a c-value representing a softness of the implant lies between 20 N and 200 N.

2. The implant of claim 1, wherein individual unit cells of the plurality of unit cells are reversibly compressible unit cells.

3. The implant of claim 2, wherein a reversibly compressible unit cell is compressible to at least 10% of its original volume and recovers at least 90% of its original volume.

4. The implant of claim 1, wherein an average pore size of the plurality of unit cells of the three-dimensional structure is at least 0.5 mm.

5. The implant of claim 1, wherein an average pore size of openings at a first outer surface region of the three-dimensional structure is at least 25% larger than an average pore size of openings at a second outer surface region of the three-dimensional structure.

6. The implant of claim 1, wherein the three-dimensional structure comprises
    a first outer surface region of the implant comprising a first surface curvature; and
    a second outer surface region of the implant comprising a second surface curvature,
    wherein the second outer surface region of the implant is contiguous to the first outer surface region of the implant at a perimeter of the first outer surface region, and
    wherein a geometry of the second outer surface region represents a geometry of a breast to be constructed by the implant.

7. The implant of claim 6, wherein the second outer surface region comprises
    an upper pole portion comprising a geometry of an upper portion of the breast to be constructed by the implant, and
    a lower pole portion comprising a geometry of a lower portion of the breast to be constructed by the implant,
    wherein the upper pole portion and lower pole portion are coincident at an apex region of the second outer surface region of the three-dimensional structure.

8. The implant of claim 7, wherein a pore size of openings at the second outer surface region of the implant increases from 0.5 mm at an upper pole interface region up to 5 mm at the apex region of the second outer surface region, and from up to 10 mm at a lower pole interface region down to 0.5 mm towards the apex region.

9. The implant of claim 7, wherein a pore size of openings at the second outer surface region of the implant increases from 0.5 mm at an upper pole interface region up to 5 mm at the apex region of the second outer surface region, and from 0.5 mm at a lower pole interface region up to 10 mm towards the apex region.

10. The implant of claim 1, wherein the bulk porosity of the three-dimensional structure of the implant is at least 50%.

11. The implant of claim 5, wherein a surface porosity of the second outer surface region is less than a bulk porosity of the three-dimensional structure of the implant.

12. The implant of claim 1, wherein a material density of the implant lies between 0.1 $gr/cm^3$ and 2 $gr/cm^3$.

13. The implant of claim 1, wherein the three-dimensional structure comprises
    a first outer surface region comprising a first layer of an arrangement of layers,
    wherein each layer of the arrangement of layers comprises a lattice arrangement comprising a plurality of two-dimensional unit cells, wherein two-dimensional unit cells of successive layers of the arrangement of layers form a plurality of hollow channels extending between the first outer surface region and a second outer surface region of the three-dimensional structure.

14. The implant of claim 1, comprising a first group of contouring lines of a plurality of lines arranged around a perimeter of a first outer surface region of the implant, and a second group of contouring lines of the plurality of lines,
    wherein each contouring line of the second group of contouring lines forms a semi-contour around a second outer surface region of the implant,
    wherein the second group of contouring lines are arranged successively with respect to each other between the first outer surface region and an apex region of the second outer surface region of the implant.

15. The implant of claim 1, further comprising a plurality of surface filler portions,
    wherein a surface filler portion comprises one or more filler lines configured to at least partially fill an opening at an outer surface region of the three-dimensional structure.

16. The implant of claim 1, wherein the c-value is expressed by the formula:

$$c = \frac{F_{20\%} - F_{10\%}}{\varepsilon_{20\%} - \varepsilon_{10\%}},$$

wherein $F_{20\%}$ is the force value, in N, at a compression of 20%, wherein $F_{10\%}$ is the force value, in N, at a compression of 10%, wherein $\varepsilon_{10\%}$ is the strain value at a compression of 10%, and wherein $\varepsilon_{20\%}$ is the strain value at a compression of 20%.

17. The implant of claim 1, wherein the bulk porosity of the three-dimensional structure of the implant is at least 60%.

18. The implant of claim 1, wherein the bulk porosity of the three-dimensional structure of the implant is at least 70%.

19. The implant of claim 1, wherein the bulk porosity of the three-dimensional structure of the implant is at least 80%.

* * * * *